(12) United States Patent
Karnik et al.

(10) Patent No.: US 9,610,112 B2
(45) Date of Patent: Apr. 4, 2017

(54) CRYOGENIC ENHANCEMENT OF JOINT FUNCTION, ALLEVIATION OF JOINT STIFFNESS AND/OR ALLEVIATION OF PAIN ASSOCIATED WITH OSTEOARTHRITIS

(71) Applicant: MyoScience, Inc., Redwood City, CA (US)

(72) Inventors: Jwala Karnik, Santa Barbara, CA (US); Jason Reynolds, Santa Rosa, CA (US); John Allison, Los Altos, CA (US); Clint Carnell, Park City, UT (US)

(73) Assignee: MYOSCIENCE, INC., Fremont, CA (US)

( * ) Notice: Subject to any disclaimer, the term of this patent is extended or adjusted under 35 U.S.C. 154(b) by 259 days.

(21) Appl. No.: 14/218,167

(22) Filed: Mar. 18, 2014

(65) Prior Publication Data

US 2014/0343543 A1  Nov. 20, 2014

Related U.S. Application Data

(63) Continuation-in-part of application No. 14/025,527, filed on Sep. 12, 2013, now Pat. No. 9,295,512.

(Continued)

(51) Int. Cl.
*A61B 18/02* (2006.01)
*A61F 7/12* (2006.01)
(Continued)

(52) U.S. Cl.
CPC .............. *A61B 18/02* (2013.01); *A61F 7/12* (2013.01); *A61B 2018/00041* (2013.01);
(Continued)

(58) Field of Classification Search
CPC .......... A61B 18/02; A61B 2018/00434; A61B 2018/0293; A61F 2007/0285; A61F 7/12
(Continued)

(56) References Cited

U.S. PATENT DOCUMENTS 2,319,542 A   5/1943   Hall
2,672,032 A   3/1964   Towse
(Continued)

FOREIGN PATENT DOCUMENTS

CA   2643474 A1   9/2007
EP   0043447 A2   6/1981
(Continued)

OTHER PUBLICATIONS

Non-final Office Action for U.S. Appl. No. 14/025,527 mailed on Jun. 24, 2015, 11 pages.
(Continued)

*Primary Examiner* — Deanna K Hall
(74) *Attorney, Agent, or Firm* — Kilpatrick, Townsend and Stockton, LLP

(57) ABSTRACT

A method in which a location is determined on the skin that is proximate to a sensory nerve that is associated with a painful condition. At least one needle of a cryogenic device is inserted into the location on the skin such that the needle is proximate to the sensory nerve. The device is activated such that the at least one needle creates a cooling zone about the sensory nerve, thereby eliminating or reducing severity of the painful condition.

38 Claims, 28 Drawing Sheets

Related U.S. Application Data

(60) Provisional application No. 61/800,478, filed on Mar. 15, 2013, provisional application No. 61/801,268, filed on Mar. 15, 2013.

(51) Int. Cl.
 *A61B 18/00* (2006.01)
 *A61B 18/14* (2006.01)
 *A61F 7/02* (2006.01)

(52) U.S. Cl.
 CPC .......... *A61B 2018/00434* (2013.01); *A61B 2018/00565* (2013.01); *A61B 2018/0262* (2013.01); *A61B 2018/0293* (2013.01); *A61B 2018/1425* (2013.01); *A61F 2007/0285* (2013.01)

(58) Field of Classification Search
 USPC .................................................. 128/DIG. 27
 See application file for complete search history.

(56) References Cited

U.S. PATENT DOCUMENTS

| | | | |
|---|---|---|---|
| 3,266,492 A | 8/1966 | Steinberg | |
| 3,289,424 A | 12/1966 | Lee | |
| 3,343,544 A | 9/1967 | Dunn et al. | |
| 3,351,063 A | 11/1967 | Malaker et al. | |
| 3,439,680 A | 4/1969 | Thomas, Jr. | |
| 3,483,869 A | 12/1969 | Hayhurst | |
| 3,502,081 A | 3/1970 | Amoils | |
| 3,507,283 A | 4/1970 | Thomas, Jr. | |
| 3,532,094 A | 10/1970 | Stahl | |
| 3,664,344 A | 5/1972 | Bryne | |
| 3,702,114 A | 11/1972 | Zacarian | |
| 3,795,245 A | 3/1974 | Allen, Jr. et al. | |
| 3,814,095 A | 6/1974 | Lubens | |
| 3,830,239 A | 8/1974 | Stumpf et al. | |
| 3,886,945 A | 6/1975 | Stumpf et al. | |
| 3,889,681 A | 6/1975 | Waller et al. | |
| 3,951,152 A | 4/1976 | Crandell et al. | |
| 3,993,075 A | 11/1976 | Lisenbee et al. | |
| 4,140,109 A | 2/1979 | Savic et al. | |
| 4,207,897 A | 6/1980 | Lloyd et al. | |
| 4,236,518 A | 12/1980 | Floyd | |
| 4,306,568 A | 12/1981 | Torre | |
| 4,376,376 A | 3/1983 | Gregory | |
| 4,404,862 A | 9/1983 | Harris, Sr. | |
| 4,524,771 A | 6/1985 | McGregor et al. | |
| 4,758,217 A | 7/1988 | Gueret | |
| 4,802,475 A | 2/1989 | Weshahy | |
| 4,946,460 A | 8/1990 | Merry et al. | |
| 5,059,197 A | 10/1991 | Urie et al. | |
| 5,200,170 A | 4/1993 | McDow | |
| 5,294,325 A | 3/1994 | Liu | |
| 5,334,181 A | 8/1994 | Rubinsky et al. | |
| 5,520,681 A | 5/1996 | Fuller et al. | |
| 5,571,147 A | 11/1996 | Sluijter et al. | |
| 5,647,868 A | 7/1997 | Chinn | |
| 5,747,777 A | 5/1998 | Matsuoka | |
| 5,755,753 A | 5/1998 | Knowlton | |
| 5,814,040 A | 9/1998 | Nelson et al. | |
| 5,860,970 A | 1/1999 | Goddard et al. | |
| 5,879,378 A | 3/1999 | Usui | |
| 5,899,897 A | 5/1999 | Rabin et al. | |
| 5,916,212 A | 6/1999 | Baust et al. | |
| 5,976,505 A | 11/1999 | Henderson | |
| 6,003,539 A | 12/1999 | Yoshihara | |
| 6,032,675 A | 3/2000 | Rubinsky | |
| 6,039,730 A | 3/2000 | Rabin et al. | |
| 6,041,787 A | 3/2000 | Rubinsky | |
| 6,139,545 A | 10/2000 | Utley et al. | |
| 6,141,985 A | 11/2000 | Cluzeau et al. | |
| 6,142,991 A | 11/2000 | Schatzberger | |
| 6,182,666 B1 | 2/2001 | Dobak, III | |
| 6,196,839 B1 | 3/2001 | Ross | |
| 6,238,386 B1 | 5/2001 | Mueller et al. | |
| 6,277,099 B1 | 8/2001 | Strowe et al. | |
| 6,277,116 B1 | 8/2001 | Utely et al. | |
| 6,363,730 B1 | 4/2002 | Thomas et al. | |
| 6,371,943 B1 | 4/2002 | Racz et al. | |
| 6,432,102 B2 | 8/2002 | Joye et al. | |
| 6,494,844 B1 | 12/2002 | Van Bladel et al. | |
| 6,503,246 B1 | 1/2003 | Har-Shai et al. | |
| 6,506,796 B1 | 1/2003 | Fesus et al. | |
| 6,546,935 B2 | 4/2003 | Hooven | |
| 6,551,309 B1 | 4/2003 | LePivert | |
| 6,562,030 B1 | 5/2003 | Abboud et al. | |
| 6,629,951 B2 | 10/2003 | Laufer et al. | |
| 6,648,880 B2 | 11/2003 | Chauvet et al. | |
| 6,669,688 B2 | 12/2003 | Svaasand et al. | |
| 6,672,095 B1 | 1/2004 | Luo | |
| 6,682,501 B1 | 1/2004 | Nelson et al. | |
| 6,706,037 B2 | 3/2004 | Zvuloni et al. | |
| 6,723,092 B2 | 4/2004 | Brown et al. | |
| 6,749,624 B2 | 6/2004 | Knowlton | |
| 6,761,715 B2 | 7/2004 | Carroll | |
| 6,764,493 B1 | 7/2004 | Weber et al. | |
| 6,786,901 B2 | 9/2004 | Joye et al. | |
| 6,786,902 B1 | 9/2004 | Rabin et al. | |
| 6,789,545 B2 | 9/2004 | Littrup et al. | |
| 6,840,935 B2 | 1/2005 | Lee | |
| 6,858,025 B2 | 2/2005 | Maurice | |
| 6,902,554 B2 | 6/2005 | Huttner | |
| 6,905,492 B2 | 6/2005 | Zvuloni et al. | |
| 6,960,208 B2 | 11/2005 | Bourne et al. | |
| 7,001,400 B1 | 2/2006 | Modesitt et al. | |
| 7,081,111 B2 | 7/2006 | Svaasand et al. | |
| 7,081,112 B2 | 7/2006 | Joye et al. | |
| 7,083,612 B2 | 8/2006 | Littrup et al. | |
| 7,195,616 B2 | 3/2007 | Diller et al. | |
| 7,217,939 B2 | 5/2007 | Johansson et al. | |
| 7,250,046 B1 | 7/2007 | Fallat | |
| 7,311,672 B2 | 12/2007 | Van Bladel et al. | |
| 7,367,341 B2 | 5/2008 | Anderson et al. | |
| 7,402,140 B2 | 7/2008 | Spero et al. | |
| 7,422,586 B2 | 9/2008 | Morris et al. | |
| 7,578,819 B2 | 8/2009 | Bleich et al. | |
| 7,641,679 B2 | 1/2010 | Joye et al. | |
| 7,653,438 B2 | 1/2010 | Deem et al. | |
| 7,713,266 B2 * | 5/2010 | Elkins ............... | A61B 18/02 606/20 |
| 7,850,683 B2 | 12/2010 | Elkins et al. | |
| 7,862,558 B2 | 1/2011 | Elkins et al. | |
| 7,998,137 B2 | 8/2011 | Elkins et al. | |
| 8,298,216 B2 | 10/2012 | Burger et al. | |
| 8,409,185 B2 | 4/2013 | Burger et al. | |
| 8,715,275 B2 | 5/2014 | Burger et al. | |
| 8,722,065 B2 | 5/2014 | Ishibashi et al. | |
| 9,039,688 B2 | 5/2015 | Palmer, III et al. | |
| 2002/0010460 A1 | 1/2002 | Joye et al. | |
| 2002/0013602 A1 | 1/2002 | Huttner | |
| 2002/0045434 A1 | 4/2002 | Masoian et al. | |
| 2002/0049436 A1 | 4/2002 | Zvuloni et al. | |
| 2002/0068929 A1 | 6/2002 | Zvuloni | |
| 2002/0120260 A1 | 8/2002 | Morris et al. | |
| 2002/0120261 A1 | 8/2002 | Morris et al. | |
| 2002/0120263 A1 | 8/2002 | Brown et al. | |
| 2002/0128638 A1 | 9/2002 | Chauvet et al. | |
| 2002/0156469 A1 | 10/2002 | Yon et al. | |
| 2002/0183731 A1 | 12/2002 | Holland et al. | |
| 2002/0193778 A1 | 12/2002 | Alchas et al. | |
| 2003/0036752 A1 | 2/2003 | Joye et al. | |
| 2003/0109912 A1 | 6/2003 | Joye et al. | |
| 2003/0130575 A1 | 7/2003 | Desai | |
| 2003/0181896 A1 | 9/2003 | Zvuloni et al. | |
| 2003/0195436 A1 | 10/2003 | Van Bladel et al. | |
| 2003/0220635 A1 | 11/2003 | Knowlton et al. | |
| 2003/0220674 A1 | 11/2003 | Anderson et al. | |
| 2004/0024391 A1 | 2/2004 | Cytron et al. | |
| 2004/0082943 A1 | 4/2004 | Littrup et al. | |
| 2004/0092875 A1 | 5/2004 | Kochamba | |
| 2004/0122482 A1 | 6/2004 | Tung et al. | |
| 2004/0143252 A1 | 7/2004 | Hurst | |

(56) References Cited

U.S. PATENT DOCUMENTS

| | | |
|---|---|---|
| 2004/0162551 A1 | 8/2004 | Brown et al. |
| 2004/0167505 A1 | 8/2004 | Joye et al. |
| 2004/0191229 A1 | 9/2004 | Link et al. |
| 2004/0204705 A1 | 10/2004 | Lafontaine |
| 2004/0210212 A1 | 10/2004 | Maurice |
| 2004/0215178 A1 | 10/2004 | Maurice |
| 2004/0215294 A1 | 10/2004 | Littrup et al. |
| 2004/0215295 A1 | 10/2004 | Littrup et al. |
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |
| 2005/0224086 A1 | 10/2005 | Nahon |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1 | 6/2007 | Elkins et al. |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179509 A1 | 8/2007 | Nagata et al. |
| 2007/0198071 A1 | 8/2007 | Ting et al. |
| 2007/0225781 A1* | 9/2007 | Saadat .............. A61F 7/12 607/105 |
| 2007/0255362 A1 | 11/2007 | Levinson et al. |
| 2007/0270925 A1 | 11/2007 | Levinson |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1 | 7/2008 | Elkins et al. |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0171334 A1 | 7/2009 | Elkins et al. |
| 2009/0248001 A1* | 10/2009 | Burger .............. A61F 7/00 606/21 |
| 2009/0264876 A1 | 10/2009 | Roy et al. |
| 2009/0299357 A1 | 12/2009 | Zhou |
| 2010/0114191 A1 | 5/2010 | Newman |
| 2010/0168725 A1 | 7/2010 | Babkin et al. |
| 2010/0305439 A1 | 12/2010 | Shai et al. |
| 2011/0144631 A1 | 6/2011 | Elkins et al. |
| 2011/0196267 A1 | 8/2011 | Mishelevich |
| 2012/0065629 A1 | 3/2012 | Elkins et al. |
| 2012/0089211 A1 | 4/2012 | Curtis et al. |
| 2012/0259322 A1* | 10/2012 | Fourkas ............ A61B 18/02 606/21 |
| 2012/0265187 A1 | 10/2012 | Palmer, III et al. |
| 2013/0253605 A1 | 9/2013 | Bennett et al. |
| 2013/0324990 A1 | 12/2013 | Burger et al. |
| 2014/0249519 A1 | 9/2014 | Burger et al. |
| 2014/0276539 A1 | 9/2014 | Allison et al. |
| 2014/0276708 A1 | 9/2014 | Karnik et al. |
| 2014/0343542 A1 | 11/2014 | Karnik et al. |
| 2014/0343544 A1 | 11/2014 | Carnell et al. |

FOREIGN PATENT DOCUMENTS

| | | |
|---|---|---|
| EP | 0777123 A1 | 6/1997 |
| EP | 0955012 A1 | 11/1999 |
| EP | 1074273 A1 | 2/2001 |
| EP | 1377327 B1 | 9/2007 |
| EP | 1862125 A2 | 12/2007 |
| EP | 2 499 984 A1 | 9/2012 |
| GB | 1360353 B | 7/1974 |
| GB | 1402632 A | 8/1975 |
| JP | 60-013111 | 1/1985 |
| JP | H04-357945 A | 12/1992 |
| JP | 05-038347 | 2/1993 |
| JP | 10-014656 A | 1/1998 |
| JP | 2001-178737 A | 7/2001 |
| JP | 2005-080988 A | 3/2005 |
| JP | 2006-130055 A | 5/2006 |
| JP | 2008-515469 A | 5/2008 |
| RU | 2254060 | 6/2005 |
| WO | WO 97/49344 A1 | 12/1997 |
| WO | WO 01/97702 A1 | 12/2001 |
| WO | WO 02/02026 A1 | 1/2002 |
| WO | WO 02/092153 A2 | 11/2002 |
| WO | WO 2004/039440 A1 | 5/2004 |
| WO | WO 2004/045434 A2 | 6/2004 |
| WO | WO 2004/089460 A2 | 10/2004 |
| WO | WO 2005/000106 A2 | 1/2005 |
| WO | WO 2005/079321 A2 | 9/2005 |
| WO | WO 2005/096979 A1 | 10/2005 |
| WO | WO 2006/012128 A2 | 2/2006 |
| WO | WO 2006/023348 A1 | 3/2006 |
| WO | WO 2006/044727 A2 | 4/2006 |
| WO | WO 2006/062788 A2 | 6/2006 |
| WO | WO 2006/125835 A1 | 11/2006 |
| WO | WO 2006/127467 A2 | 11/2006 |
| WO | WO 2007/025106 A2 | 3/2007 |
| WO | WO 2007/037326 A1 | 4/2007 |
| WO | WO 2007/089603 A2 | 8/2007 |
| WO | WO 2007/109656 A2 | 9/2007 |
| WO | WO 2007/129121 A1 | 11/2007 |
| WO | WO 2007/135629 A1 | 11/2007 |
| WO | WO 2009/026471 A1 | 2/2009 |
| WO | WO 2010/075438 A1 | 7/2010 |
| WO | WO 2010/075448 A1 | 7/2010 |
| WO | WO 2014/146105 A1 | 9/2014 |
| WO | WO 2014/146106 A1 | 9/2014 |
| WO | WO 2014/146122 A1 | 9/2014 |
| WO | WO 2014/146127 A1 | 9/2014 |

OTHER PUBLICATIONS

Notification of Transmittal of the International Search Report and the Written Opinion of the International Searching Authority, or the Declaration; International Search Report and the Written Opinion of

(56) References Cited

OTHER PUBLICATIONS the International Searching Authority for corresponding International Patent Application No. PCT/US2014/031081 mailed on Oct. 29, 2014, 14 pages.
Invitation to Pay Additional Fees and, Where Applicable, Protest Fee with Partial International Search Report mailed Aug. 5, 2014, from PCT Application No. PCT/US2014/031081, 2 pages.
International Search Report and Written Opinion mailed Aug. 8, 2014, from PCT Application No. PCT/US2014/031107, 16 pages.
International Search Report and Written Opinion mailed Aug. 8, 2014, from PCT Application No. PCT/US2014/031113, 14 pages.
International Search Report and Written Opinion mailed Sep. 4, 2014, from PCT Application No. PCT/US2014/031079, 16 pages.
U.S. Appl. No. 14/025,527, filed Sep. 12, 2013 by Allison et al. (Unpublished.).
U.S. Appl. No. 14/218,146, filed Mar. 18, 2014 by Karnik et al. (Unpublished.).
U.S. Appl. No. 14/218,901, filed Mar. 18, 2014 by Carnell et al. (Unpublished.).
U.S. Appl. No. 14/218,925, filed Mar. 18, 2014 by Karnik et al. (Unpublished.).
Bohannon et al., Interrater reliability of a modified Ashworth scale of muscle spasticity, Physical Therapy, 67(2): 206, 1987, 4 pages.
Boyd et al., "Objective measurement of clinical findings in the use of botulinum toxin type A for the management of children with cerebral palsy", European Journal of Neurology, 6: s23-s35, 1999, 13 pages.
Farrar et al., "Validity, reliability, and clinical importance of change in a 0-10 numeric rating scale measure of spasticity; a post hoc analysis of a randomized, double-blind, placebo-controlled trial", Clinical Therapeutics, 30:5: 974-985, 2008, 12 pages.
Gallagher et al., "Prospective validation of clinically important changes in pain severity measured on visual analog scale", Annals of Emergency Medicine, 38:6;633-638, 2001, 6 pages.
Morris, "Ashworth and Tardieu scales: Their clinical relevance for measuring spasticity in adult and paediatric neurological populations", Physical Therapy Reviews, 7: 53-62, 2002, 10 pages.
Page et al., "Clinically important differences for the upper-extremity Fugl-Meyer scale in people with minimal to moderate impairment due to chronic stroke", Physical Therapy, 92: 791-798, 2012, 10 pages.
Penn et al., "Intrathecal baclofen for severe spinal spasticity", The New England Journal of Medicine, Jun. 8, 1989;320(23):1517-21, 5 pages.
Shaw et al., "BoTULS: a multicentre randomised controlled trial to evaluate the clinical effectiveness and cost-effectiveness of treating upper limb spasticity due to stroke with botulinum toxin type A", Health Technology Assessment; 14:26, 2010, 158 pages.
Sullivan et al., "Fugl-Meyer assessment of sensorimotor function after stroke: Standardized training procedure for clinical practice and clinical trials", Stroke. 2011; 42:427-432, 27 pages.
U.S. Appl. No. 61/116,050, filed Nov. 19, 2008 by Holland et al., 46 pages. (expired).
Advanced Cosmetic Intervention, Inc. [webpage], retrieved from the Internet: <<http://www.acisurgery.com>>, copyright 2007, 1 page.
Cryopen, LLC [Press Release], "CyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.
Cryopen, LLC., [webpage], retrieved from the Internet: <<http://cryopen.com/>>, copyright 2006-2008, 2 pages total.
Cryosurgical Concepts, Inc., [webpage] "CryoProbe™" retrieved from the Internet: << http://www.cryo-surgical.com//>> on Feb. 8, 2008, 2 pages total.
Dasiou-Plankida, "Fat injections for facial rejuvenation: 17 years experience in 1720 patients," Journal of Cosmetic Dermatology, Oct. 22, 2004; 2(3-4): 119-125.
Foster et al., "Radiofrequency Ablation of Facial Nerve Branches Controlling Glabellar Frowning", Dermatol Surg. Dec. 2009; 35(12):1908-1917.
Har-Shai et al., "Effect of skin surface temperature on skin pigmentation during contact and intralesional cryosurgery of hypertrophic scars and Kleoids," Journal of the European Academy of Dermatology and Venereology, Feb. 2007, vol. 21, issue 2, pp. 191-198.
Magalov et al., "Isothermal volume contours generated in a freezing gel by embedded cryo-needles with applications to cryo-surgery," Cryobiology Oct. 2007, 55(2):127-137.
Metrum CryoFlex, Cryoablation in pain management brochure, 2012, 5 pages.
Metrum CryoFlex, Cryosurgery probes and accessories catalogue, 2009, 25 pages.
One Med Group, LLC., [webpage] "CryoProbe™" retrieved from the Internet: << http://www.onemedgroup.com/>> on Feb. 4, 2008, 2 pages total.
Rewcastle et al., "A model for the time dependent three-dimensional thermal distribution within iceballs surrounding multiple cryoprobes," Med Phys. Jun. 2001;28(6):1125-1137.
Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.
Utley et al., "Radiofrequency Ablation of the Nerve to the Corrugator Muscle for the Elimination of Glabellar Furrowing," Arch. Facial Plastic Surgery 1: 46-48, 1999.
Yang et al., "Apoptosis induced by cryo-injury in human colorectal cancer cells is associated with mitochondrial dysfunction.," International Journal of Cancer, 2002, vol. 103, No. 3, pp. 360-369.
Restriction Requirement for U.S. Appl. No. 14/025,527 mailed on Feb. 20, 2015, 7 pages.

\* cited by examiner

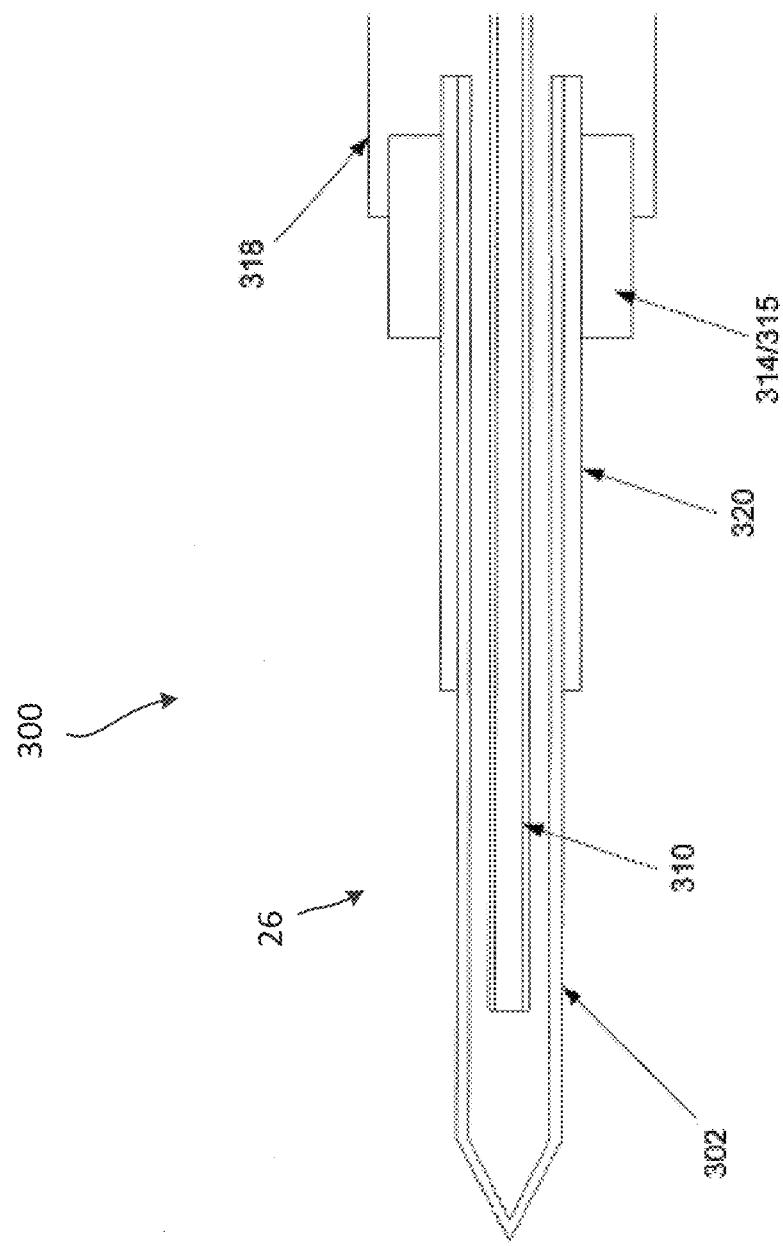

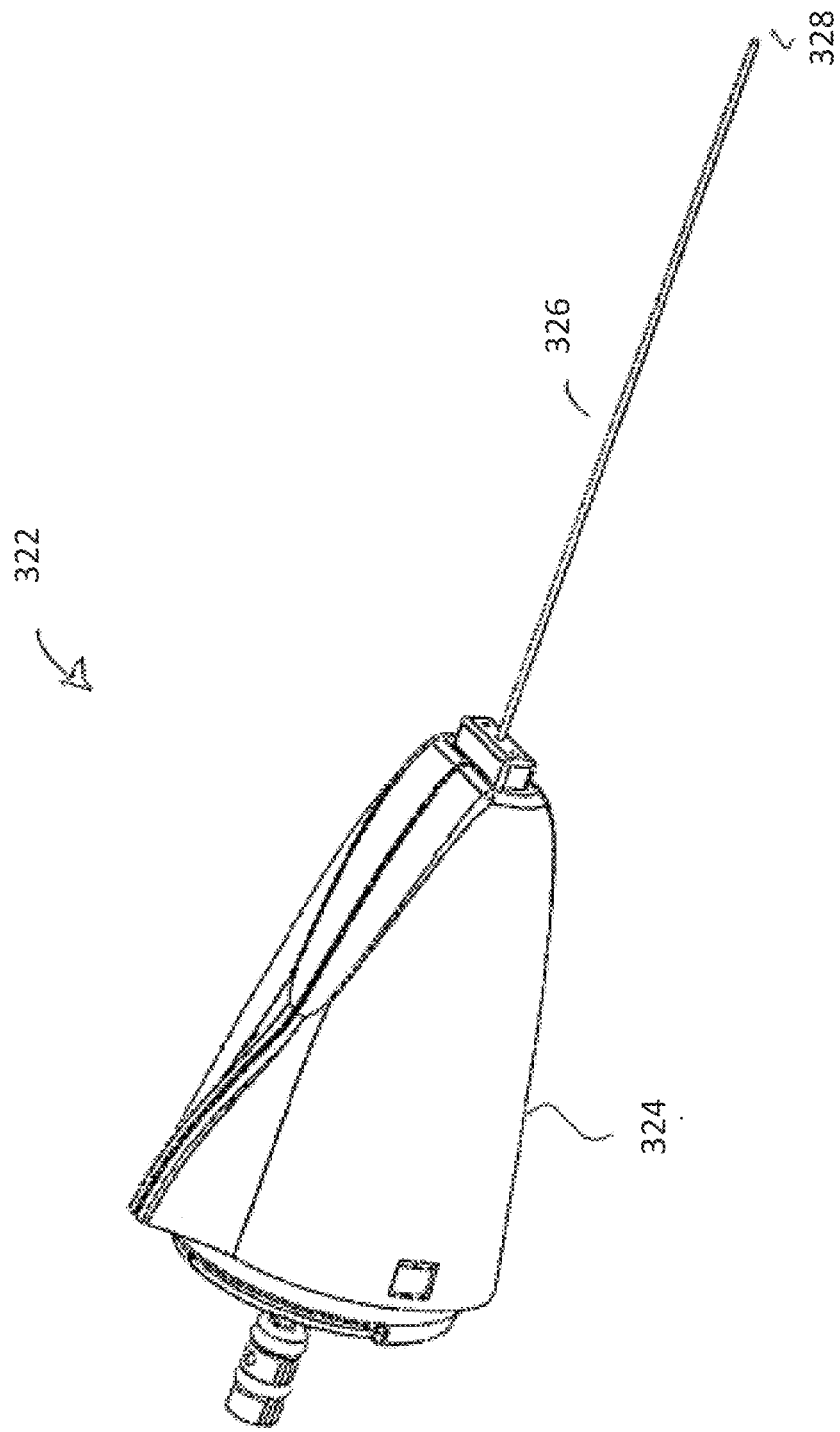

CRYOGENIC ENHANCEMENT OF JOINT FUNCTION, ALLEVIATION OF JOINT STIFFNESS AND/OR ALLEVIATION OF PAIN ASSOCIATED WITH OSTEOARTHRITIS

CROSS-REFERENCES TO RELATED APPLICATIONS

The present application is a continuation-in-part of U.S. Nonprovisional patent application Ser. No. 14/025,527 filed Sep. 12, 2013, entitled "Methods and Devices for Pain Management;" and claims benefit of priority to U.S. Provisional Patent Application No. 61/800,478 filed Mar. 15, 2013, entitled "Methods and Devices for Pain Management" and to U.S. Provisional Patent Application No. 61/801,268 filed Mar. 15, 2013, entitled "Cryogenic Blunt Dissection Methods and Devices," the complete disclosures of which are incorporated herein by reference.

BACKGROUND OF THE INVENTION

The present invention is directed to medical devices, systems, and methods, particularly for those which employ cold for treatment of pain in a patient. Embodiments of the invention include cryogenic cooling needles that can be advanced through skin or other tissues to improve joint function, reduce stiffness, and/or inhibit transmission of pain signals, particularly for alleviation of joint degradation associated with osteoarthritis.

According to the CDC, 50 million people are affected with osteoarthritis (OA). It has been estimated that 1 in 2 people will get symptomatic knee OA in their lifetime, with these odds increasing to 2 in 3 people among those who are obese. With the combination of the aging Baby Boomer population, increased longevity of U.S. citizens and the obesity epidemic, the rising prevalence of OA may contribute even more heavily to the severe health and economic effects already present. OA often causes weakness and disability, interferes with a patient's physical and mental welfare, as well as, work productivity, and results in join replacement.

Though a variety of pain management techniques currently exist for those with OA, the most common nonsurgical options provide slow-acting and/or short-term relief. Medication, often in the form of non-steroidal anti-inflammatory drugs (NSAIDs) and opioids, comes with an array of side effects such as nausea and vomiting. Medication also presents the possibility of more serious effects such as increased risk of heart attack and stroke, and tolerance or dependency issues. Surgical strategies tend to be reserved for more severe cases and are limited by the risks and complications typically associated with surgery including bleeding, bruising, scarring, and infection.

A nonsurgical, minimally invasive, long-lasting approach to chronic pain management is desirable. In general, it would be advantageous to provide improved devices, systems, and methods for management of chronic and/or acute pain. Such improved techniques may avoid or decrease the systemic effects of toxin-based neurolysis and pharmaceutical approaches, while decreasing the invasiveness and/or collateral tissue damage of at least some known pain treatment techniques.

BRIEF SUMMARY OF THE INVENTION

Many embodiments provide a novel, minimally invasive device and method for providing focused cold therapy to target peripheral sensory nerve tissue that offers long-lasting pain relief through cryoanalgesia. The device and method may operate on the cryobiology principle that localized exposure to controlled moderately low temperature conditions can alter tissue function. The device and therapy may treat nerves with low temperatures via a cold probe in the form of an assembly of small diameter needles, creating a highly localized treatment zone around the probe. This focused cold therapy (FCT) may create a conduction block that prevents nerve signaling. Further, preliminary studies have provided preliminary evidence of the device and method effectiveness on motor nerves and have been shown to be safe with no serious device-related adverse events.

Some embodiments of the invention are related to a method in which a location of a zone is determined with reference to the skin surface adjacent or proximate to a sensory nerve associated with a painful condition. At least one needle of a cryogenic device may be inserted through the skin and into the zone. The needle may be positioned adjacent to the sensory nerve. The device may be activated such that the at least one needle creates a cooling zone about the sensory nerve, thereby eliminating or reducing severity of the painful condition. Nerve stimulation, ultrasound guidance, or other nerve localization or visualization techniques are not used to determine the location in some embodiments but may be used in other embodiments.

Some embodiments of the invention are also related to a method in which location is determined of a treatment zone with reference to the skin surface that is proximate or adjacent to an infrapatellar branch of a saphenous nerve that is associated with osteo-arthritis of a knee of the leg and other painful conditions associated with the inferior aspect of the anterior knee. At least one needle of a cryogenic device may be inserted through the skin and positioned adjacent to the infrapatellar branch. The device may be activated such that the at least one needle creates a cooling zone about the infrapatellar branch, thereby eliminating or reducing severity of pain caused by the osteo-arthritis. In a similar method, branches of the anterior femoral cutaneous nerve and the lateral femoral cutaneous nerve may be treated.

In many embodiments, body landmarks are used to determine location of the zone.

In many embodiments, the treatment zone approximates a rectangle defined by: a first line/boundary laterally separated by a first predetermined distance from a patellar tendon of the knee; a second line/boundary parallel to the first line/boundary, the second line/boundary being laterally separated by a second predetermined distance from a lower pole of a patella of the knee; a third line/boundary transversely connecting the first and second line/boundaries, the third line/boundary extending from a tibial tubercle of the knee; and a fourth line/boundary transversely connecting the first and second line/boundary, the fourth line/boundary extending from a mid-portion of the patella.

In some embodiments the first predetermined distance may range between 25 and 60 mm. In some embodiments the second predetermined distance may range between 30 and 70 mm.

In many embodiments, the at least one needle is used repeatedly to create a plurality of cooling zones along the second line between the third and fourth lines.

In many embodiments, the at least one needle is used repeatedly to create a plurality of cooling zones along the first and second lines between the third and fourth lines.

In many embodiments, the cryogenic device comprises a plurality of needles, and plurality of needles of the cryogenic device are inserted into the treatment zone to create the cooling zone.

In many embodiments, the plurality of needles are used repeatedly to create a plurality of cooling zones along the second line between the third and fourth lines.

In many embodiments, the plurality of needles are used repeatedly to create a plurality of cooling zones along the first and second lines between the third and fourth lines.

In many embodiments, the cooling zone causes Wallerian degeneration to occur at the infrapatellar branch.

In some embodiments, the at least one needle may be inserted into the skin along an insertion axis and may be positioned adjacent a target tissue by: bending the needle after insertion through the skin away from the insertion axis, and advancing the needle to the target tissue. Optionally, the needle may have a blunt distal tip.

Many embodiments of the invention relate to a system having a body having a handle, a coolant supply path within the body, and at least one cryogenic needle supported by the handle and coupled to the coolant supply path, system being adapted to target a particular sensory nerve. For example, an infrapatellar branch of a saphenous nerve.

In many embodiments, the system is used without the benefit of nerve stimulation to locate the particular sensory nerve. However, in other embodiments, the system includes a device for nerve stimulation.

In many embodiments, the system can be adapted by configuring a controller of the system to cause the needle to generate a cooling zone for a particular period of time, temperature, and size to affect the particular sensory nerve. These values can be adjusted in real-time using feedback provided by sensory detection and/or interpolational calculations of heater power draw.

In many embodiments, a plurality of needles are supported by the handle and coupled to the handle.

In many embodiments, the at least one needle, or each needle of the plurality, are of a particular size to target an infrapatellar branch of a saphenous nerve. This can be achieved by using a needle with a specific length and diameter.

In many embodiments, the at least one needle, or each needle of the plurality, includes a thermally conductive coating that is of a particular length for protecting tissue above the particular sensory nerve. The conductive coating can be coupled to a heater.

Some embodiments relate to a method in which location of a treatment zone is located on skin that is proximate to an infrapatellar branch of a saphenous nerve that is associated with osteo-arthritis of a knee of the leg. The infrapatellar branch of the saphenous nerve is treated, thereby eliminating or reducing severity of pain caused by the osteo-arthritis. In many embodiments, thermal energy is used to treat the nerve. In some embodiments, RF is used to create the thermal energy. In many embodiments, the treatment is made with an injection of a substance. In many embodiments, the substance is phenol. In many embodiments, the substance is ethyl alcohol.

Some embodiments may relate to a method in which a treatment surface of a cryogenic device is positioned within a treatment zone below skin of a patient body. The treatment zone is proximate a selected branch of a nerve associated with osteo-arthritis of a joint. This is done by identifying a region of the skin with reference to hard tissue structures identifiable tactilely and/or visibly through the skin and then advancing at least one probe of a cryogenic device through the skin and into the treatment zone underlying the region.

The device may be activated such that the at least one probe creates a cooling zone about the selected branch, the cooling zone inducing Wallerian degeneration of the selected branch so as to eliminate or reduce severity of pain caused by the osteoarthritis.

In yet another embodiment of the invention, a system is provided for treating osteoarthritis of a knee of a leg of a patient. The system may include a guide for identifying treatment zone with reference to a skin surface and a treatment probe configured for directing a treatment under the skin surface with reference to the zone. The treatment may be configured to modulate an infrapatellar branch of the saphenous nerve associated with osteoarthritis of a knee of a leg.

In some embodiments, the guide may be placed on the skin surface relative to body landmarks. Optionally, the guide may be configured to identify a zone with an uppermost/superior boundary defined by a midline of a patella of the leg. In some embodiments, the guide may be configured to identify a zone with a bottommost/inferior boundary defined by a tibial tubercle of the leg. In some embodiments, the guide may be configured to identify a zone with a medial boundary defined by a first distance lateral to a medial aspect of the patellar tendon of the leg. In some embodiments, the guide may be configured to identify a zone with a lateral boundary defined by a second distance lateral to a lower pole of a patella of the leg. In some embodiments the first distance may be between 25 and 60 mm. In some embodiments the second distance may be between 30 and 70 mm.

In some embodiments, a system for alleviating osteoarthritis (OA) of a joint having a nerve is provided. The system may include a needle having a proximal end, a distal end, and a needle lumen therebetween. The needle may be configured for insertion proximate to the nerve. A cooling fluid supply lumen may extend distally within the needle lumen to a distal portion of the needle lumen. A cooling fluid source may be couplable to the cooling fluid supply lumen to direct cooling fluid flow into the needle lumen so that liquid from the cooling flow vaporizes within the needle lumen to provide cooling to the nerve such that impact of the OA on function and/or stiffness of the joint is mitigated.

In some embodiments, the cooling flow vaporizes within the needle lumen to provide a cryozone having a cross-sectional area between 14-40 mm$^2$. In some embodiments, the cross-sectional area may be between 20-36 mm$^2$ or between 25-30 mm$^2$. The cryozone may be defined by a 0° C. isotherm (cooling zone). Optionally, the cooling flow may vaporize within the needle lumen to provide a cryozone having a volume between 65-105 mm$^3$, or between 80-90 mm.

The system may further include a heating element coupled with a proximal portion of the needle. The heating element may be configured to deliver heating phases to the skin of the patient. A processor may be configured to control the cooling fluid flow and the heating element in response to operator input. The processor may be configured to provide a treatment cycle in response to a treatment instruction. The treatment cycle may include at least one heating phase and one cooling phase. A degree of skin warmer throughout the treatment cycle may be provided. The degree of skin warmer may comprises 25-42° C. skin warmer throughout the treatment cycle. In some embodiments the skin warmer may be 30° C., 35° C., or 40° C.

The at least one heating phase may comprise a pre-warm phase with the heating element before the at least one cooling phase. The pre-warm phase may have a duration of 8-12 seconds or may end when the heating element reaches the skin warming temperature. The at least one cooling phase may have a duration between 20-65 seconds. In some embodiments, it may be beneficial to have shorter duration cooling phases. Some embodiments may provide sufficient treatment with a 30 second, 35 second, or 40 second cooling phase. In some embodiments, a 60 second cooling phase may be used.

In some embodiments, the at least one cooling phase may have a duration of less than 40 seconds. The 40 second cooling phase may be sufficient to create a cryozone having a cross-sectional area between 14-40 mm². In some embodiments, the at least one cooling phase may have a duration of less than 40 seconds and may create a cryozone having a volume between 65-105 mm³.

Optionally, the at least one heating phase may also include a post-warm phase. The post-warm phase may have a duration of 12-18 seconds. Preferably, the distal portion of the needle may have a temperature of at least 0° C. at the end of the post-warm phase. In some embodiments, the needle may have a length of 5-7 mm. Optionally, the processor may be configured to provide an audio or visual alert at completion of a treatment cycle.

In some embodiments, a kit for treating a target tissue under a skin of a patient so as to reduce or eliminate joint pain experienced by the patient may be provide. The kit may include embodiments of the system described above. The kit may further include a guide for placement on the skin surface relative to body landmarks for identifying a skin region overlying the target tissue. The guide may identify a skin region overlying an infrapatellar branch of a saphenous nerve of the patient, for example. The guide may be configured to identify the skin region with a superior boundary defined by a midline of a patella of the leg; an inferior boundary defined by a tibial tubercle of the leg; a medial boundary defined by a distance lateral to a medial aspect of the patellar tendon of the leg ranging between 40-48 mm; a lateral boundary defined by a distance lateral to a lower pole of a patella of the leg ranging between 50-60 mm. In some embodiments, the kit of may include a percutaneous electrical nerve stimulation device.

In some embodiments, a method for alleviating osteoarthritis (OA) of a joint having a nerve is provided. The method may include positioning a distal end of a cryogenic cooling needle having a needle lumen proximal the nerve. Thereafter, a treatment cycle may be delivered to the target tissue with the cryogenic cooling needle. The treatment cycle may include a cooling phase where cooling fluid flows into the needle lumen so that liquid from the cooling flow vaporizes within the needle lumen to cooling to the nerve such that impact of the OA on function and/or stiffness of the joint is mitigated.

In some embodiments, the treatment cycle may be configured to generate a cryozone having a cross-sectional area between 14-40 mm². The cryozone may be defined by a 0° C. isotherm. Optionally, the treatment cycle may be configured to generate a cryozone having a volume between 65-105 mm³.

The method may include providing a degree of skin warmer throughout the delivery of the treatment cycle, the degree of skin warmer may be 20-42° C. skin warmer throughout the treatment cycle. Optionally, the cryogenic cooling needle may further comprises a heating element coupled with a proximal portion of the needle and the treatment cycle may further comprises at least one heating phase. The at least one heating phase may comprise a pre-warm phase with the heating element before the at least one cooling phase. The pre-warm phase may have a duration of 8-12 seconds.

The at least one cooling phase may have a duration of 20-65 seconds after the pre-warm phase. The at least one cooling phase may have a duration of less than 40 seconds and may be configured to create a cryozone having a cross-sectional area between 14-40 mm².

The at least one cooling phase may have a duration of less than 40 seconds and may create a cryozone having a volume between 65-105 mm³.

In some embodiments the at least one heating phase further comprises a post-warm phase. The post-warm phase may have a duration of 12-18 seconds. Preferably, the distal portion of the needle may have a temperature of at least 0° C. at the end of the post-warm phase. In some embodiments, the needle may have a length of 5-7 mm.

The method may further include placing a guide on a skin surface relative to body landmarks so as to identify a skin region overlying the target tissue. The guide may identify a skin region overlying an infrapatellar branch of a saphenous nerve of the patient. The guide may identify the skin region with a superior boundary defined by a midline of a patella of the leg; an inferior boundary defined by a tibial tubercle of the leg; a medial boundary defined by a distance lateral to a medial aspect of the patellar tendon of the leg ranging between 40-48 mm; a lateral boundary defined by a distance lateral to a lower pole of a patella of the leg ranging between 50-60 mm. Optionally, the method may further include identifying the target tissue using a percutaneous electrical nerve stimulation device or using ultrasound imaging.

In some embodiments a system for improving function and/or stiffness of joint of a patient is provided. The joint may be affected with osteoarthritis. The system may include a plurality of 27 gauge needles, each having length between 5-7 mm and being spaced apart by not more than 3 mm. Each needle may further comprise a proximal end, a distal end, and a needle lumen therebetween. A heating element may be coupled with a proximal portion of the each of the plurality of needles. The heating element may be configured to deliver warming phases to the skin of the patient when the plurality of needles are inserted proximal to the nerve. A plurality of cooling fluid supply lumens may extend distally within the each of the plurality of needle lumens to a distal portion of each of the plurality of needle lumens. A cooling fluid source may be coupleable to the plurality of cooling fluid supply lumens to direct cooling fluid flow into the plurality of needle lumens so that liquid from the cooling flow vaporizes within the plurality of needle lumens to deliver adjacent cooling phases to the nerve such that impact of the OA on function and/or stiffness of the joint is mitigated. A processor may be configured to control the cooling fluid flow and the heating element in response to operator input.

Further features of the invention, its nature and various advantages will be more apparent from the accompanying drawings and the following detailed description.

BRIEF DESCRIPTION OF THE DRAWINGS

FIGS. 3A-3E illustrate an exemplary embodiment of a clad needle probe, according to some embodiments of the invention;

DETAILED DESCRIPTION OF THE INVENTION

The present invention provides improved medical devices, systems, and methods. Embodiments of the invention may facilitate remodeling of target tissues disposed at and below the skin, optionally to treat pain associated with a sensory nerve. Embodiments of the invention may utilize a handheld refrigeration system that can use a commercially available cartridge of fluid refrigerant. Refrigerants well suited for use in handheld refrigeration systems may include nitrous oxide and carbon dioxide. These can achieve temperatures approaching −90° C.

Sensory nerves and associated tissues may be temporarily impaired using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a longer lasting treatment that limits or avoids inflammation and mobilization of skeletal muscle satellite repair cells. In some embodiments, axonotmesis with Wallerian degeneration of a sensory nerve is desired, which may be induced using treatment temperatures from about −20° C. to about −100° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling methods and devices may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", U.S. patent application Ser. No. 13/325,004 entitled "Method for Reducing Hyperdynamic Facial Wrinkles", and U.S. Pub. No. 2009/0248001 entitled "Pain Management Using Cryogenic Remodeling," the full disclosures of which are each incorporated by reference herein.

Figure 1A:
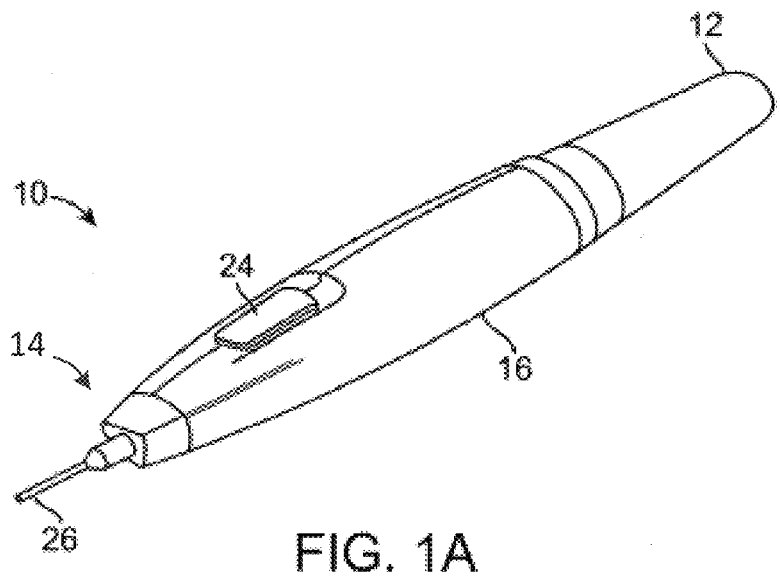
FIG. 1A is a perspective view of a self-contained subdermal cryogenic remodeling probe and system, according to some embodiments of the invention.
Figure 1B:
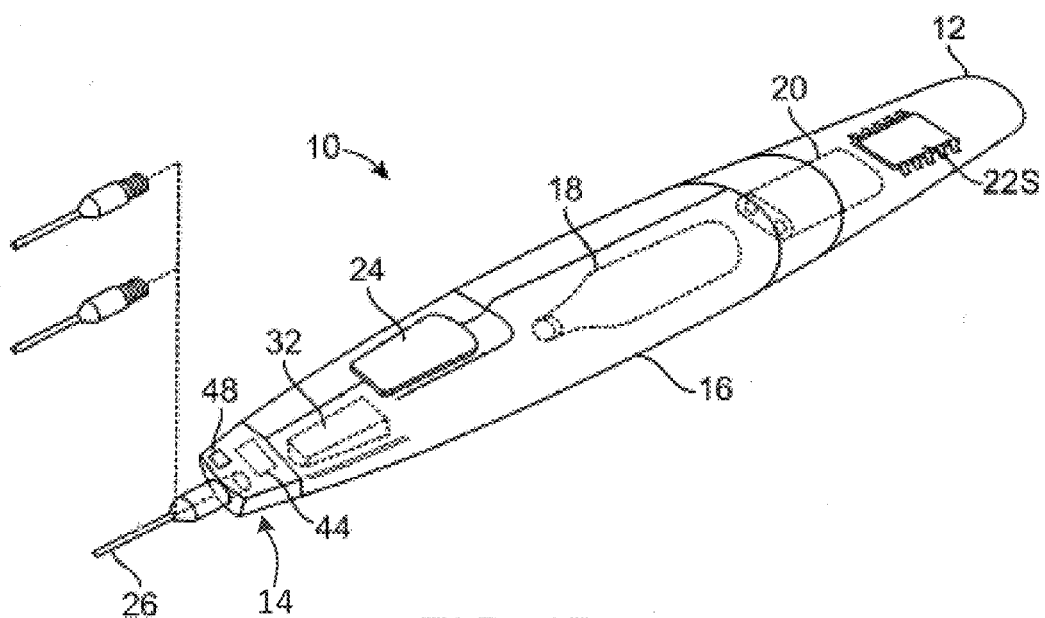
FIG. 1B is a partially transparent perspective view of the self-contained probe of FIG. 1A, showing internal components of the cryogenic remodeling system and schematically illustrating replacement treatment needles for use with the disposable probe according to some embodiments of the invention.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22 having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 which may thereby help to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 may be a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 may comprise a 30 g needle having a sharpened distal end that is axially sealed. Probe 26 may have an axial length between distal end 14 of housing 16 and the distal end of the needle of between about 0.5 mm and 15 cm, preferably having a length from about 3 mm to about 10 mm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 may comprise a 16 g or smaller size needle, often comprising a 20 g needle or smaller, typically comprising a 25, 26, 27, 28, 29, or 30 g or smaller needle.

In some embodiments, probe 26 may comprise two or more needles arranged in a linear array, such as those disclosed in previously incorporated U.S. Pat. No. 7,850,683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Patent Publication No. 2008/0200910 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 may be releasably coupled with body 16 so that it may be replaced after use with a sharper needle (as indicated by the dotted line) or with a needle having a different configuration. In exemplary embodiments, the needle may be threaded into the body, press fit into an aperture in the body or have a quick disconnect such as a detent mechanism for engaging the needle with the body. A quick disconnect with a check valve may be advantageous since it may permit decoupling of the needle from the body at any time without excessive coolant discharge. This can be a useful safety feature in the event that the device fails in operation (e.g. valve failure), allowing an operator to disengage the needle and device from a patient's tissue without exposing the patient to coolant as the system depressurizes. This feature may also be advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 may comprise a canister, sometimes referred to herein as a cartridge, containing a liquid under pressure, with the liquid preferably having a boiling temperature of less than 37° C. at one atmosphere of pressure. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which are incorporated herein by reference.

The exemplary cooling fluid supply 18 may comprise a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2A:
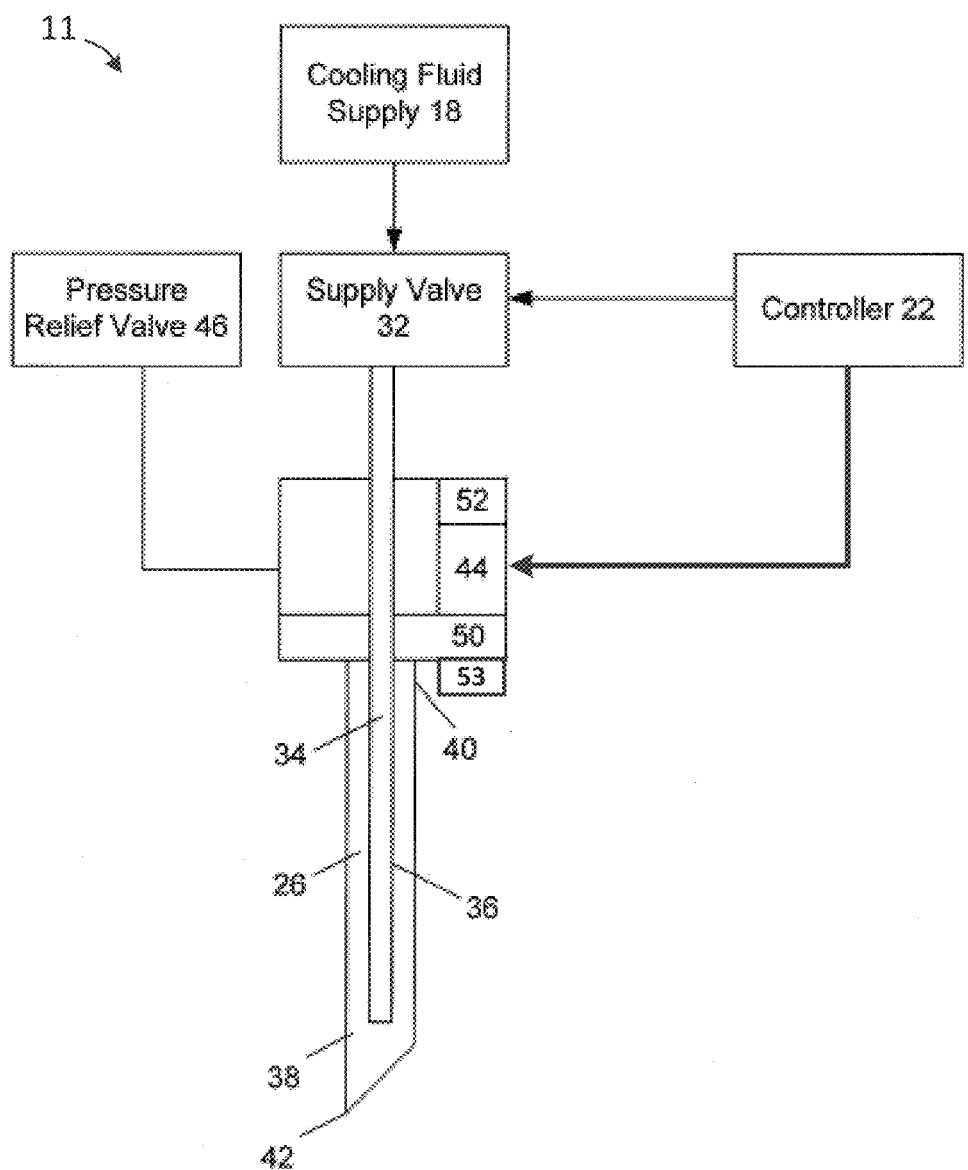
FIG. 2A schematically illustrates exemplary components that may be included in the treatment system.

Referring now to FIG. 2A, schematic 11 shows a simplified diagram of cryogenic cooling fluid flow and control. The flow of cryogenic cooling fluid from fluid supply 18 may be controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2A, an optional heater (not illustrated) may be used to heat cooling fluid supply 18 so that heated cooling fluid flows through valve 32 and through a lumen 34 of a cooling fluid supply tube 36. In some embodiments a safety mechanism can be included so that the cooling supply is not overheated. Examples of such embodiments are disclosed in commonly assigned International Publication No. WO 2010075438, the entirety of which is incorporated by reference herein.

Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Patent Publication No. 2008/0154254 entitled "Dermal and Transdermal Cryogenic Microprobe Systems and Methods," the entire contents of which are incorporated herein by reference. Previously incorporated U.S. Patent Publication No. 2008/0200910 also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve may allow better temperature control in the needle, minimizing transient temperatures. Further details on exhaust volume are disclosed in previously incorporated U.S. Pat. Pub. No. 2008/0200910.

The heater 44 may be thermally coupled to a thermally responsive element 50, which is supplied with power by the controller 22 and thermally coupled to a proximal portion of the needle 26. The thermally responsive element 50 can be a block constructed from a material of high thermal conductivity and low heat capacity, such as aluminum. A first temperature sensor 52 (e.g., thermistor, thermocouple) can also be thermally coupled the thermally responsive element 50 and communicatively coupled to the controller 22. A second temperature sensor 53 can also be positioned near the heater 44, for example, such that the first temperature sensor 52 and second temperature sensor 53 are placed in different positions within the thermally responsive element 50. In some embodiments, the second temperature sensor 53 is placed closer to a tissue contacting surface than the first temperature sensor 52 is placed in order to provide comparative data (e.g., temperature differential) between the sensors 52, 53. The controller 22 can be configured to receive temperature information of the thermally responsive element 50 via the temperature sensor 52 in order to provide the heater 44 with enough power to maintain the thermally responsive element 50 at a particular temperature.

The controller 22 can be further configured to monitor power draw from the heater 44 in order to characterize tissue type, perform device diagnostics, and/or provide feedback for a tissue treatment algorithm. This can be advantageous over monitoring temperature alone, since power draw from the heater 44 can vary greatly while temperature of the thermally responsive element 50 remains relatively stable. For example, during treatment of target tissue, maintaining the thermally responsive element 50 at 40° C. during a cooling cycle may take 1.0 W initially (for a needle <10 mm in length) and is normally expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned. Correlations with power draw and correlated device and/or tissue conditions can be determined experimentally to determine acceptable treatment power ranges.

In some embodiments, it may be preferable to limit frozen tissue that is not at the treatment temperature, i.e., to limit the size of a formed cooling zone within tissue. Such cooling zones may be associated with a particular physical reaction, such as the formation of an ice-ball, or with a particular temperature profile or temperature volume gradient required to therapeutically affect the tissue therein. To achieve this, metering coolant flow could maintain a large thermal gradient at its outside edges. This may be particularly advantageous in applications for creating an array of connected cooling zones (i.e., fence) in a treatment zone, as time would be provided for the treatment zone to fully develop within the fenced in portion of the tissue, while the outer boundaries maintained a relatively large thermal gradient due to the repeated application and removal of refrigeration power. This could provide a mechanism within the body of tissue to thermally regulate the treatment zone and could provide increased ability to modulate the treatment zone at a prescribed distance from the surface of the skin. A related treatment algorithm could be predefined, or it could be in response to feedback from the tissue.

Such feedback could be temperature measurements from the needle 26, or the temperature of the surface of the skin could be measured. However, in many cases monitoring temperature at the needle 26 is impractical due to size constraints. To overcome this, operating performance of the sensorless needle 26 can be interpolated by measuring characteristics of thermally coupled elements, such as the thermally responsive element 50.

Additional methods of monitoring cooling and maintaining an unfrozen portion of the needle include the addition of a heating element and/or monitoring element into the needle itself. This could consist of a small thermistor or thermocouple, and a wire that could provide resistive heat. Other power sources could also be applied such as infrared light, radiofrequency heat, and ultrasound. These systems could also be applied together dependent upon the control of the treatment zone desired.

Alternative methods to inhibit excessively low transient temperatures at the beginning of a refrigeration cycle might be employed instead of or together with the limiting of the exhaust volume. For example, the supply valve 32 might be cycled on and off, typically by controller 22, with a timing sequence that would limit the cooling fluid flowing so that only vaporized gas reached the needle lumen 38 (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Patent Pub. No. 2008/0154254.

Figure 2B:
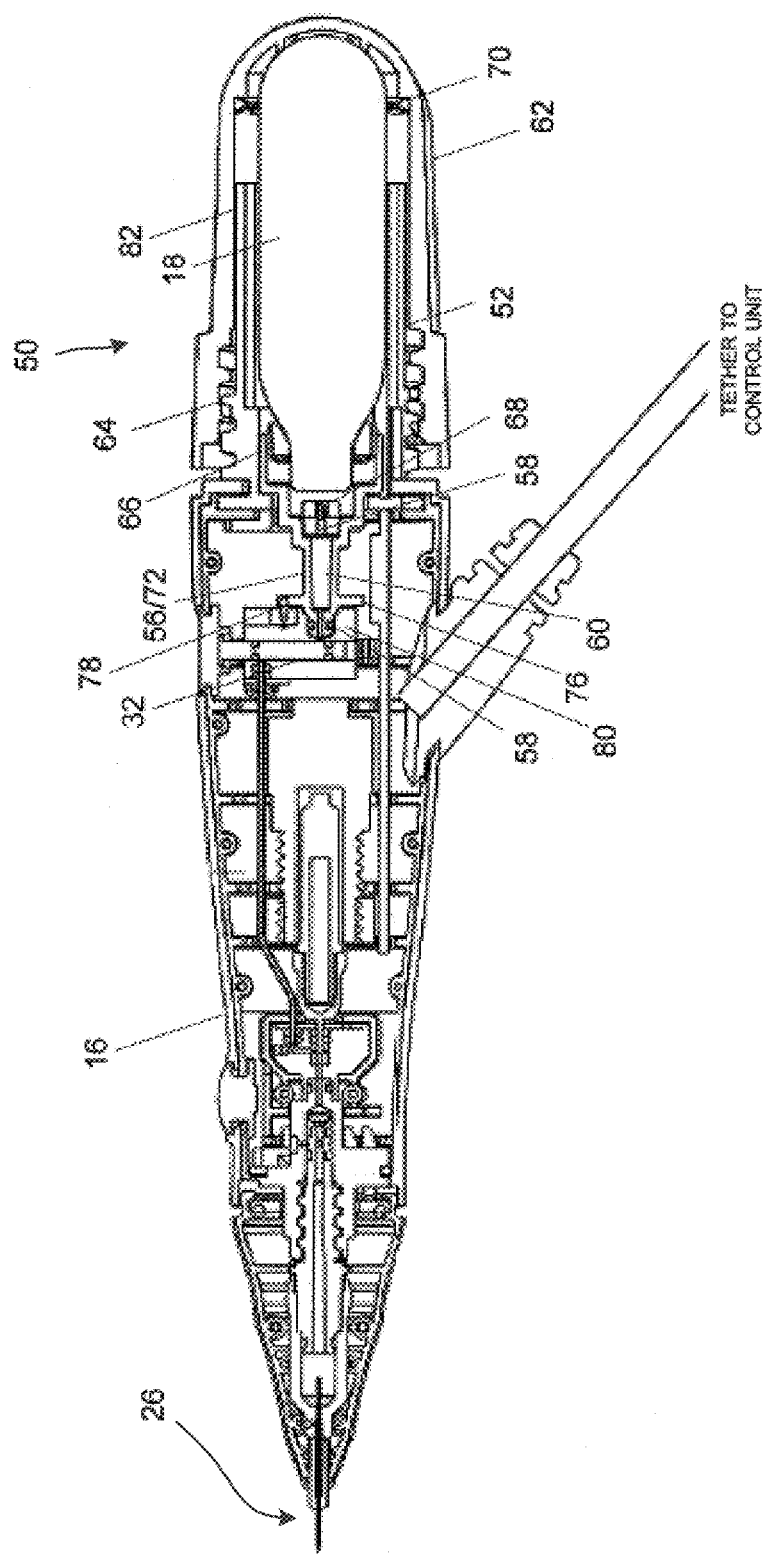
FIG. 2B is a cross-sectional view of the system of FIG. 1A, according to some embodiments of the invention.

FIG. 2B shows a cross-section of the housing 16. This embodiment of the housing 16 may be powered by an external source, hence the attached cable, but could alternatively include a portable power source. As shown, the housing includes a cartridge holder 50. The cartridge holder 50 includes a cartridge receiver 52, which may be configured to hold a pressured refrigerant cartridge 18. The cartridge receiver 52 includes an elongated cylindrical passage 54, which is dimensioned to hold a commercially available cooling fluid cartridge 18. A distal portion of the cartridge receiver 52 includes a filter device 56, which has an elongated conical shape. In some embodiments, the cartridge holder 50 may be largely integrated into the housing 16 as shown, however, in alternative embodiments, the cartridge holder 50 is a wholly separate assembly, which may be pre-provided with a coolant fluid source 18.

The filter device 56 may fluidly couple the coolant fluid source (cartridge) 18 at a proximal end to the valve 32 at a distal end. The filter device 56 may include at least one particulate filter 58. In the shown embodiment, a particulate filter 58 at each proximal and distal end of the filter device 56 may be included. The particulate filter 58 can be configured to prevent particles of a certain size from passing through. For example, the particulate filter 58 can be constructed as a microscreen having a plurality of passages less than 2 microns in width, and thus particles greater than 2 microns would not be able to pass.

The filter device 56 also includes a molecular filter 60 that is configured to capture fluid impurities. In some embodiments, the molecular filter 60 is a plurality of filter media (e.g., pellets, powder, particles) configured to trap molecules of a certain size. For example, the filter media can comprise molecular sieves having pores ranging from 1-20 Å. In another example, the pores have an average size of 5 Å. The molecular filter 60 can have two modalities. In a first mode, the molecular filter 60 will filter fluid impurities received from the cartridge 18. However, in another mode, the molecular filter 60 can capture impurities within the valve 32 and fluid supply tube 36 when the system 10 is not in use, i.e., when the cartridge 18 is not fluidly connected to the valve 32.

Alternatively, the filter device 56 can be constructed primarily from ePTFE (such as a GORE material), sintered polyethylene (such as made by POREX), or metal mesh. The pore size and filter thickness can be optimized to minimize pressure drop while capturing the majority of contaminants. These various materials can be treated to make it hydrophobic (e.g., by a plasma treatment) and/or oleophobic so as to repel water or hydrocarbon contaminants.

It has been found that in some instances fluid impurities may leach out from various aspects of the system 10. These impurities can include trapped moisture in the form of water molecules and chemical gasses. The presence of these impurities is believed to hamper cooling performance of the system 10. The filter device 56 can act as a desiccant that attracts and traps moisture within the system 10, as well as chemicals out gassed from various aspects of the system 10. Alternately the various aspects of the system 10 can be coated or plated with impermeable materials such as a metal.

Figure 2C:
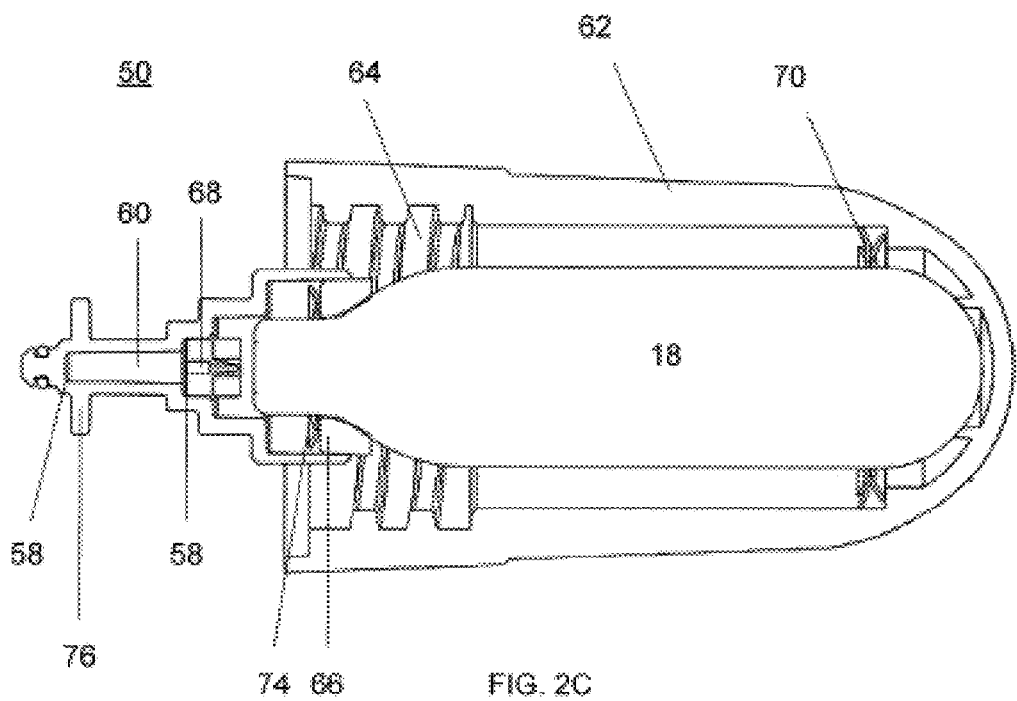
FIGS. 2C and 2D are cross-sectional views showing exemplary operational modes of the system of FIG. 2B.
Figure 2D:
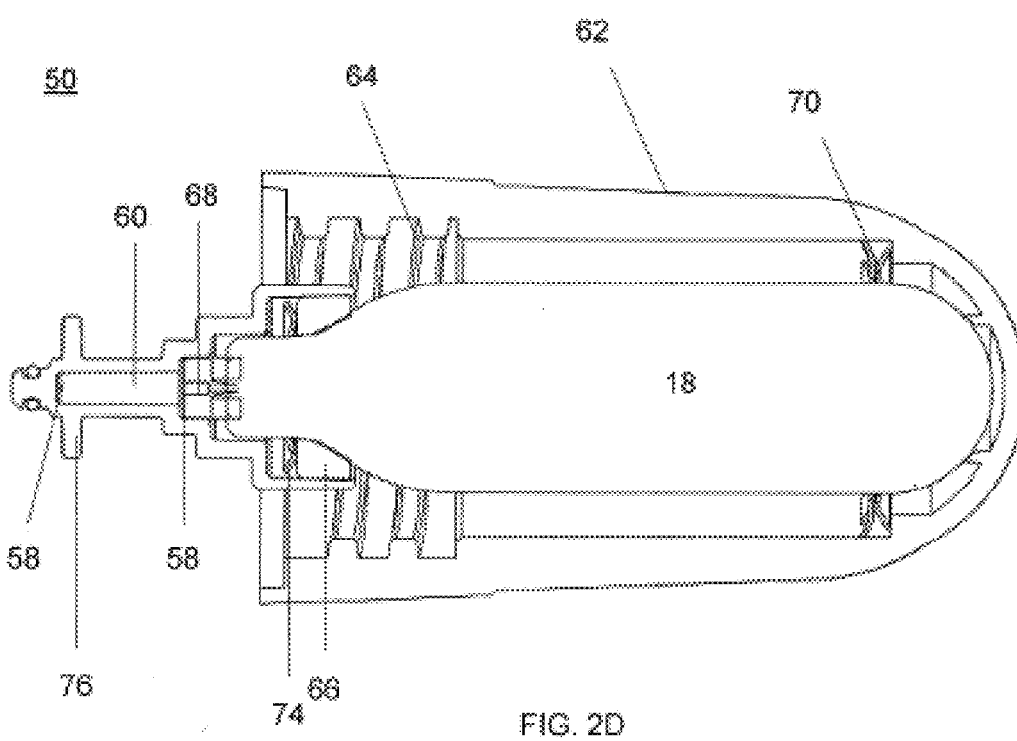

As shown in FIG. 2B and in more detail in FIG. 2C and FIG. 2D, the cartridge 18 can be held by the cartridge receiver 52 such that the cartridge 18 remains intact and unpunctured. In this inactive mode, the cartridge may not be fluidly connected to the valve 32. A removable cartridge cover 62 can be attached to the cartridge receiver 52 such that the inactive mode is maintained while the cartridge is held by the system 10.

In use, the cartridge cover 62 can be removed and supplied with a cartridge containing a cooling fluid. The cartridge cover 62 can then be reattached to the cartridge receiver 52 by turning the cartridge cover 62 until female threads 64 of the cartridge cover 62 engage with male threads of the cartridge receiver 52. The cartridge cover 62 can be turned until resilient force is felt from an elastic seal 66, as shown in FIG. 2C. To place the system 10 into use, the cartridge cover 62 can be further turned until the distal tip of the cartridge 18 is punctured by a puncture pin connector 68, as shown in FIG. 2D. Once the cartridge 18 is punctured, cooling fluid may escape the cartridge by flowing through the filter device 56, where the impurities within the cooling fluid may be captured. The purified cooling fluid then passes to the valve 32, and onto the coolant supply tube 36 to cool the probe 26. In some embodiments the filter device, or portions thereof, may be replaceable.

In some embodiments, the puncture pin connector 68 can have a two-way valve (e.g., ball/seat and spring) that is closed unless connected to the cartridge. Alternately, pressure can be used to open the valve. The valve closes when the cartridge is removed. In some embodiments, there may be a relief valve piloted by a spring which is balanced by high-pressure nitrous when the cartridge is installed and the system is pressurized, but allows the high-pressure cryogen to vent when the cryogen is removed. In addition, the design can include a vent port that vents cold cryogen away from the cartridge port. Cold venting cryogen locally can cause condensation in the form of liquid water to form from the surrounding environment. Liquid water or water vapor entering the system can hamper the cryogenic performance. Further, fluid carrying portions of the cartridge receiver 52 can be treated (e.g., plasma treatment) to become hydrophobic and/or oleophobic so as to repel water or hydrocarbon contaminants.

Figure 3A:
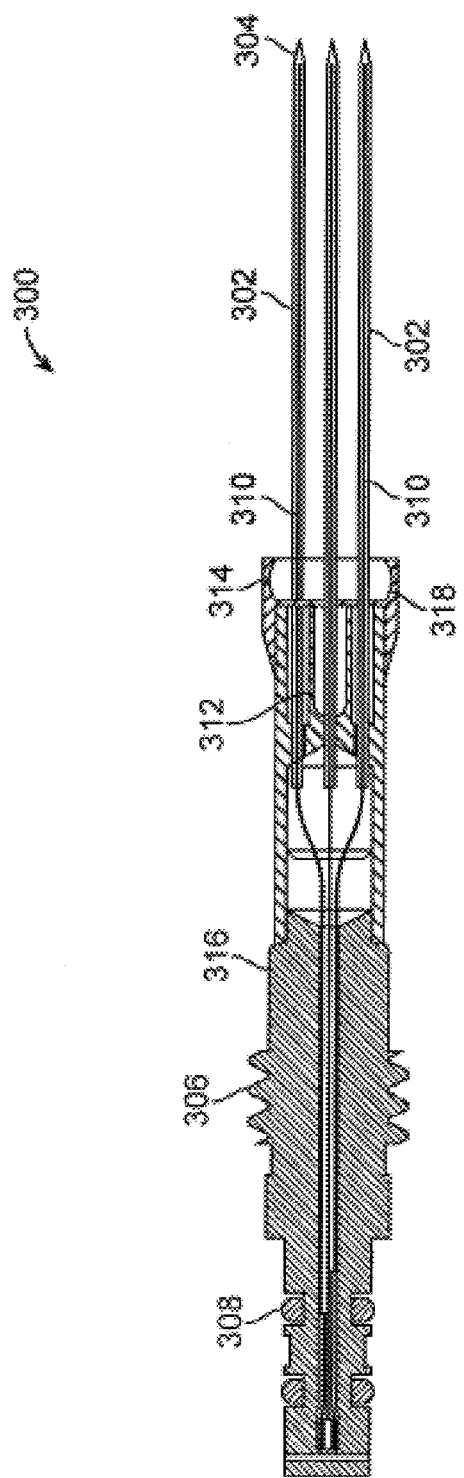

Turning now to FIG. 3A and FIG. 3B, an exemplary embodiment of probe 300 having multiple needles 302 is described. In FIG. 3A, probe housing 316 includes threads 306 that allow the probe to be threadably engaged with the housing 16 of a cryogenic device. O-rings 308 fluidly seal the probe housing 316 with the device housing 16 and prevent coolant from leaking around the interface between the two components. Probe 300 includes an array of three distally extending needle shafts 302, each having a sharpened, tissue penetrating tip 304. Using three linearly arranged needles allows a greater area of tissue to be treated as compared with a single needle. In use, coolant flows through lumens 310 into the needle shafts 302 thereby cooling the needle shafts 302. Ideally, only the distal portion of the needle shaft 302 would be cooled so that only the target tissue receives the cryogenic treatment. However, as the cooling fluid flows through the probe 300, probe temperature decreases proximally along the length of the needle shafts 302 towards the probe hub 318. The proximal portion of needle shaft 302 and the probe hub 318 contact skin and may become very cold (e.g. −20° C. to −25° C.) and this can damage the skin in the form of blistering or loss of skin pigmentation. Therefore it would be desirable to ensure that the proximal portion of needle shaft 302 and hub 318 remains warmer than the distal portion of needle shaft 302. A proposed solution to this challenge is to include a heater element 314 that can heat the proximal portion of needle shaft 302 and an optional temperature sensor 312 to monitor temperature in this region. To further this, a proximal portion of the needle shaft 302 can be coated with a highly thermally conductive material, e.g., gold, that is conductively coupled to both the needle shaft 302 and heater element 314. Details of this construction are disclosed below.

In the exemplary embodiment of FIG. 3A, resistive heater element 314 is disposed near the needle hub 318 and near a proximal region of needle shaft 302. The resistance of the heater element is preferably 1Ω to 1K Ω, and more preferably from 5Ω to 50Ω. Additionally, a temperature sensor 312 such as a thermistor or thermocouple is also disposed in the same vicinity. Thus, during a treatment as the needles cool down, the heater 314 may be turned on in order to heat the hub 318 and proximal region of needle shaft 302, thereby preventing this portion of the device from cooling down as much as the remainder of the needle shaft 302. The temperature sensor 312 may provide feedback to controller 22 and a feedback loop can be used to control the heater 314. The cooling power of the nitrous oxide may eventually overcome the effects of the heater, therefore the microprocessor may also be programmed with a warning light and/or an automatic shutoff time to stop the cooling treatment before skin damage occurs. An added benefit of using such a heater element is the fact that the heat helps to moderate the flow of cooling fluid into the needle shaft 302 helping to provide more uniform coolant mass flow to the needles shaft 302 with more uniform cooling resulting.

The embodiment of FIG. 3A illustrates a heater fixed to the probe hub. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cryogenic Remodeling for Cosmetic and Other Treatments," the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape.

FIG. 3B illustrates a cross-section of the needle shaft 302 of needle probe 300. The needle shaft can be conductively coupled (e.g., welded, conductively bonded, press fit) to a conductive heater 314 to enable heat transfer therebetween. The needle shaft 302 is generally a small (e.g., 20-30 gauge) closed tip hollow needle, which can be between about 0.2 mm and 15 cm, preferably having a length from about 0.3 cm to about 1.5 cm. The conductive heater element 314 can be housed within a conductive block 315 of high thermally conductive material, such as aluminum and include an electrically insulated coating, such as Type III anodized coating to electrically insulate it without diminishing its heat transfer properties. The conductive block 315 can be heated by a resister or other heating element (e.g. cartridge heater, nichrome wire, etc.) bonded thereto with a heat conductive adhesive, such as epoxy. A thermistor can be coupled to the conductive block 315 with heat conductive epoxy allows temperature monitoring. Other temperature sensors may also be used, such as a thermocouple.

A cladding 320 of conductive material is directly conductively coupled to the proximal portion of the shaft of the needle 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2-100 mm. In some embodiments, the cladding 320 can be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320. The cladding 320 may modify the lateral force required to deflect or bend the needle 26. Cladding 320 may be used to provide a stiffer needle shaft along the proximal end in order to more easily transfer force to the leading tip during placement and allow the distal portion of the needle to deflect more easily when it is dissecting a tissue interface within the body. The stiffness of needle 26 can vary from one end to the other end by other means such as material selection, metal tempering, variation of the inner diameter of the needle 26, or segments of needle shaft joined together end-to-end to form one contiguous needle 26. In some embodiments, increasing the stiffness of the distal portion of the needle 26 can be used to flex the proximal portion of the needle to access difficult treatment sites as in the case of upper limb spasticity where bending of the needle outside the body may be used to access a target peripheral nerve along the desired tissue plane.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer or metal coating can cover the cladding to promote biocompatibility of an otherwise non-biocompatible but highly conductive cladding material. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

In use, the cladding 320 can transfer heat to the proximal portion of the needle 302 to prevent directly surrounding tissue from dropping to cryogenic temperatures. Protection can be derived from heating the non-targeting tissue during a cooling procedure, and in some embodiments before the procedure as well. The mechanism of protection may be providing heat to pressurized cryogenic cooling fluid passing within the proximal portion of the needle to affect complete vaporization of the fluid. Thus, the non-target tissue in contact with the proximal portion of the needle shaft 302 does not need to supply heat, as opposed to target tissue in contact with the distal region of the needle shaft 302. To help further this effect, in some embodiments the cladding 320 is coating within the interior of the distal portion of the needle, with or without an exterior cladding. To additionally help further this effect, in some embodiments, the distal portion of the needle can be thermally isolated from the proximal portion by a junction, such as a ceramic junction. While in some further embodiments, the entirety of the proximal portion is constructed from a more conductive material than the distal portion.

In use, it has been determined experimentally that the cladding 320 can help limit formation of a cooling zone to the distal portion of the needle shaft 302, which tends to demarcate at a distal end of the cladding 320. Accordingly, cooling zones are formed only about the distal portions of the needles. Thus, non-target tissue in direct contact with proximal needle shafts remain protected from effects of cryogenic temperatures. Such effects can include discoloration and blistering of the skin. Such cooling zones may be associated with a particular physical reaction, such as the formation of an ice-ball, or with a particular temperature required to therapeutically affect the tissue therein.

Standard stainless steel needles and gold clad steel needles were tested in porcine muscle and fat. Temperatures were recorded measured 2 mm from the proximal end of the needle shafts, about where the cladding distally terminates, and at the distal tip of the needles. Temperatures for clad needles were dramatically warmer at the 2 mm point versus the unclad needles, and did not drop below 4° C. The 2 mm points of the standard stainless steel needles almost equalize in temperature with the distal tip at temperatures below 0° C.

Figure 3D:
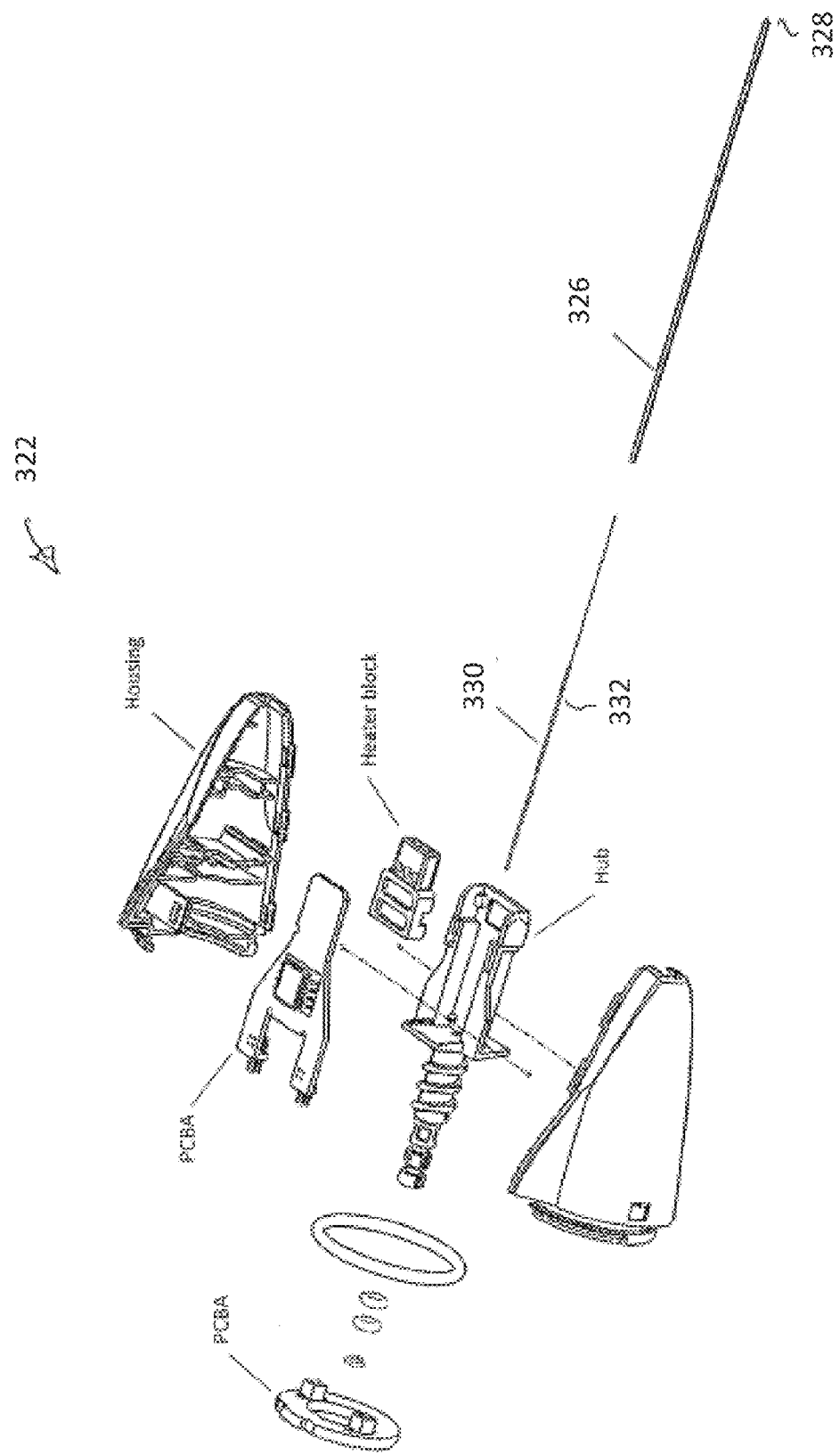

FIGS. 3C and 3D illustrates a detachable probe tip 322 having a hub connector 324 and an elongated probe 326. The probe tip 322 shares much of its construction with probe 300. However, the elongated probe 326 features a blunt tip 328 that is adapted for blunt dissection of tissue. The blunt tip 328 can feature a full radius tip, less than a full radius tip, or conical tip. In some embodiments, a dulled or truncated needle is used. The elongated probe 326 can be greater than 20 gauge in size, and in some embodiments range in size from 25-30 gauge. As with the embodiments described above, an internal supply tube 330 extends in cantilever. However, the exit of the supply tube 330 can be disposed at positions within the elongated probe 326 other than proximate the blunt tip 328. Further, the supply tube 330 can be adapted to create an elongated zone of cooling, e.g., by having multiple exit points for cryofluid to exit from.

The elongated probe 326 and supply tube 330 may be configured to resiliently bend in use, throughout their length at angles approaching 120°, with a 5-10 mm bend radius. This may be very challenging considering the small sizes of the elongated probe 326 and supply tube 330, and also considering that the supply tube 330 is often constructed from fused silica. Accordingly, the elongated probe 326 can be constructed from a resilient material, such as stainless steel, and of a particular diameter and wall thickness [0.004 to 1.0 mm], such that the elongated probe in combination with the supply tube 330 is not overly resilient so as to overtly resist manipulation, but sufficiently strong so as to prevent kinking that can result in coolant escaping. For example, the elongated probe can be 15 gauge or smaller in diameter, even ranging from 20-30 gauge in diameter. The elongated probe can have a very disparate length to diameter ratio, for example, the elongated probe can be greater than 30 mm in length, and in some cases range from 30-100 mm in length. To further the aforementioned goals, the supply tube 330 can include a polymer coating 332, such as a polyimide coating that terminates approximately halfway down its length, to resist kinking and aid in resiliency. The polymer coating 332 can be a secondary coating over a primary polyimide coating that extends fully along the supply tube. However, it should be understood that the coating is not limited to polyimide, and other suitable materials can be used. In some embodiments, the flexibility of the elongated probe 326 will vary from the proximal end to the distal end. For example, by creating certain portions that have more or less flexibility than others. This may be done, for example, by modifying wall thickness, adding material (such as the cladding discussed above), and/or heat treating certain portions of the elongated probe 326 and/or supply tube 330. For example, decreasing the flexibility of elongated probe 326 along the proximal end can improve the transfer of force from the hand piece to the elongated probe end for better feel and easier tip placement for treatment. The elongated probe and supply line 330 are may be configured to resiliently bend in use to different degrees along the length at angles approaching 120°, with a varying bend radius as small as 5 mm. In some embodiments, the elongated probe 326 will have external markings along the needle shaft indicating the length of needle inserted into the tissue.

Figure 3E:
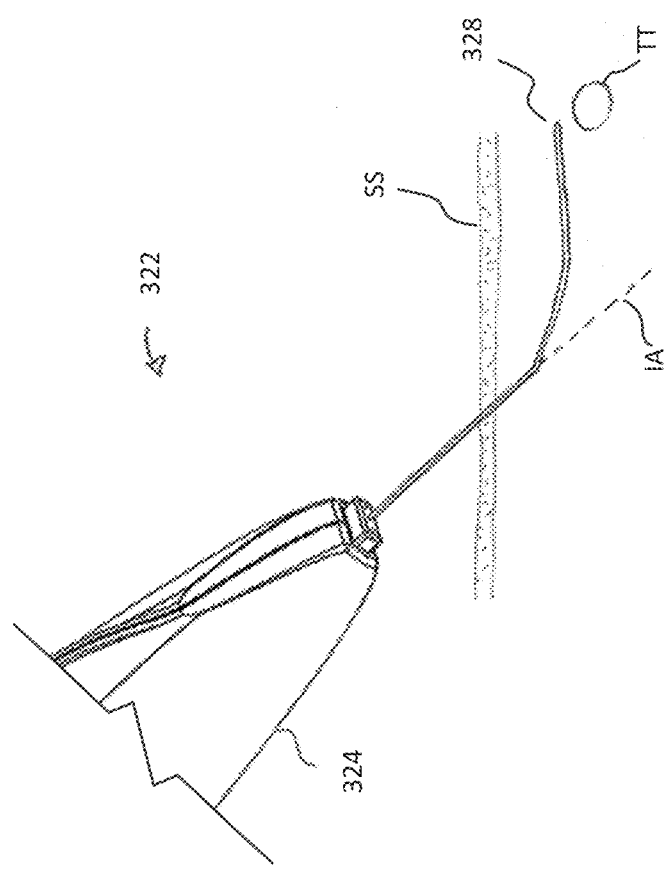

FIG. 3E illustrates an exemplary detachable probe tip 322 inserted through skin surface SS. As illustrated, the probe tip 322 is inserted along an insertion axis IA through the skin surface SS. Thereafter, the needle may be bent away from the insertion axis IA and advanced toward a target tissue TT in order to position blunt tip 328 adjacent to the target tissue TT. In some embodiments, the target tissue may be the infrapatellar branch of the saphenous nerve. In other embodiments the target tissue may be one or more branches of the anterior femoral cutaneous nerve or the lateral femoral cutaneous nerve.

In some embodiments, the probe tip 322 does not include a heating element, such as the heater described with reference to probe 300, since the effective treating portion of the elongated probe 326 (i.e., the area of the elongated probe where a cooling zone emanates from) is well laterally displaced from the hub connector 324 and elongated probe proximal junction. Embodiments of the supply tube are further described below and within commonly assigned U.S. Pub. No. 2012/0089211, which is incorporated by reference.

Figure 4A:
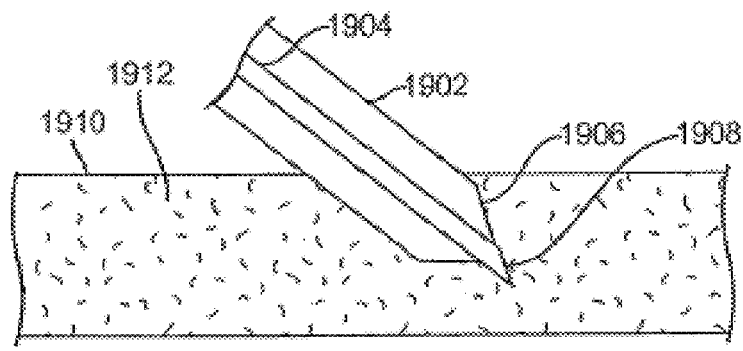
FIGS. 4A-4C illustrate an exemplary method of introducing a cryogenic probe to a treatment area, according to some embodiments of the invention.
Figure 4B:
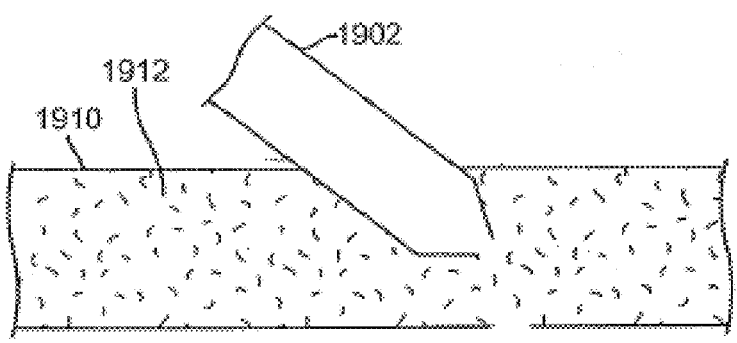
Figure 4C:
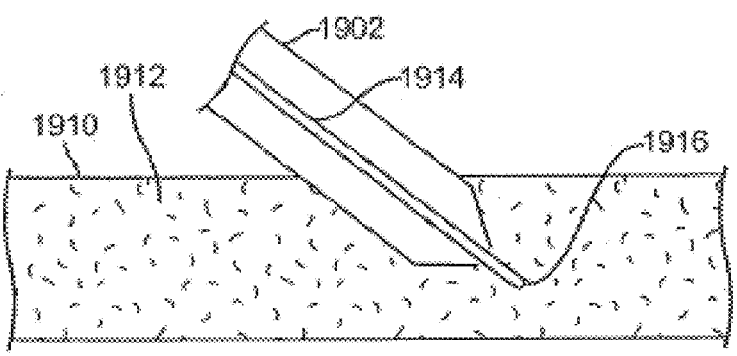

FIGS. 4A-4C illustrate an exemplary method of creating a hole through the skin that allows multiple insertions and positioning of a cryoprobe therethrough. In FIG. 4A a cannula or sheath 1902 is disposed over a needle 1904 having a tissue penetrating distal end 1908. The cannula may have a tapered distal portion 1906 to help spread and dilate the skin during insertion. The needle/sheath assembly is then advanced into and pierces the skin 1910 into the desired target tissue 1912. The inner pathway of the cannula or sheath 1902 may be curved to assist in directing the flexible needle 1904, or other probe, into a desired tissue layer coincident with the desired needle path in the tissue. Once the needle/sheath assembly has been advanced to a desired location, the needle 1904 may be proximally retracted and removed from the sheath 1902. The sheath now may be used as an easy way of introducing a cryoprobe through the skin without piercing it, and directing the cryoprobe to the desired target treatment area. FIG. 4B shows the sheath 1902 in position with the needle 1904 removed. FIG. 4C shows insertion of a cryoprobe 1914 into the sheath such that a blunt tip 1916 of the cryoprobe 1914 is adjacent the target treatment tissue. The cryoprobe may then be cooled and the treatment tissue cooled to achieve any of the cosmetic or therapeutic effects discussed above. In this embodiment, the cryoprobe preferably has a blunt tip 1916 in order to minimize tissue trauma. In other embodiments, the tip may be sharp and be adapted to penetrate tissue, or it may be round and spherical. The cryoprobe 1914 may then be at least partially refracted from the sheath 1902 and/or rotated and then re-advanced to the same or different depth and repositioned in sheath 1902 so that the tip engages a different portion of the target treatment tissue without requiring an additional piercing of the skin. The probe angle relative to the tissue may also be adjusted, and the cryoprobe may be advanced and retracted multiple times through the sheath so that the entire target tissue is cryogenically treated.

While the embodiment of FIGS. 4A-4C illustrates a cryoprobe having only a single probe, the cryoprobe may have an array of probes. Any of the cryoprobes described above may be used with an appropriately sized sheath. In some embodiments, the cryoprobe comprises a linear or two dimensional array of probes. Lidocaine or other local anesthetics may be used during insertion of the sheath or cryoprobe in order to minimize patient discomfort. The angle of insertion for the sheath may be anywhere from 0 to 180 degrees relative to the skin surface, and in specific embodiments is 15 to 45 degrees. The sheath may be inserted at any depth, but in specific embodiments of treating lines/wrinkles of the face, the sheath may be inserted to a depth of 1 mm to 10 mm, and more preferably to a depth of 2 mm to 5 mm.

Figure 4D:
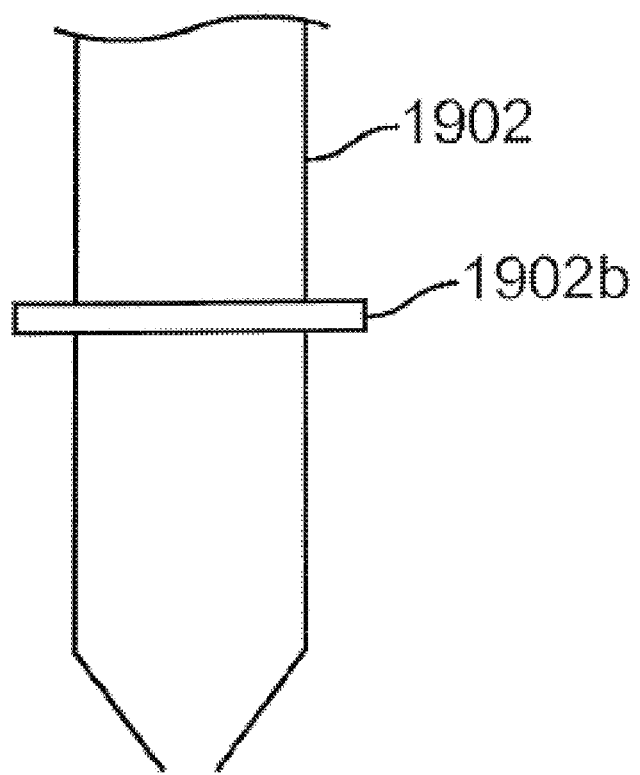
FIG. 4D illustrates an alternative exemplary embodiment of a sheath, according to some embodiments of the invention.

In an alternative embodiment seen in FIG. 4D, the sheath 1902 may include an annular flange 1902b on an outside surface of the sheath in order to serve as a stop so that the sheath is only inserted a preset amount into the tissue. The position of the flange 1902b may be adjustable or fixed. The proximal end of the sheath in this embodiment, or any of the other sheath embodiments may also include a one way valve such as a hemostasis valve to prevent backflow of blood or other fluids that may exit the sheath. The sheath may also insulate a portion of the cryoprobe and prevent or minimize cooling of unwanted regions of tissue.

Figure 5:
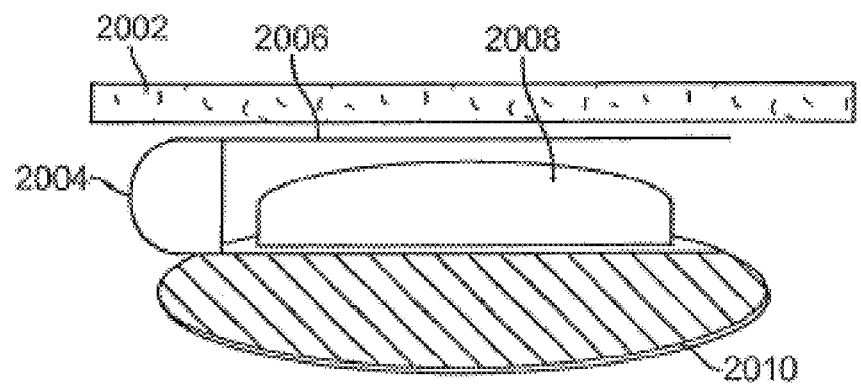
FIG. 5 illustrates an exemplary insulated cryoprobe, according to some embodiments of the invention.

Any of the cryoprobes described above may be used with the sheath embodiment described above (e.g. in FIGS. 3B, 4A-4C). Other cryoprobes may also be used with this sheath embodiment, or they may be used alone, in multi-probe arrays, or combined with other treatments. For example, a portion of the cryoprobe 2006 may be insulated as seen in FIG. 5. Cryoprobe 2006 includes a blunt tip 2004 with an insulated section 2008 of the probe. Thus, when the cryoprobe is disposed in the treatment tissue under the skin 2002 and cooled, the cryoprobe preferentially creates a cooling zone along one side while the other side remains uncooled, or only experiences limited cooling. For example, in FIG. 5, the cooling zone 2010 is limited to a region below the cryoprobe 2006, while the region above the cryoprobe and below the skin 2002 remain unaffected by the cooling.

Figure 6:
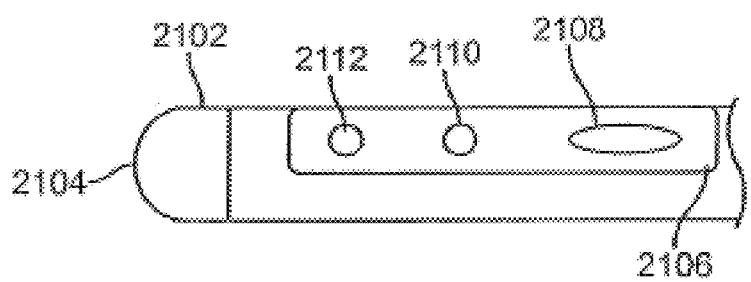
FIGS. 6-9 illustrate exemplary embodiments of cryofluid delivery tubes, according to some embodiments of the invention.
Figure 7:
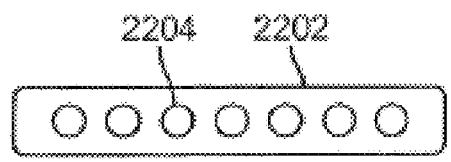
Figure 8:
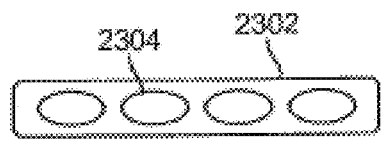
Figure 9:
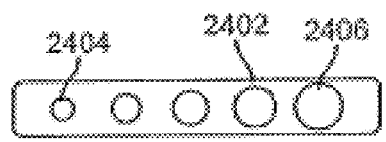

Different zones of cryotherapy may also be created by different geometries of the coolant fluid supply tube that is disposed in the cryoprobe. FIGS. 6-9 illustrate exemplary embodiments of different coolant fluid supply tubes. In FIG. 6 the coolant fluid supply tube 2106 is offset from the central axis of a cryoprobe 2102 having a blunt tip 2104. Additionally, the coolant fluid supply tube 2106 includes several exit ports for the coolant including circular ports 2110, 2112 near the distal end of the coolant fluid supply tube and an elliptical port 2108 proximal of the other ports. These ports may be arranged in varying sizes, and varying geometries in order to control the flow of cryofluid which in turn controls probe cooling of the target tissue. FIG. 7 illustrates an alternative embodiment of a coolant fluid supply tube 2202 having a plurality of circular ports 2204 for controlling cryofluid flow. FIG. 8 illustrates yet another embodiment of a coolant fluid supply tube 2302 having a plurality of elliptical holes 2304, and FIG. 9 shows still another embodiment of a coolant fluid supply tube 2402 having a plurality of ports ranging from smaller diameter circular holes 2404 near the distal end of the supply tube 2402 to larger diameter circular holes 2406 that are more proximally located on the supply tube 2402.

Figure 10:
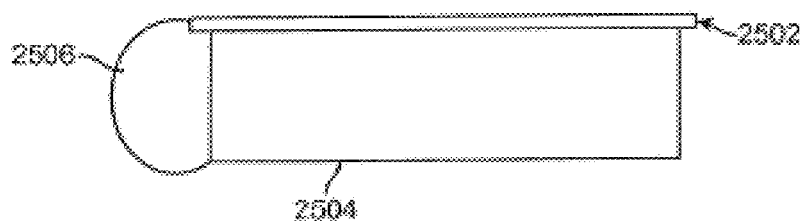
FIG. 10 illustrates an example of blunt tipped cryoprobe, according to some embodiments of the invention.

As discussed above, it may be preferable to have a blunt tip on the distal end of the cryoprobe in order to minimize tissue trauma. The blunt tip may be formed by rounding off the distal end of the probe, or a bladder or balloon 2506 may be placed on the distal portion of the probe 2504 as seen in FIG. 10. A filling tube or inflation lumen 2502 may be integral with or separate from the cryoprobe 2504, and may be used to deliver fluid to the balloon to fill the balloon 2506 up to form the atraumatic tip.

Figure 11:
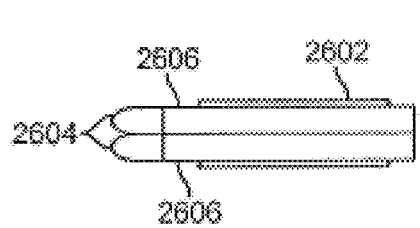
FIGS. 11 and 12 illustrate exemplary actuatable cryoprobes, according to some embodiments of the invention.
Figure 12:
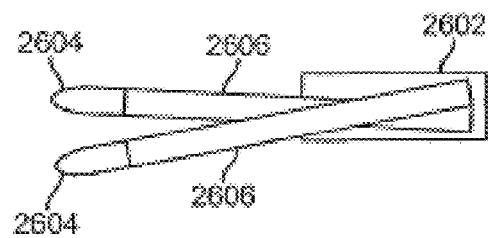

In some instances, it may be desirable to provide expandable cryoprobes that can treat different target tissues or accommodate different anatomies. For example, in FIGS. 11 and 12, a pair of cryoprobes 2606 with blunt tips 2604 may be delivered in parallel with one another and in a low profile through a sheath 2602 to the treatment area. Once delivered, the probes may be actuated to separate the tips 2604 from one another, thereby increasing the cooling zone. After the cryotherapy has been administered, the probes may be collapsed back into their low profile configuration, and retracted from the sheath.

In some embodiments, the probe may have a sharp tissue piercing distal tip, and in other embodiments, the probe may have a blunt tip for minimizing tissue trauma. To navigate through tissue, it may be desirable to have a certain column strength for the probe in order to avoid bending, buckling or splaying, especially when the probe comprises two or more probes in an array. One exemplary embodiment may utilize a variable stiff portion of a sleeve along the probe body to provide additional column strength for pushing the probe through tissue.

Figure 13:
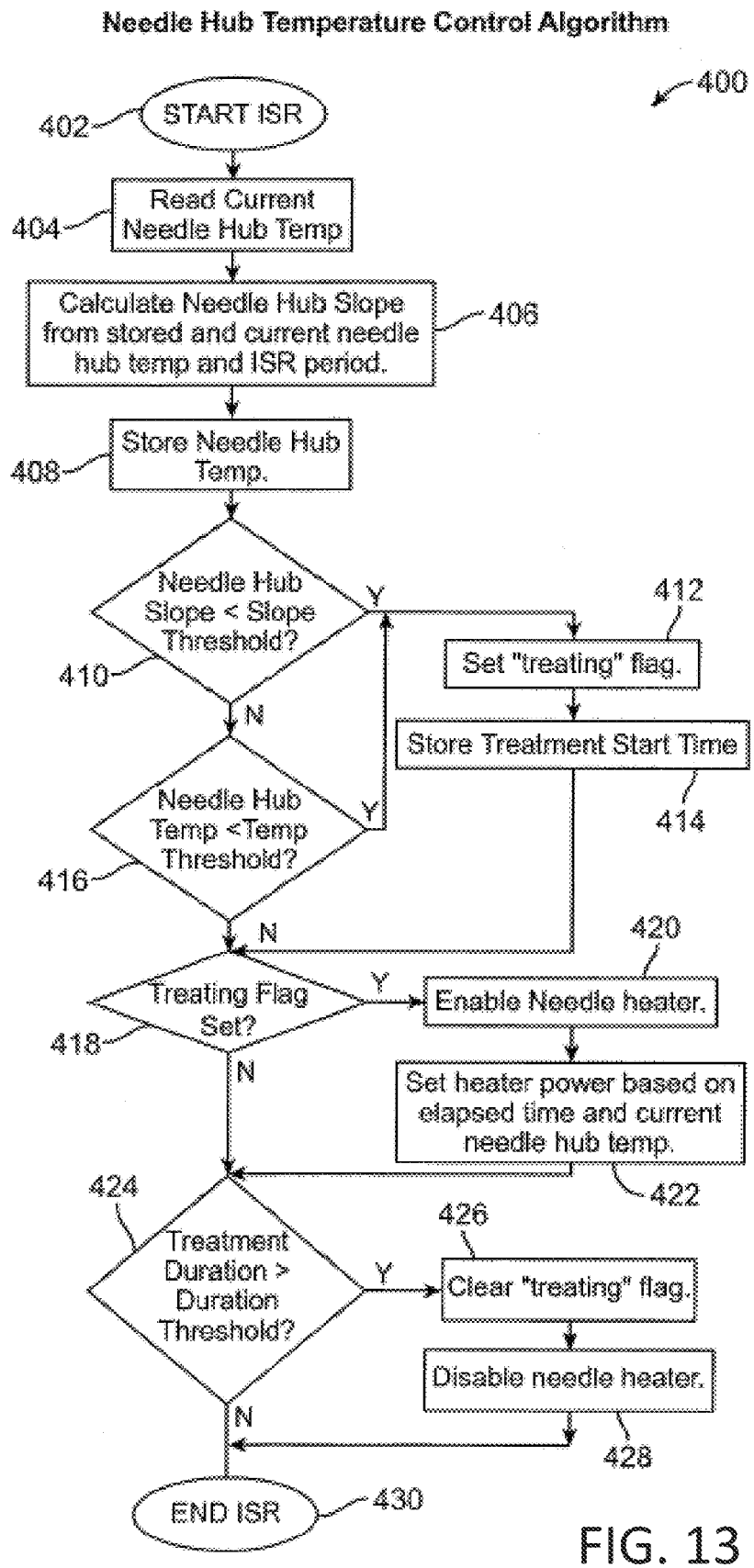
FIG. 13 is a flow chart illustrating an exemplary algorithm for heating the needle probe of FIG. 3A, according to some embodiment of the invention.

An exemplary algorithm 400 for controlling the heater element 314, and thus for transferring heat to the cladding 320, is illustrated in FIG. 13. In FIG. 13, the start of the interrupt service routine (ISR) 402 begins with reading the current needle hub temperature 404 using a temperature sensor such as a thermistor or thermocouple disposed near the needle hub. The time of the measurement is also recorded. This data is fed back to controller 22 where the slope of a line connecting two points is calculated. The first point in the line is defined by the current needle hub temperature and time of its measurement and the second point consists of a previous needle hub temperature measurement and its time of measurement. Once the slope of the needle hub temperature curve has been calculated 406, it is also stored 408 along with the time and temperature data. The needle hub temperature slope is then compared with a slope threshold value 410. If the needle hub temperature slope is less than the threshold value then a treating flag is activated 412 and the treatment start time is noted and stored 414. If the needle hub slope is greater than or equal to the slope threshold value 410, an optional secondary check 416 may be used to verify that cooling has not been initiated. In step 416, absolute needle hub temperature is compared to a temperature threshold. If the hub temperature is less than the temperature threshold, then the treating flag is activated 412 and the treatment start time is recorded 414 as previously described. As an alternative, the shape of the slope could be compared to a norm, and an error flag could be activated for an out of norm condition. Such a condition could indicate the system was not heating or cooling sufficiently. The error flag could trigger an automatic stop to the treatment with an error indicator light. Identifying the potential error condition and possibly stopping the treatment may prevent damage to the proximal tissue in the form of too much heat, or too much cooling to the tissue. The algorithm preferably uses the slope comparison as the trigger to activate the treatment flag because it is more sensitive to cooling conditions when the cryogenic device is being used rather than simply measuring absolute temperature. For example, a needle probe exposed to a cold environment would gradually cool the needle down and this could trigger the heater to turn on even though no cryogenic cooling treatment was being conducted. The slope more accurately captures rapid decreases in needle temperature as are typically seen during cryogenic treatments.

When the treatment flag is activated 418 the needle heater is enabled 420 and heater power may be adjusted based on the elapsed treatment time and current needle hub temperature 422. Thus, if more heat is required, power is increased and if less heat is required, power is decreased. Whether the treatment flag is activated or not, as an additional safety mechanism, treatment duration may be used to control the heater element 424. As mentioned above, eventually, cryogenic cooling of the needle will overcome the effects of the heater element. In that case, it would be desirable to discontinue the cooling treatment so that the proximal region of the probe does not become too cold and cause skin damage. Therefore, treatment duration is compared to a duration threshold value in step 424. If treatment duration exceeds the duration threshold then the treatment flag is cleared or deactivated 426 and the needle heater is deactivated 428. If the duration has not exceeded the duration threshold 424 then the interrupt service routine ends 430. The algorithm then begins again from the start step 402. This process continues as long as the cryogenic device is turned on.

Preferred ranges for the slope threshold value may range from about −5° C. per second to about −90° C. per second and more preferably range from about −30° C. per second to about −57° C. per second. Preferred ranges for the temperature threshold value may range from about 15° C. to about 0° C., and more preferably may range from about 0° C. to about 10° C. Treatment duration threshold may range from about 15 seconds to about 75 seconds.

It should be appreciated that the specific steps illustrated in FIG. 13 provide a particular method of heating a cryogenic probe, according to an embodiment of the present invention. Other sequences of steps may also be performed according to alternative embodiments. For example, alternative embodiments of the present invention may perform the steps outlined above in a different order. Moreover, the individual steps illustrated in FIG. 13 may include multiple sub-steps that may be performed in various sequences as appropriate to the individual step. Furthermore, additional steps may be added or removed depending on the particular applications.

Figure 14:
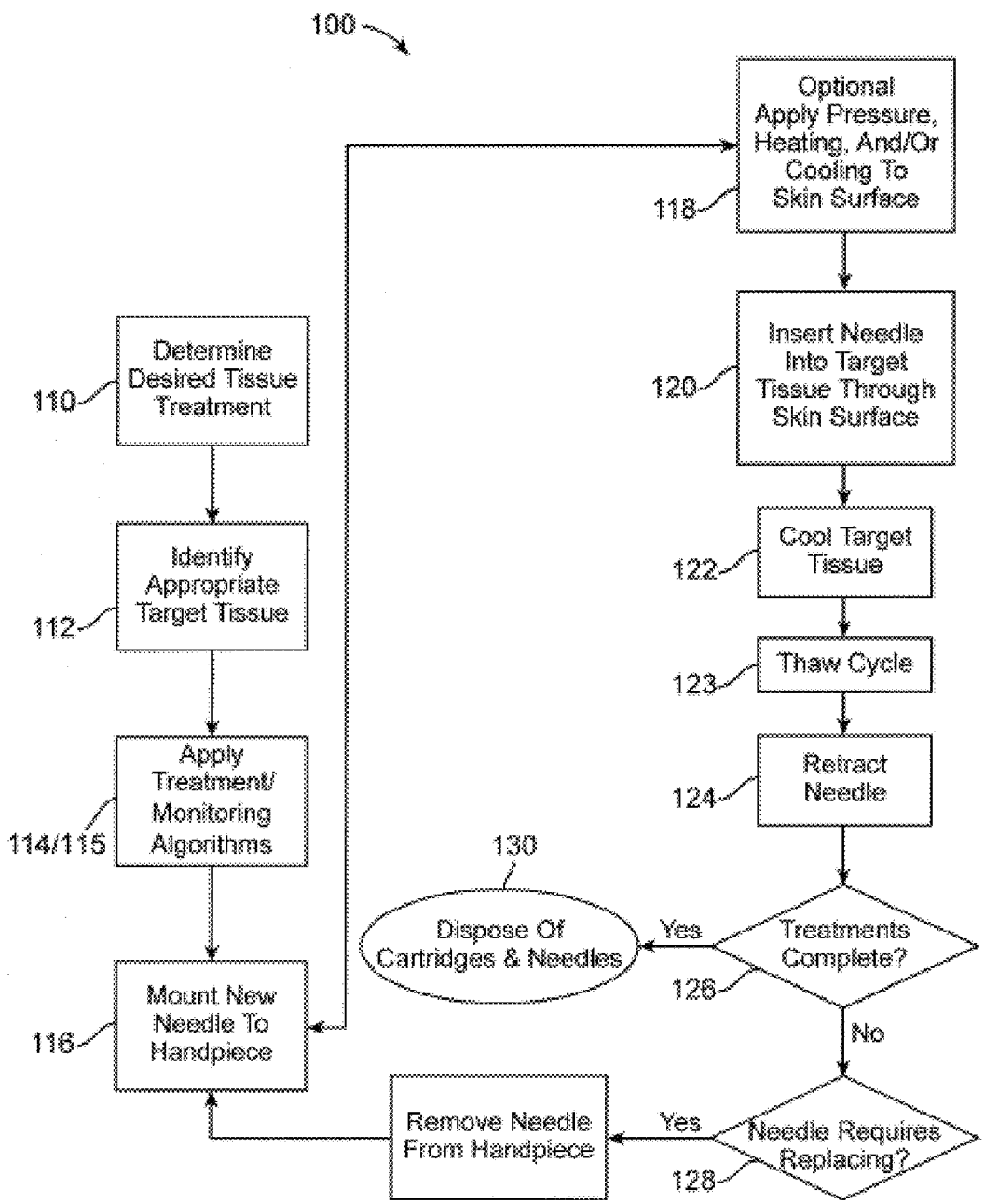
FIG. 14 is a flow chart schematically illustrating an exemplary method for treatment using the disposable cryogenic probe and system of FIGS. 1A and 1B, according to some embodiments of the invention.

The heating algorithm may be combined with a method for treating a patient. Referring now to FIG. 14, a method 100 facilitates treating a patient using a cryogenic cooling system having a reusable or disposable handpiece either of which that can be self-contained or externally powered with replaceable needles such as those of FIG. 1B and a limited capacity battery or metered electrical supply. Method 100 generally begins with a determination 110 of the desired tissue therapy and results, such as the inhibition of pain from a particular site. Appropriate target tissues for treatment are identified 112 (a tissue that transmits the pain signal), allowing a target treatment depth, target treatment temperature profile, or the like to be determined. Step 112 may include performing a tissue characterization and/or device diagnostic algorithm, based on power draw of system 10, for example.

The application of the treatment algorithm 114 may include the control of multiple parameters such as temperature, time, cycling, pulsing, and ramp rates for cooling or thawing of treatment areas. In parallel with the treatment algorithm 114, one or more power monitoring algorithms 115 can be implemented. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Non-target tissue directly above the target tissue can be protected by directly conducting energy in the form of heat to the cladding on a proximal portion of the needle shaft during cooling. Upon completion of the cryogenic cooling cycle the needles will need additional "thaw" time 123 to thaw from the internally created cooling zone to allow for safe removal of the probe without physical disruption of the target tissues, which may include, but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Heating of the needle may be used to prevent unwanted skin damage using the apparatus and methods previously described. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded.

As noted above, suitable target tissues can be selected that include a particular sensory nerve associated with pain, for example, such as: Myofascial, Fibromylagia, Lateral and Medial epicondylitis, Llio-hypo/llio-inguinal, Pudendal, Pyriformis, Osteo-Arthritis of the Knee, Patellar Tendonitis, Diabetic neuropathies, Carpal Tunnel, Phantom Limb, Migraine, Trigeminal Neuralgia, Occipital Neuralgia, Shoulder Arthritis, Shoulder Tendonitis, Suprascapular, Failed Back, Sciatica, Facet, Herniated Disc, Sacoiliac, Sciatic, Morton's Neuroma, and Plantar Fasciitis pain.

Figure 15:
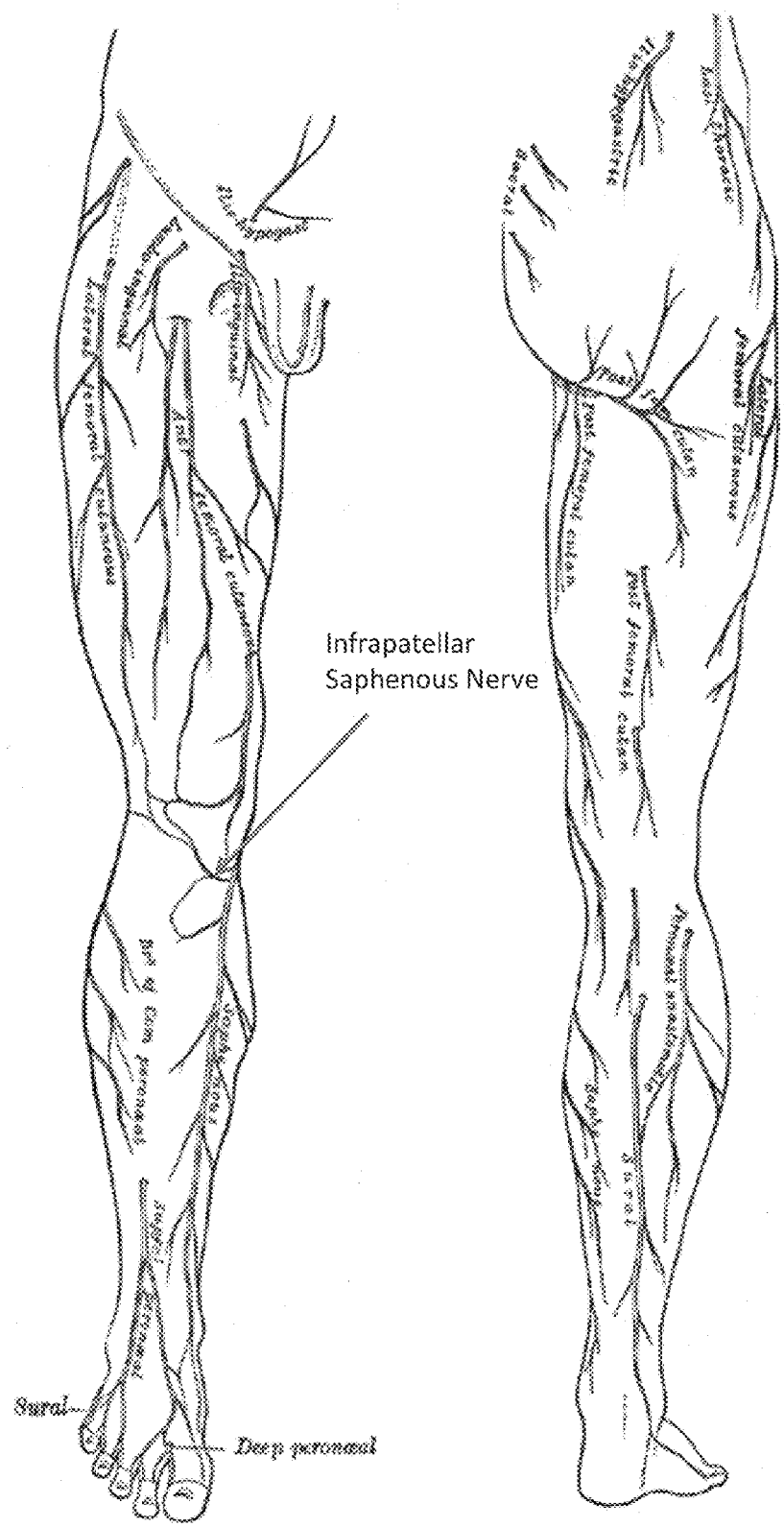
FIG. 15 is an illustration of the infrapatellar branch of a saphenous nerve, according to some embodiments of the invention.

With respect to knee pain, the infrapatellar branch of the saphenous nerve (ISN), illustrated in FIG. 15, may be targeted for treatment according to embodiments of the present invention. In some embodiments of the invention, osteoarthritis of the knee or other painful conditions causing pain in the inferior aspect of the anterior knee may be treated by targeting the infrapatella branch with cooling treatment. Alternatively, or in addition thereto, the anterior femoral cutaneous nerve and/or the lateral femoral cutaneous nerve may be treated to reduce the knee pain experienced by a patient. The saphenous nerve arises as a division of the femoral nerve and leaves the adductor canal between the tendons of gracilis and semitendinosus. It then divides into the main saphenous branch, which continues down to the ankle, and the ISN. The ISN traverses the knee below the patella, dividing into three branches before combining with the anterior branch of the lateral cutaneous nerve of the thigh, the intermediate cutaneous nerves of the thigh and the anterior branch of the medial cutaneous nerve of the thigh to form the prepatella plexus.

Figure 16B:
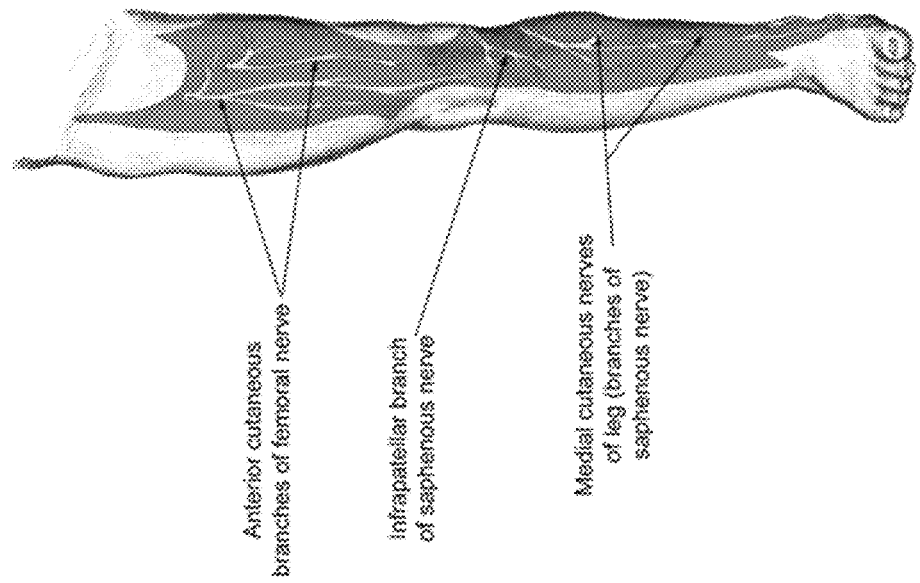
FIG. 16A and FIG. 16B are illustrations of the interconnections of the saphenous nerve.
Figure 16A:
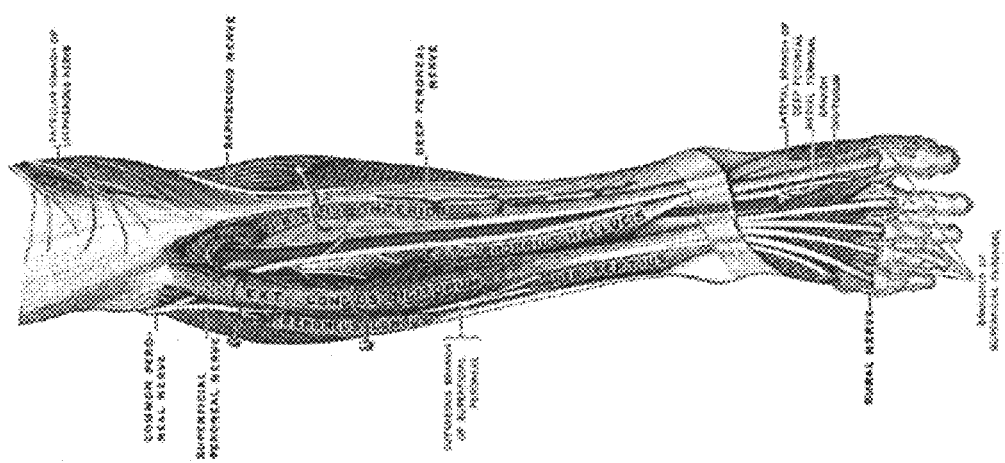

FIG. 16 depicts the interconnections of the saphenous nerve. The saphenous nerve, located about the middle of the thigh, gives off a branch—the ISN—which joins the subsartorial plexus. The ISN pierces the sartorius muscle and fascia lata, and is distributed to the skin in front of the patella. The ISN communicates above the knee with the anterior cutaneous branches of the femoral nerve; below the knee with other branches of the saphenous nerve; and, on the lateral side of the knee, with branches of the lateral femoral cutaneous nerve, forming the plexus patellae. The ISN supplies sensation to the area surrounding and anterior to the knee. Thus, in some embodiments of the present invention, cooling treatments may be provided with the devices and methods disclosed herein to reduce pain sensation in the area of the knee. The anterior femoral cutaneous nerve and the lateral femoral cutaneous nerve may also supply sensation to the area surrounding the knee and may also be treated in some embodiments. In exemplary embodiments, cooling treatments are provided which reduce the pain experienced by osteo-arthritis patients.

Figure 17:
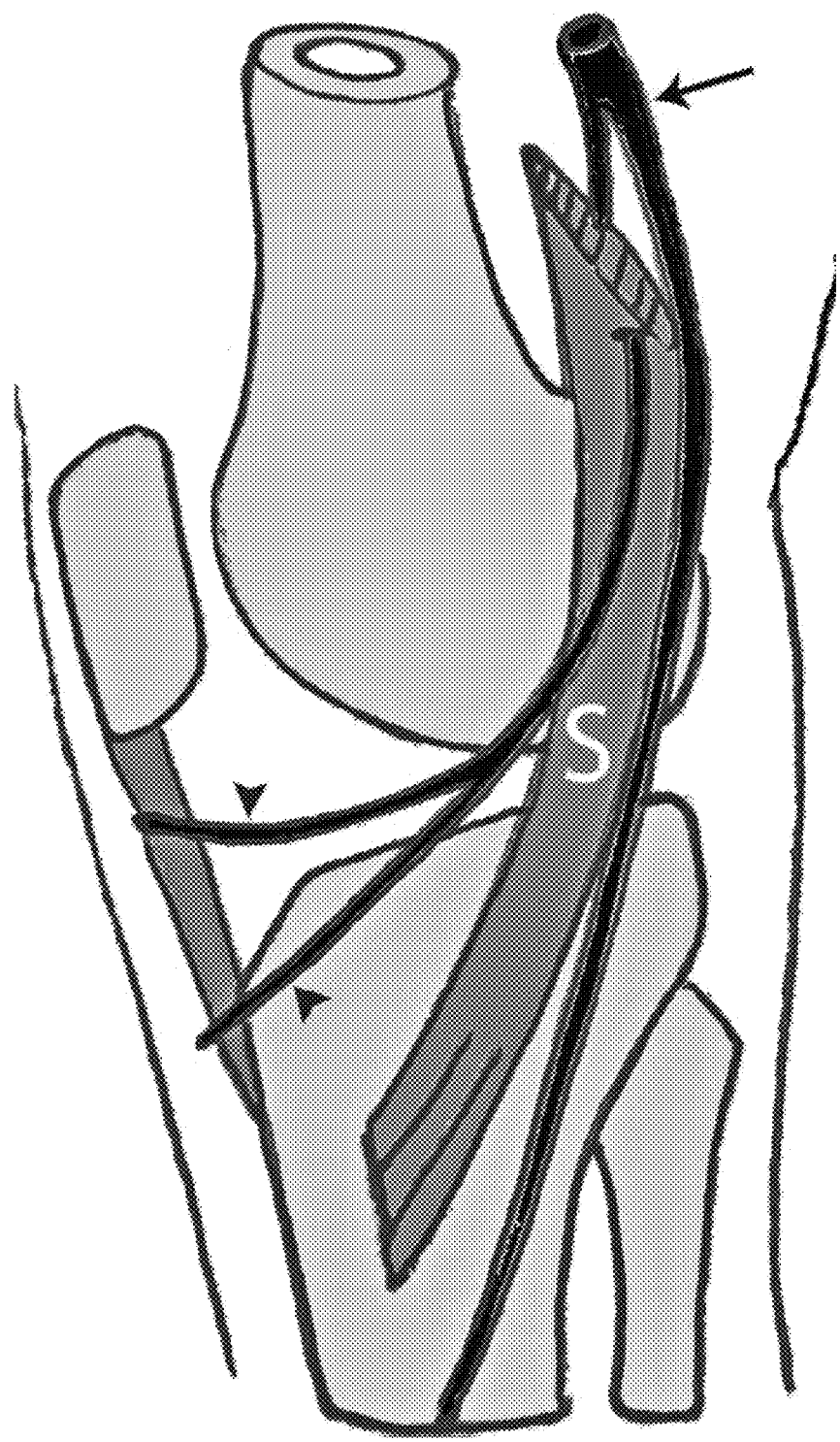
FIG. 17 is another illustration of the interconnections of the saphenous nerve.

FIG. 17 shows an anatomical illustration of the medial aspect of the knee. The figure illustrates the saphenous nerve giving rise to its infrapatella branch in the subartorial canal. The ISN is shown as it pierces the distal sartorius muscle (S) and fascia lata to become subcutaneous. The ISN superficially presents an arc-like course between the apex of the patella cranially and tibial tubercle caudally, and ends in the form of two superior and inferior terminal branches.

Figure 18:
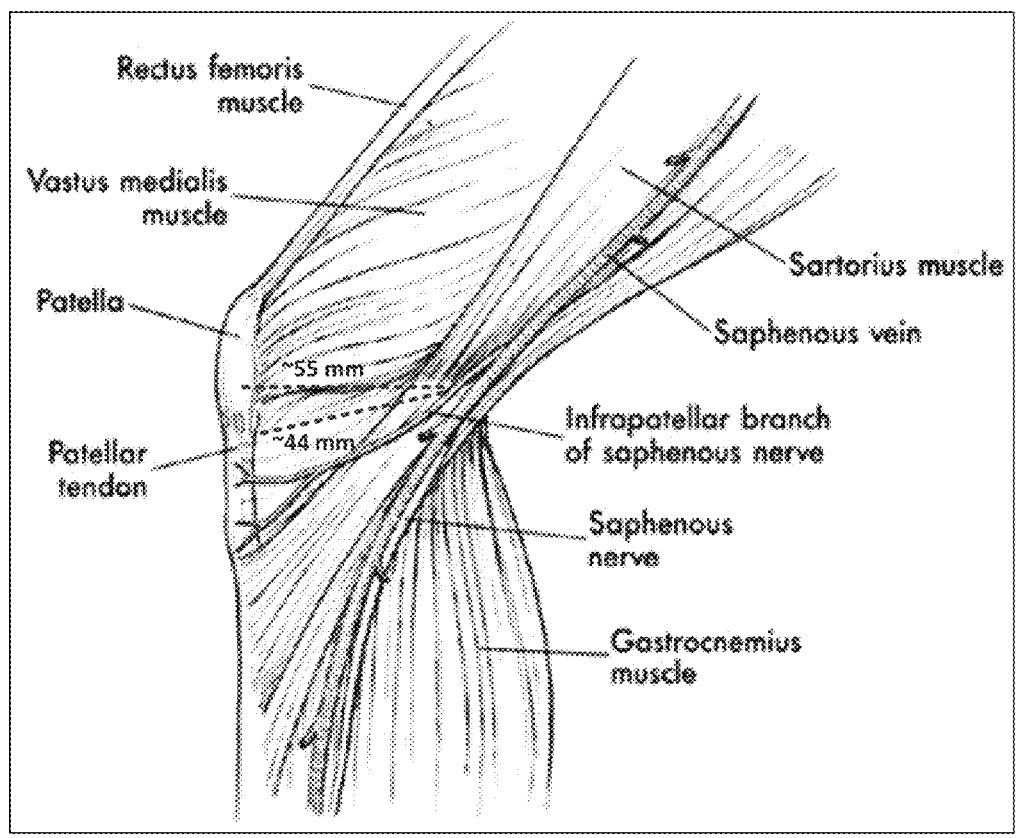
FIG. 18 is an illustration of the position and division of the ISN.

FIG. 18 shows a medial view of the position and division of the ISN. As shown in the medial view of the ISN, the ISN emerges through the fascia lata medial generally at a level with the inferior pole of the patella. Due to patient to patient variation with regards to both nerve location and nerve branching, the ISN branch may occur generally between 46 and 64 mm from, and may occur on average 55 mm from, the medial border of the patella, and may occur generally between 36 and 55 mm from, and may occur on average 44 mm from, the medial border of the patellar tendon. The ISN may then divide into three branches medial to the inferior pole of the patella, anterior to the long saphenous vein. These branches of the ISN are called, the superior branch, the middle branch, and the inferior branch. The Superior Branch runs transversely just inferior to the inferior pole of the patella, ending lateral to the patellar tendon. The Middle Branch divides from the Superior Branch medial to the medial border of the patellar tendon and runs obliquely across the tendon, dividing into its terminal branches at the lateral border. The Inferior Branch is the smallest and runs down in relation to the medial border of the tendon, ending at the level of the tibial tuberosity.

Figure 19:
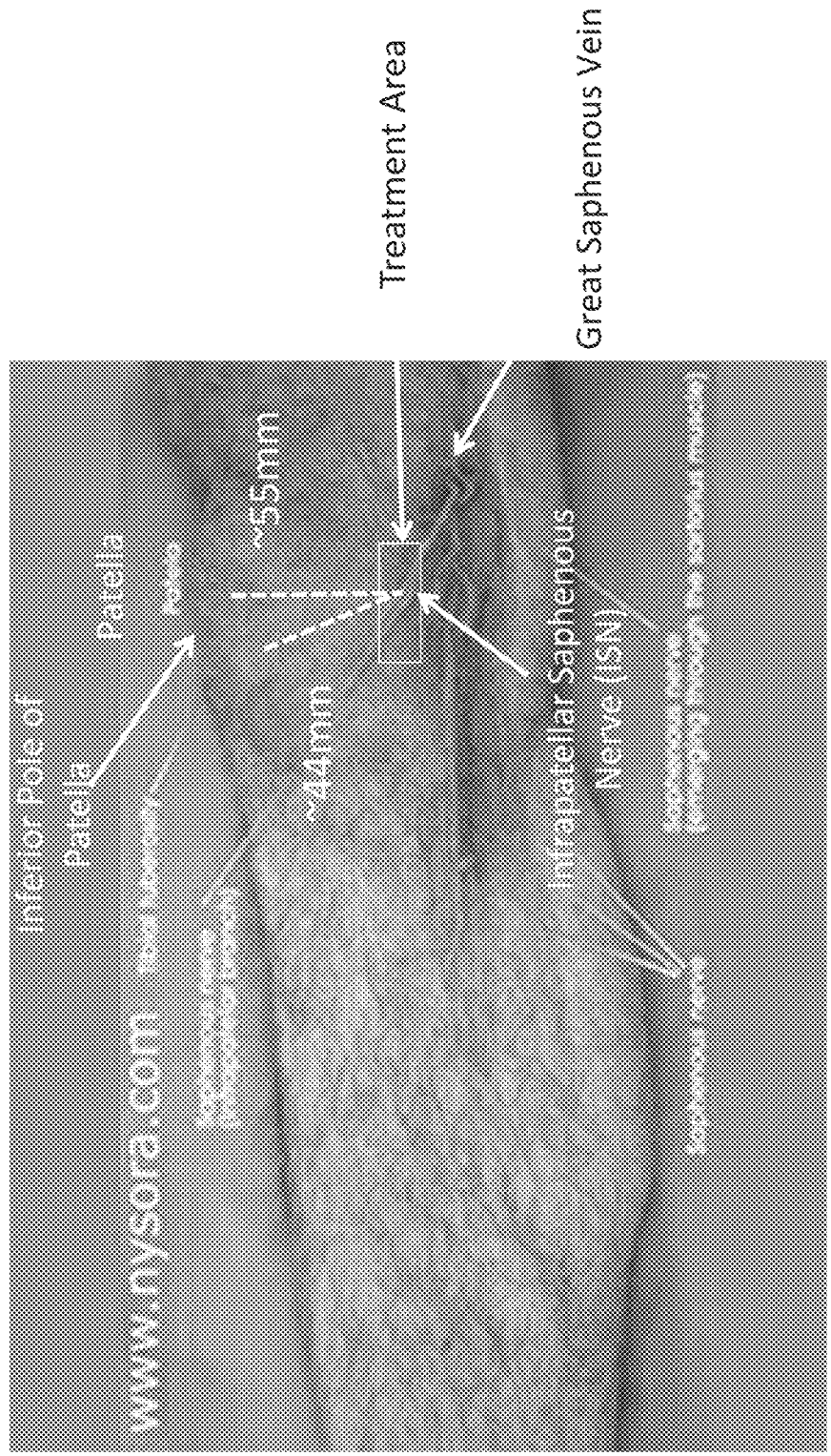
FIG. 19 is an illustration of possible landmarks for locating the ISN and an exemplary treatment zone.

Thus in some embodiments, the ISN may be located relative to key anatomical landmarks. For example, FIG. 19 illustrates exemplary anatomical landmarks for approximating the location of the ISN. In some methods, the ISN may be located or approximated as about 55 mm posterior to the lower pole of the patella. In some methods, the ISN may be located or approximated as about 44 mm posterior to the medial border of the patellar tendon. In some embodiments, the ISN may be located or approximated as about 55 mm from the lower pole of the patella and about 44 mm from the medial border of the patellar tendon. In some embodiments, the ISN position may be approximated based on a location of the great saphenous vein. FIG. 19 also illustrates a treatment area where cooling may be applied to approximate the location of the ISN.

Figure 20:
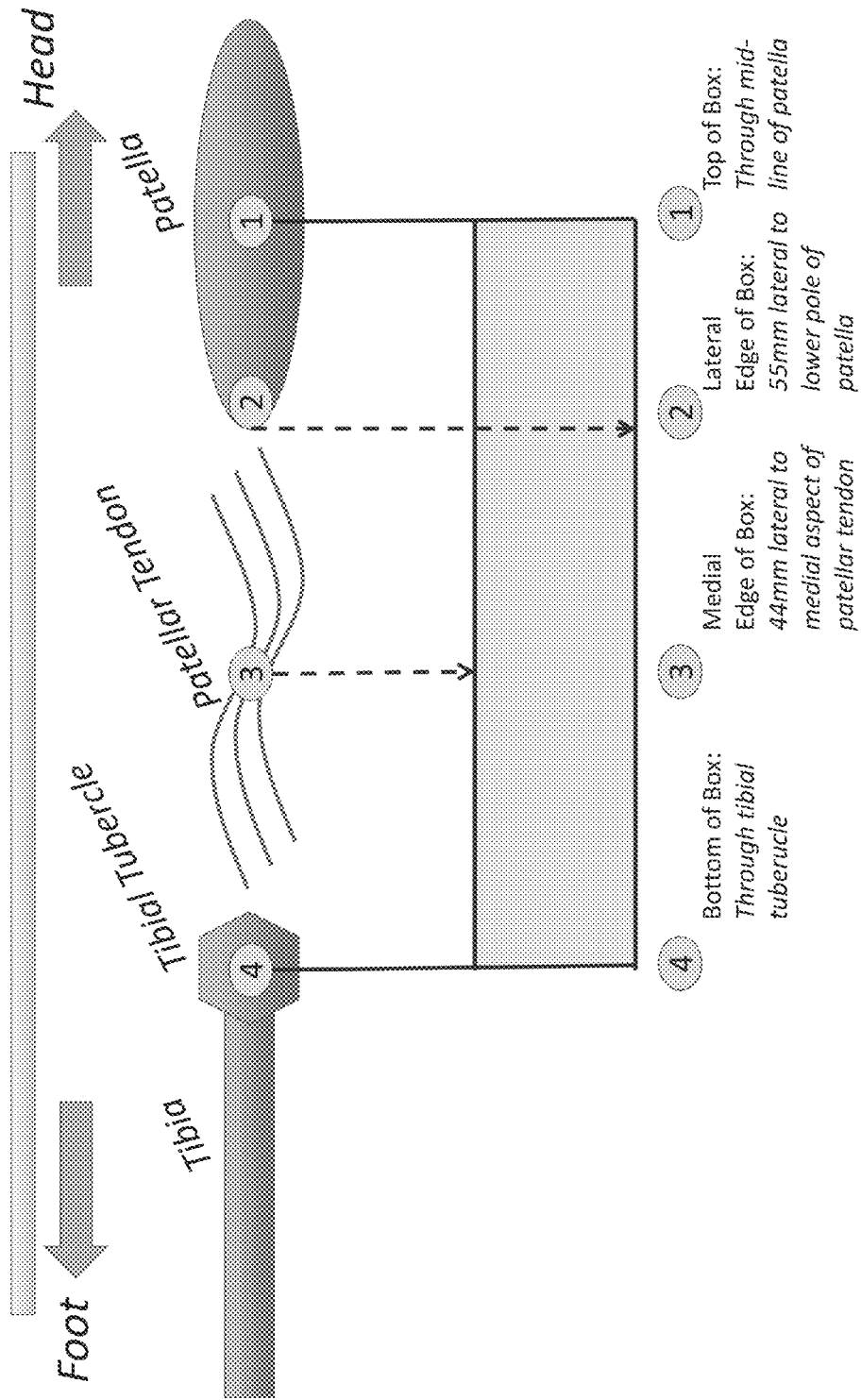
FIG. 20 is an illustration of an exemplary treatment zone according to some embodiments of the present invention.

An example treatment zone is shown in FIG. 20. Here, a treatment zone is shown for treating an infrapatellar branch of a saphenous nerve. The treatment zone is shown as an area defined by four borders. A first boundary (uppermost/superior boundary) of the treatment zone may be defined by the approximate mid-line of the patella. The second boundary (the lateral boundary) of the treatment zone may be defined as about 55-65 mm lateral from the lower pole of the patella. A third boundary (the medial boundary) of the treatment zone may be defined as about 44 mm laterally from the medial aspect of the patellar tendon. A fourth boundary (bottommost/inferior boundary) for the treatment zone may be defined by a line parallel to the first boundary which intersects the tibial tubercule. In some embodiments, the uppermost/superior boundary may be defined by the superior pole of the patella. Optionally, the lateral boundary may be defined as about 65 mm from the center of the patella.

The shown treatment zone can be used to treat the infrapatellar branch of a saphenous nerve with high likelihood of success. In one study, which is discussed below, and shown in FIG. 20, a series of treatments were performed along the second boundary between the first and fourth boundaries and was successful in placing a needle of a cryogenic device into good proximity with the infrapatellar branch, to successfully remodel the infrapatellar branch with a cooling zone generated by the needle. In some cases, treatments can be performed along the third boundary to attain an even higher likelihood of success. The treatments are performed such that each generated cooling zone is directly adjacent, or overlapping with a previously created or concurrently created cooling zone. In some cases, a device, such as the one shown in FIG. 3A, having a plurality of needles is used to treat along the second and/or third boundary. For the sake of redundancy, the treatment zones can overlap, for example, by placing one needle of the plurality of needles in a previously created needle hole, thus linking each treatment. In some embodiments of the invention, a treatment guide or template may be fashioned for facilitating the identification of the infrapatellar branch.

Figure 21A:
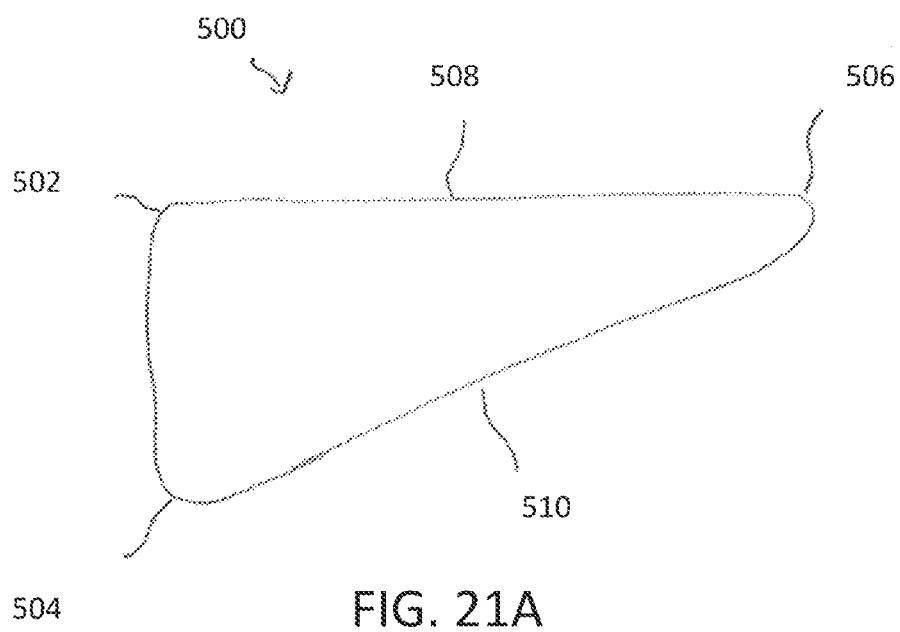
FIG. 21A and FIG. 21B are illustrations of an exemplary treatment template or guide according to some embodiments of the present invention.
Figure 21B:
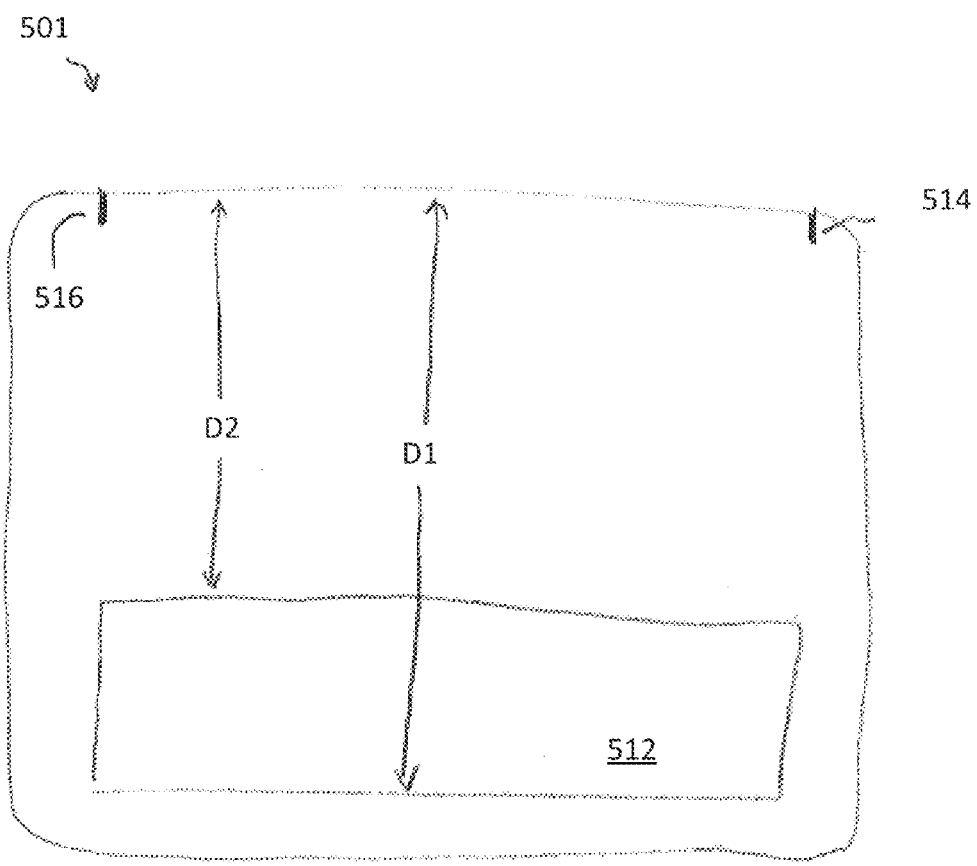

FIG. 21A and FIG. 21B illustrate exemplary guides or templates 500, 501 which may be used to approximate a treatment zone. FIG. 21A illustrates an exemplary guide 500 which may be substantially planar and include a first corner 502, a second corner 504, and a third corner 506. The first corner 502 may be aligned with the lower pole of the patella. The second corner 504 may be aligned with the medial aspect of the patellar tendon. The third corner may then approximate the location of the infrapatellar branch. The third corner 506 may be separated by a first distance 508 from the first corner 502. The first distance 508 may be between 30 and 70 mm. The third corner 506 may also be separated by a second distance 510 from the second corner 504. The second distance 510 may be between 25 and 60 mm. The template 500 may be constructed from thin flexible plastic sheet, and may in some embodiments be transparent. In some embodiments, template 500 includes an adhesive backing for temporarily adhering the template 500 to a skin surface. In some embodiments, the template may contain a transdermal medication, such as anti-inflammatory and anesthesia (e.g., lidocaine) drugs. An example of such construction is shown in U.S. Publication No. 2010/0234471, which discloses lidocain tape and is incorporated herein by reference.

FIG. 21B illustrates another embodiment 501 of a treatment guide or template which may be used for approximating a treatment zone for treating the infrapatellar branch of a patient. The guide 501 includes a window 512 that defines a treatment zone. Guide 501 may also include a first indicia 514 and a second indicia 516. Indicia 514 may be aligned with the midline of the patella for example. Indicia 516 may be aligned with the tibial tubercle. The medial edge of window 512 may be at a first distance D1 and the lateral edge of window 512 may be at a second distance D2. The first distance D1 may be between 30 and 70 mm. The second distance D2 may be between 25 and 60 mm.

A study was performed on 33 human patients for treatment of osteoarthritis of the knee, or symptoms resembling OA, using some embodiments of the present invention. Subjects were prospectively enrolled to treat chronic pain caused by osteoarthritis of the knee. Subjects received either a unilateral or bilateral treatment based on disease state. All subjects completed a minimum follow-up period of 56 days. The purpose of the study was to investigate the effect of the cryogenic cooling therapy devices and methods on sensory nerves in the clinical setting. In this study, thirty-three subjects were enrolled with a diagnosis of osteoarthritis of the knee. Fifty-six knees were treated.

A device similar to the one shown in FIG. 3A was used, i.e., a device having 3 cryogenic needles, with each being approximately 6 mm long. Each needle included a conductive coating, coupled to a heater as described with respect to FIG. 3B, that extended approximately 2 mm down the needle. The system was programmed with a treatment cycle comprising a 10 second pre-warm phase, followed by a 60 second cooling phase, followed thereafter by a 15 second post-warm phase with 40° C. skin warmer throughout. During the pre-warm phase of the treatment cycle, the skin warmer activates and brings the skin warming block to a uniform target temperature. This can take 10 s or longer depending on the size of the skin warming block and the target temperature. Once the skin warmer has achieved the target temperature, the main valve opens and the cooling phase starts. The cooling phase lasts for a predetermined period of time during which a cooling zone forms around the distal end of the needles. When the valve closes and the cooling phase ends, the skin warmer continues to heat allowing the frozen tissue to thaw from around the needles. When the cycle is over the system alerts the user with a visual and an audible cue. Attempting to remove the needles before some thawing has occur can cause injury as the frozen tissue may be adhered to the needles, therefore it may be important to allow a post-warm phase of the cycle. After the treatment cycle is completed, the probe may be removed and inserted inferiorly along the nerve. Typically between four and ten treatments were performed on each knee.

The treatment target was the infrapatellar branch of the saphenous nerve (ISN). It was suggested to the Investigators to use a treatment box shown in FIG. 20 crossing the predicted path of the ISN using anatomical landmarks. The suggested treatment box was drawn with the top of the box as the midpoint of the patella, the bottom of the box as the tibial tubercle, one side of the box at approximately 44 millimeters from the medial border of the patellar tendon, and the other side at approximately 55 millimeters from the medial border of the inferior pole of the patella. The treatments were performed along the second boundary. Treatments typically started at the first boundary and ended at the fourth boundary but sometimes started at the fourth boundary and ended at the first boundary. The cryogenic cooling needle may be inserted into the treatment box treating in a sequential linear fashion forming a line of treatments within the box crossing the predicted nerve path as it passes anteriorly and inferiorly. In this manner a continuous treatment fence was created. In some cases, particularly if the patient still exhibited pain or other sensations associated with osteoarthritis, a second set of treatments also extended across the first boundary. In some cases the starting point along the second boundary was identified using PENS. In some cases the treatment continued along the treatment line until the patient detected a cessation or diminished pain. Cooling zones may be made to overlap to increase the likelihood that the infrapatellar branch of the saphenous nerve was affected, such that second degree nerve injury occurred to instigate Wallerian degeneration.

In some applications, local anesthesia may be injected sub dermally in the treatment box with the goal of complete cutaneous anesthesia. It may be beneficial to apply superficial anesthetic injections so as to numb the skin to reduce the pain associated with the needle insertion without numbing the underlying nerve or target tissue.

In some applications, percutaneous electrical nerve stimulation (PENS) may be used in conjunction with treatment. In the study, PENS was used by one investigator (site 15) for the final 10 of 20 subject treatments. The PENS unit functioned to approximate a more specific location of the infrapatellar branch of the saphenous nerve within the treatment box. The PENS needle was inserted through the skin at the middle of the treatment box, with a setting of 2 Hz, 1.0 ms and 1.0 mA, and moved radially within the skin until the subject reported a pain or sensation within the knee. When sensation occurred, the PENS unit current setting was reduced by 0.2 mA and the PENS needle was advanced deeper to further specify the nerve location. This process was repeated until a minimum amount of current was used (0.2 mA) and a pain or sensation was still felt in the knee. The depth of the needle and general location of the nerve was marked. For these subjects, treatment cycles began at the nerve location approximated by PENS and additional treatment cycles were performed superior and inferior to this location until relief was achieved. Relief was determined using subject feedback (palpation or movement of the kneecap) during treatment. When a subject reported that the pain associated with a specific treatment cycle was worse than the others, it was assumed that the cryogenic cooling needle was on or very close to the target nerve, upon which an additional treatment was performed immediately next to this location until the subject reported no additional sensation during the treatment cycle.

The results of this study were surprising and unexpected, as experts in the field provided professional opinions that the procedure would provide no pain relief. Accordingly, there was no expectation for the level of success demonstrated in the study. The results of the study are summarized in FIGS. 22-26.

The subjects rated knee pain using the Visual Analogue Scale (VAS) from 0 to 10. No pain equals zero and 10 equals very severe pain. The VAS was used by Subjects to assess pain pre-treatment, immediately post-treatment, at Day 7 and at Day 30.

The Western Ontario McMaster Universities Osteoarthritis Index (WOMAC) is a tri-dimensional, disease-specific, patient-reported outcome measure. It consists of 24 questions with 5 questions regarding pain, 2 questions regarding stiffness and 17 questions regarding function. The WOMAC was assessed pre-treatment and Day 7. Duration of treatment was assessed at Day 7, Day 30 and Day 56. At these time points, Subjects were asked if they were having an effect from the treatment. The post-treatment questionnaire included 2 questions regarding subject satisfaction.

Thirty-three subjects were enrolled in the study and 56 knees were treated. Subjects with a diagnosis of osteoarthritis in both knees were eligible for a bilateral treatment. Twenty-three Subjects received bilateral treatment while 10 Subjects received unilateral treatment. Table 1 provides an overview of subject accountability.

TABLE 1

| Status | Site 14 | Site 15 | Total |
|---|---|---|---|
| Enrolled | 13 | 20 | 33 |
| Discontinued - subject withdrawal | 0 | 0 | 0 |
| Discontinued - investigator withdrawal | 0 | 0 | 0 |
| Excluded for Protocol Violation | 0 | 0 | 0 |
| Total Included in Data Analysis | 13 | 20 | 33 |

Subject accountability for all required follow-up visits through Day 56 was 100%. Twenty-two Subjects (38 knees) were followed beyond Day 56 (see Tables 2 and 3). Subjects 15-011 and 15-013 had Day 30 follow-up visits but did not complete the Post-Treatment Questionnaire at this visit; additionally, Subject 15-013 was not assessed for VAS at Day 30. Subject 14-012 had an incomplete Day 56 visit due to coordinator error; the Subject reported on adverse events, changes in concomitant medications and continued effect from treatment but did not complete Post-Treatment Questionnaire or anticipated observations. These deviations are reported below. Table 2 provides an overview of Subject Accountability over follow-up periods.

TABLE 2

| Site ID | Enrolled | Treated | Day 7 | Day 30 | Day 56 | Day 84 | Day 112 | Day 140 | Beyond Day 140 |
|---|---|---|---|---|---|---|---|---|---|
| 14 | 13 | 13 | 13 | 13 | 13 | 6* | 6 | 3 | 2 |
| 15 | 20 | 20 | 20 | 20 | 20 | 13 | 8 | 5 | 2 |

Table 3 provides an overview of Subject Accountability over follow-up period by knees.

TABLE 3

| Site ID | Enrolled | Treated | Day 7 | Day 30 | Day 56 | Day 84 | Day 112 | Day 140 | Beyond Day 140 |
|---|---|---|---|---|---|---|---|---|---|
| 14 | 21 | 21 | 21 | 21 | 21 | 10* | 8 | 4 | 3 |
| 15 | 35 | 35 | 35 | 35 | 35 | 24 | 14 | 9 | 3 |

*Three subjects missed the Day 84 phone call but had Day 112 phone calls. These subjects are not included in the subject accountability for Day 84.

Subjects who continued to demonstrate a treatment effect at Day 56 remained in the study and received follow-up phone calls every 4 weeks to assess treatment effect status until revision 04 of the protocol was approved by the IRB. Subjects were also followed until resolution of clinically significant adverse events as stated in the protocol.

Four Subjects, 2 at each site, were followed beyond 140 days:

2 Subjects (3 knees) were followed through 168 days post-treatment.

One Subject (1 knee) was followed through 196 days post-treatment.

One Subject (1 knee) continued to be followed to 224, 252 and 280 days post-treatment, at which point the Subject was exited with continued treatment effect.

Demographics—

Of the Subjects enrolled, 64% (21/33) were male and 36% (12/33) were female. The average age was 55.9 years old (range 30-82 years old) with a standard deviation 11.6. The average VAS score at baseline was 6.3 (standard deviation 1.6). Demographics are detailed below in Table 4.

TABLE 4

| demographics. | | | | |
|---|---|---|---|---|
| | | Site 14 | Site 15 | Total |
| Gender (% M/% F) | | 62%/38% | 65%/35% | 64%/36% |
| Average age | | 52.4 | 58.3 | 55.9 |
| (Standard deviation, range) | | (8.9, 37-68) | (12.5, 30-82) | (11.6, 30-82) |
| Average baseline VAS | | 6.1 | 6.4 | 6.3 |
| (Standard deviation) | | (1.5) | (1.6) | (1.6) |
| Average baseline WOMAC | Pain | 24.2 (5.9) | 25.7 (10.9) | 25.2 (9.4) |
| | Stiffness | 11.5 (3.0) | 12.0 (3.8) | 11.8 (3.5) |
| | Function | 89.7 (17.4) | 88.3 (37.1) | 88.8 (31.2) |
| (Standard deviation) | Overall | 125.4 (24.1) | 126.1 (50.8) | 125.8 (42.8) |

VAS and WOMAC scores were analyzed for response rates, clinically important differences and statistically significant improvements from baseline at each follow-up point. Duration of treatment effect was analyzed for number of responders at each follow-up point. All averages calculated include the standard deviation parenthetically to better describe the statistical outcomes of this analysis.

VAS Score—

Figure 22A:
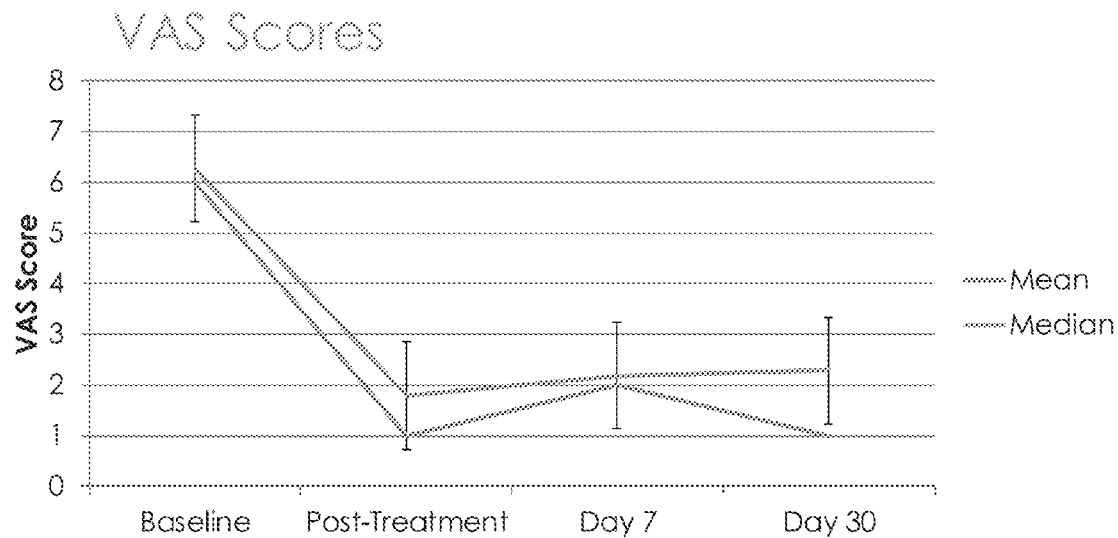
FIG. 22A is a chart showing VAS scores over a follow up period.
Figure 22B:
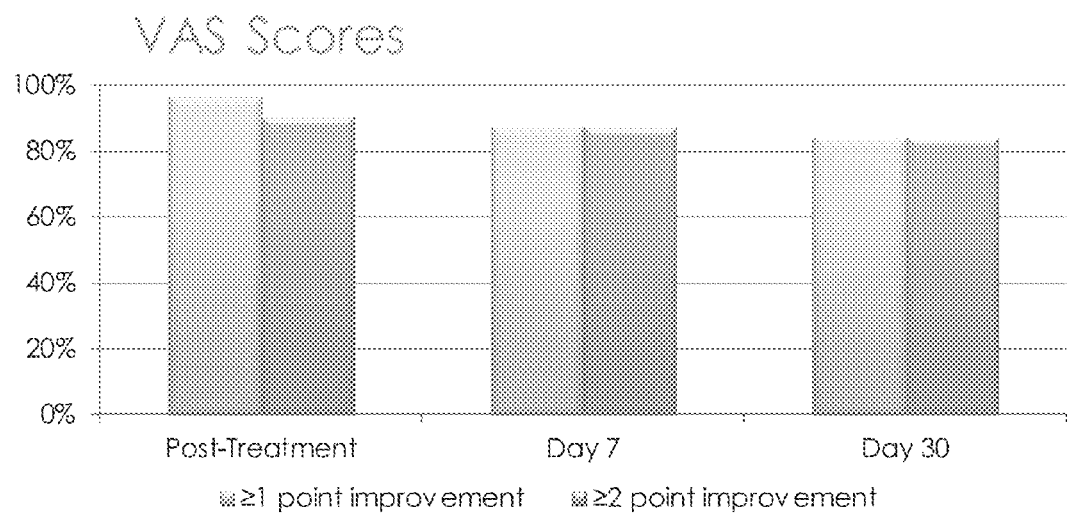
FIG. 22B summarizes VAS score improvement from treatment.

FIGS. 22A-22B summarize the improvement of VAS scores as a result of the treatment. FIG. 22A shows the mean and median VAS scores at the baseline and over the follow-up period (post-treatment, 7 days, and 30 days). Error bars represent the standard error on the mean measurements. FIG. 22B shows the percent of subjects showing 1 and 2 point improvements in VAS scores at post treatment, at the 7 day follow-up, and at the 30 day follow up. Eighty-eight percent (88%) of Subjects reported improvement in VAS at Day 7 (Table 5), the primary endpoint. VAS scores were also assessed post-treatment and again at Day 30, with 97% of subjects reporting improvement in VAS immediately post-treatment and 84% with improvement at Day 30.

TABLE 5

Percent of Subjects with Improvement in VAS Score from Baseline

|  | Post Treatment | Day 7 | Day 30 |
| --- | --- | --- | --- |
| ≥1 point improvement | 97% (32/33) | 88% (29/33) | 84% (27/32) |
| ≥2 point improvement | 91% (30/33) | 88% (29/33) | 84% (27/32) |

A clinically important improvement in VAS has been defined as an improvement of 13 mm on the 0-100 mm scale, corresponding to a 1.3 point improvement on the 0-10 scale used in this study. Therefore, an improvement in VAS of ≥2 points can be considered clinically important. Using this threshold, 91% of subjects showed clinically important improvement post-treatment; this was 88% at Day 7 and 84% at Day 30.

When assessed post-treatment, VAS scores improved by an average of 4.5 points (Table 6), an average of a 73% improvement from baseline. At Day 7, Subjects had an average VAS score improvement of 4.1 points, a 66% improvement from baseline. At Day 30 post-treatment, Subjects had an average VAS score improvement of 4 points, a 64% improvement compared to baseline.

TABLE 6

Average Improvement in VAS Score from Baseline.

|  | Baseline (N = 33) | Post-Treatment (N = 33) | Day 7 (N = 33) | Day 30 (N = 32) |
| --- | --- | --- | --- | --- |
| Average VAS Score | 6.3 | 1.8 | 2.2 | 2.3 |
| (Standard deviation) | (1.6) | (2) | (2.2) | (2.4) |
| Average Point Improvement |  | 4.5 | 4.1 | 4 |
| (Standard deviation) |  | (2.1) | (2.2) | (2.5) |
| Average Percent Improvement |  | 73% | 66% | 64% |
| (Standard deviation) |  | (28%) | (33%) | (35%) |
| P-Value (Significance in change from baseline) |  | 1.36E−13 | 9.52E−12 | 3.33E−10 |

Improvements in VAS scores from baseline to each time point were analyzed for statistical significance using a null hypothesis of $H_O$: Difference=0, where the difference is calculated by subtracting the score at post-treatment, Day 7 and Day 30 from the VAS score reported at baseline. A paired two-tailed t-test was employed to account for the possibility of subjects worsening over the course of the study, and the test was performed using a statistical significance level of P<0.05. The point improvements from baseline at post-treatment, Day 7 and Day 30 were tested against the null hypothesis and produced P-values of 1.36E-13, 9.52E-12, and 3.33E-10, respectively (Table 6). These P-values meet the threshold of statistical significance (P<0.05) and reject the null hypothesis of zero change from baseline. The analysis shows a statistically significant change in the VAS scores from baseline to the follow-up assessments.

WOMAC Score—

Secondary endpoints included 1) an improvement in WOMAC score at Day 7 with a significant difference observed at ≥2 points and 2) duration of treatment effect. WOMAC scores were assessed at baseline and at Day 7, with one WOMAC completed for each knee treated. The index is comprised of three categories including pain, stiffness, and function. Each category contains a set of questions rated by the Subject on a 0-10 scale; pain is comprised of 5 questions, stiffness is comprised of 2 questions and function is comprised of 17 questions. The minimal clinically important difference for improvement in WOMAC score is 0.67 on the 0-10 scale; therefore, an improvement of ≥2 points, as specified in the endpoints, can be considered clinically important.

Figure 23A:
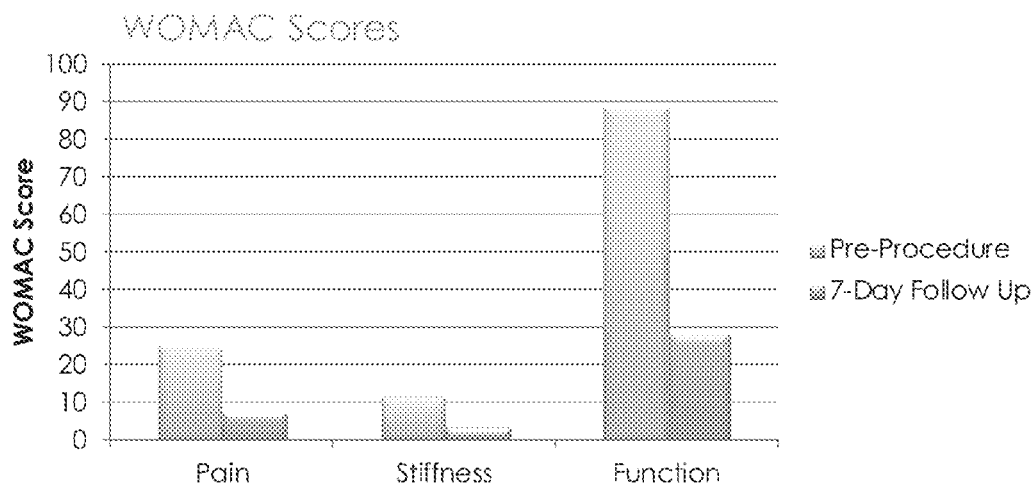
FIGS. 23A-23E summarize the WOMAC score improvement from treatment.
Figure 23B:
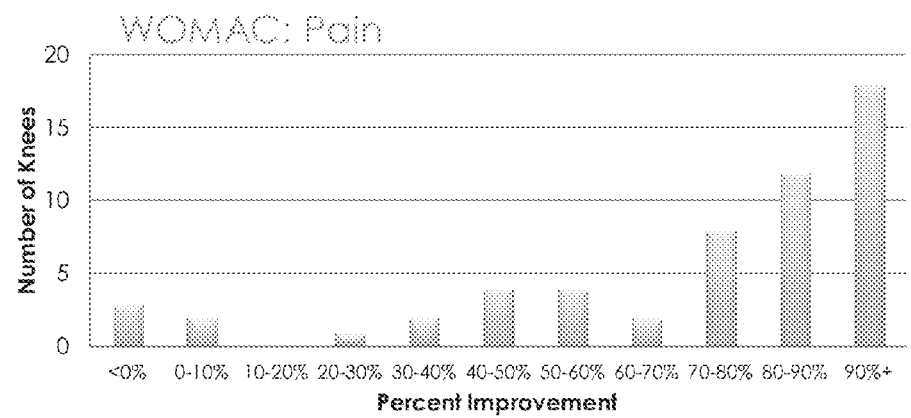
Figure 23C:
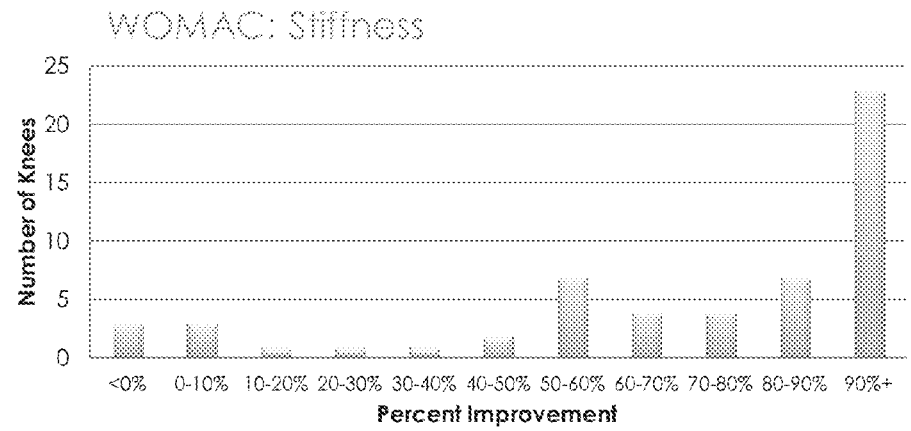
Figure 23D:
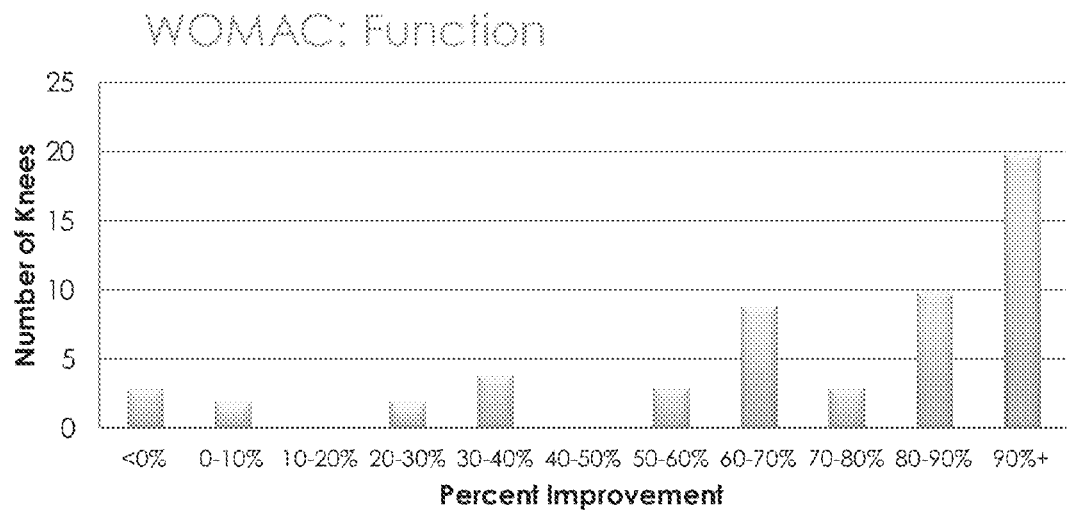
Figure 23E:
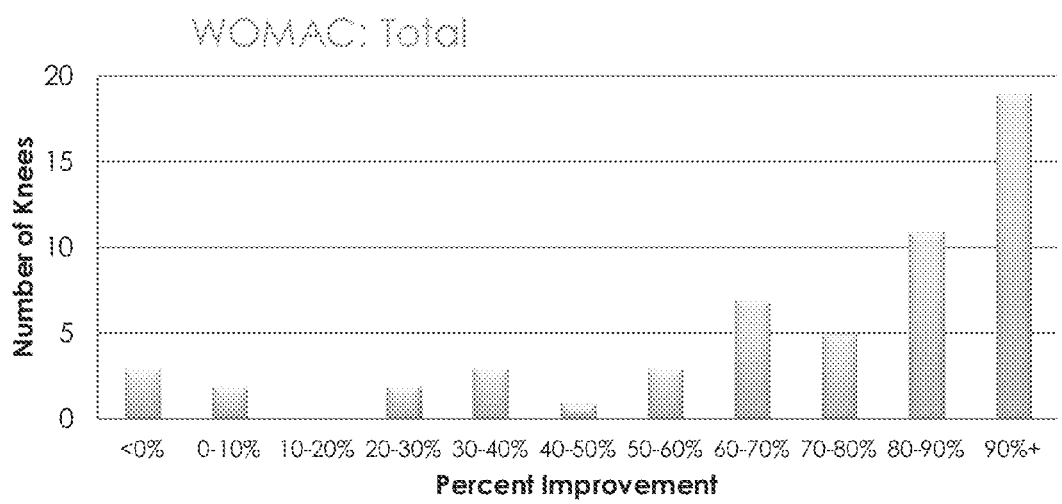

FIGS. 23A-23E summarize the WOMAC score improvement following treatment. FIG. 23A shows the average WOMAC scores for Pain, Stiffness, and Function and compares baseline assessment to 7 days post treatment for 56 knees. Total possible WOMAC scores are 50 for pain, 20 for stiffness, and 170 for function. FIG. 23B shows the number of knees showing percent improvement in WOMAC pain score from the baseline for 56 knees. FIG. 23C shows the number of knees showing percent improvement in WOMAC stiffness score from the baseline for the 56 knees. FIG. 23D shows the number of knees showing percent improvement in WOMAC function score from baseline for the 56 knees. FIG. 23E shows the number of knees showing percent improvement in WOMAC total score from the baseline for the 56 treated knees.

At Day 7, Subjects reported 79% of knees treated improved by an average of ≥2 points per question in the pain category; 84% reported improved by an average of ≥2 points per question in the stiffness category and 75% in the function category (Table 7). An overall improvement in WOMAC index was determined by averaging the scores in each category.

TABLE 7

Improvement in WOMAC Index from Baseline to Day 7 per Question.

|  | Pain | Stiffness | Function | Overall |
| --- | --- | --- | --- | --- |
| ≥2 point improvement per question | 79% (44/56) | 84% (47/56) | 75% (42/56) | 77% (43/56) |
| Average point improvement per question | 3.5 | 4.0 | 3.5 | 3.6 |
| (standard deviation) | (2.2) | (2.4) | (2.3) | (2.2) |

WOMAC scores were also assessed on a category level, by adding together the scores of each question in each category to create a score each for pain, stiffness and function for each subject. The highest possible score was 50 for pain, 20 for stiffness and 170 for function, based on the 0-10 scale used to assess each question. At baseline, subjects reported an average score of 25.2 for pain, 11.8 for stiffness and 88.8 for function (Table 8); at Day 7 post-treatment, the average scores were 7.9 for pain, 3.8 for stiffness and 28.5 for function. This represents an average improvement of 17.3 points for pain, 8.0 points for stiffness and 60.4 for function, or improvements from baseline of 70% in pain, 69% in stiffness and 70% in function. A subject's overall score was the sum of the three category scores, not weighted by number of questions; the overall scores improved from an average score of 125.8 at baseline to 40.2 at Day 7, a point improvement of 85.7 points or a 70% improvement from baseline.

TABLE 8

Improvement in WOMAC Index from Baseline to Day 7.

|  | Pain | Stiffness | Function | Overall |
|---|---|---|---|---|
| Baseline Average Score | 25.2 | 11.8 | 88.8 | 125.8 |
| (Standard deviation) | (9.4) | (3.5) | (31.2) | (42.8) |
| Post-Treatment Average Score | 7.9 | 3.8 | 28.5 | 40.2 |
| (Standard deviation) | (10.0) | (4.8) | (36.7) | (51.1) |
| Average Point Improvement Day 7 | 17.3 | 8.0 | 60.4 | 85.7 |
| (Standard deviation) | (11.1) | (4.9) | (38.5) | (53.4) |
| Average Percent Improvement Day 7 | 70% | 69% | 70% | 70% |
| (Standard deviation) | (32%) | (34%) | (32%) | (32%) |
| P-Value (Significance in change from baseline to Day 7) | 2.02E−16 | 4.08E−17 | 1.84E−16 | 7.53E−17 |

Improvement in WOMAC was tested for statistical significance using a two-tailed paired t-test and the null hypothesis $H_O$: Difference=0, where the difference was calculated by subtracting the WOMAC score reported at Day 7 from the score assessed at baseline. This was measured on a categorical level, assessing difference in score for pain, stiffness and function, as well as overall score. The test was measured using a significance level of $P<0.05$. The resulting P-values were 2.02E−16, 4.08E−17, 1.84E−16 and 7.53E−17 for pain, stiffness, function and overall subject scores, respectively (Table 8). This meets the level $P<0.05$ significance level and rejects the null hypothesis, indicating there was a statistically significant difference in WOMAC scores from baseline to Day 7.

Duration of Treatment Effect—

Figure 24:
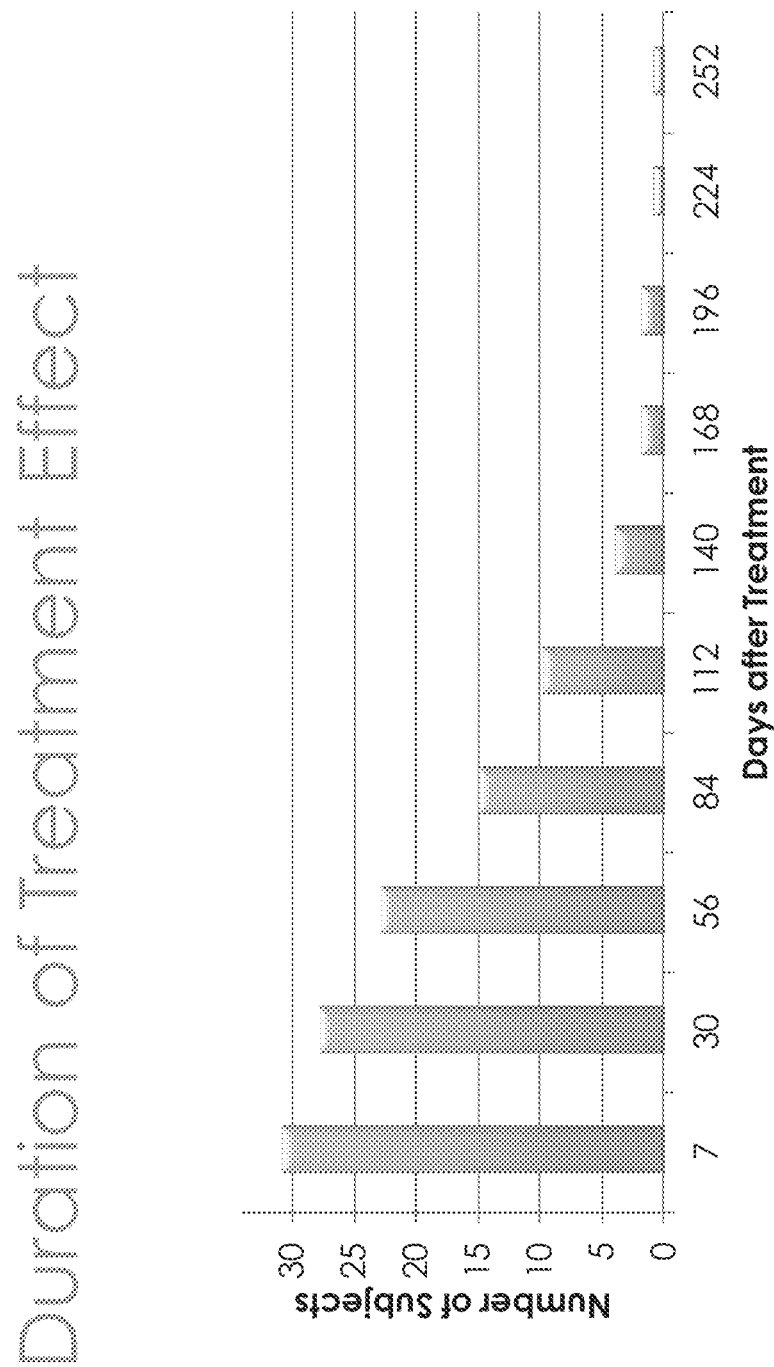
FIG. 24 is a chart showing the duration of treatment benefit during a follow up period.

Duration of treatment effect was assessed for all subjects at Day 7, Day 30 and Day 56 on a per Subject basis. FIG. 24 summarizes the duration results from the treatment. FIG. 24 shows the number of subjects reporting continued effect from treatment at follow-up points post-treatment. Additional assessments were completed via phone call every four weeks until the Subject reported no effect. At Day 7, 31/33 subjects (94%) reported continued effect from treatment (Table 9). At Day 30, 28/33 subjects (85%) reported continued effect from treatment. At Day 56, 23/33 subjects (70%) reported continued effect. Under revision 01 to 03 of the protocol, only subjects with continuing effect at 56 days were followed beyond this time point; therefore, percentages are calculated out of the entire study population (33 subjects) instead of the number of subjects followed to that time point, which is shown below. One subject exited at Day 56 with continued effect per revision 04 of the protocol; 22 subjects reporting continued effect were followed beyond Day 56.

Three Subjects did not have a follow-up phone call at Day 84 but did have a follow-up phone call at Day 112. At Day 112, 2 Subjects reported a continued effect from treatment and these Subjects are presumed to have also had an effect at Day 84. The Subject that reported there was no longer an effect at Day 112, was excluded from the Day 84 analysis. At Day 84, 19 out of the 22 subjects followed beyond Day 56 had phone-call follow-up visits, 13 of whom reported continued effect from treatment. Three subjects missed the Day 84 phone call follow-up visit; two of these Subjects reported continued effect from treatment at the Day 112 phone call. This analysis treats those two subjects as having reported effect at Day 84. The third subject who missed the Day 84 phone call follow-up visit did not report effect at Day 112, and is excluded from this analysis because it is unknown if the treatment was still effective at Day 84. Therefore, 13 subjects reported effect and 2 were presumed to have effect, leaving 15 subjects (45%) with continued effect from treatment at Day 84 (See asterisk on Table 7). Two subjects exited at Day 84 with effect and 6 exited without effect.

At Day 112, 10 subjects (30%) reported effect, four of whom exited at this point with effect.

At Day 140, 4 subjects (12%) still had effect and were followed beyond the 140-day mark, with the other four exiting without effect. Two subjects reported the treatment was no longer effective and were exited at 168 days. One subject exited with continued effect per the protocol amendment at 196 days, and the other subject exited with effect after 280 days.

TABLE 9

Subjects Reporting Continued Effect from Treatment over Initial Follow-up Period

|  | Day 7 | Day 30 | Day 56 | Day 84 | Day 112 | Day 140 | Beyond Day 140 |
|---|---|---|---|---|---|---|---|
| Number of subjects reporting at visit | 33 | 33 | 33 | 21* | 14 | 8 | 4 |
| Number with Effect | 31 | 28 | 23 | 15* | 10 | 4 | 2 |
| % with Effect (N = 33) | 94% | 85% | 70% | 45% | 30% | 12% | 6% |

*This includes the 2 Subjects who missed the Day 84 phone-call but had effect at Day 112. It does not include the 1 Subject who missed the Day 84 phone-call and did not have effect at Day 112.

Subject Experience—

Figure 25A:
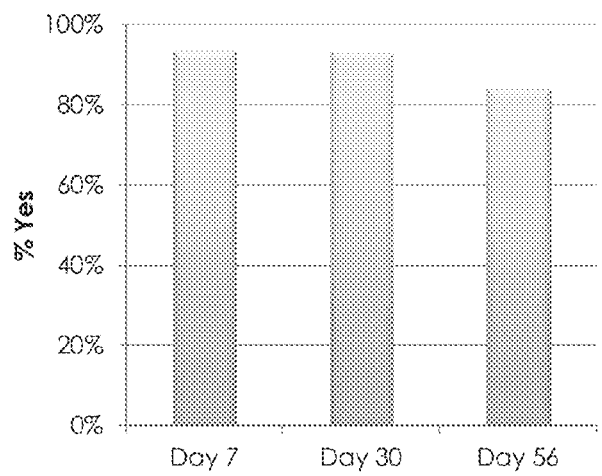
FIG. 25A and FIG. 25B are charts summarizing the patient's subjective assessment of the treatment.
Figure 25B:
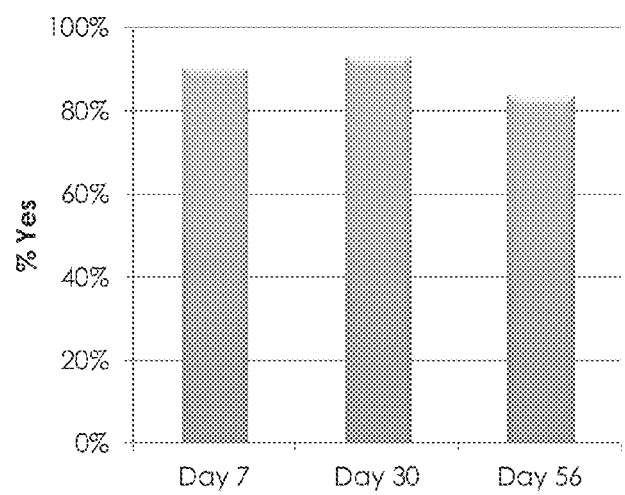

Subjects completed the post-treatment questionnaire at Day 7, Day 30 and Day 56 post-treatment visits. The questionnaire assessed subject satisfaction, subject experience with anticipated observations and subject's pain from treatment. FIG. 25A-25B summarize the patient's response to the questionnaire.

The responses for subject satisfaction are shown in Table 10 below. At Day 7, 31/33 Subjects (94%) said they would recommend the treatment to a family member; this number was 29/31 (94%) at Day 30 and 27/32 (84%) at Day 56 (Table 8). Similarly, 30/33 subjects (91%) would have the treatment again when asked at Day 7; at Day 30, 29/31 (94%) said would have the treatment again, and 27/32 (84%) said the same at Day 56.

TABLE 10

| Subject Satisfaction | | | |
|---|---|---|---|
| | Day 7 | Day 30* | Day 56* |
| Would you recommend this treatment to a family member? (% Yes) | 94% (31/33) | 94% (29/31) | 84% (27/32) |
| Would you have this treatment again? (% Yes) | 91% (30/33) | 94% (29/31) | 84% (27/32) |

Subject experience with anticipated observations was assessed; the results are described in Table 11 below. The data below reflect how the Subjects responded to the question and not the data documented during physical assessment which can be found in Table 13.

TABLE 11

| Subject Reported anticipated observations | | | | |
|---|---|---|---|---|
| | | Day 7 | Day 30* | Day 56* |
| Did the subject report any anticipated observations? (% Yes) | | 82% (27/33) | 67% (21/33) | 28% (9/32) |
| If yes, how much did they/it impact subject's daily routine? | 1 (AO had very negative impact) | 4% (1/27) | 0% (0/21) | 0% (0/9) |
| | 2 | 4% (1/27) | 5% (1/21) | 11% (1/9) |
| | 3 | 11% (3/27) | 0% (0/21) | 0% (0/9) |
| | 4 | 7% (2/27) | 0% (0/21) | 0% (0/9) |
| | 5 (No impact at all) | 74% (20/27) | 95% (20/21) | 89% (8/9) |

Subjects were also asked if pain was present from treatment and if so, to rate it on a 1-5 scale. The results are shown below in Table 12.

The subject reporting "very painful" at Day 7 is the same subject reporting "very painful" at Day 56. Due to an oversight, this subject did not complete the post-treatment questionnaire at Day 30 (see note).

TABLE 12

| Subject reported pain from treatment. | | | | |
|---|---|---|---|---|
| | | Day 7 | Day 30* | Day 56* |
| Is there any pain present from treatment? (% Yes) | | 45% (15/33) | 28% (8/31) | 6% (2/32) |
| If yes, enter scale | 1 (Not at all painful) | 33% (5/15) | 13% (1/8) | 0% (0/2) |
| | 2 | 47% (7/15) | 63% (5/8) | 50% (1/2) |
| | 3 | 13% (2/15) | 25% (2/8) | 0% (0/2) |
| | 4 | 0% (0/15) | 0% (0/8) | 0% (0/2) |
| | 5 (Very painful) | 7% (1/15) | 0% (0/8) | 50% (1/2) |

*At Day 30, two Subjects (15-011 and 15-013) answered only the question "Did the subject report any anticipated observations?" and did not complete the rest of the Subject Post-Treatment Questionnaire. At Day 56, one Subject (14-012) did not complete the questionnaire.

Treating investigators reported that the subjects who experienced the best treatment results were those with focal arthritis of the knee and/or specific localized pain of knee. Subjects with grossly altered anatomy of the knee may benefit from PENS prior to treatment as the neural anatomy of the treatment area was likely altered. Deformities of the knee may displace the ISN to the point where it no longer crosses the treatment box and, as a result, treating the complete treatment box may not yield an efficacious treatment for these subjects.

Figure 26:
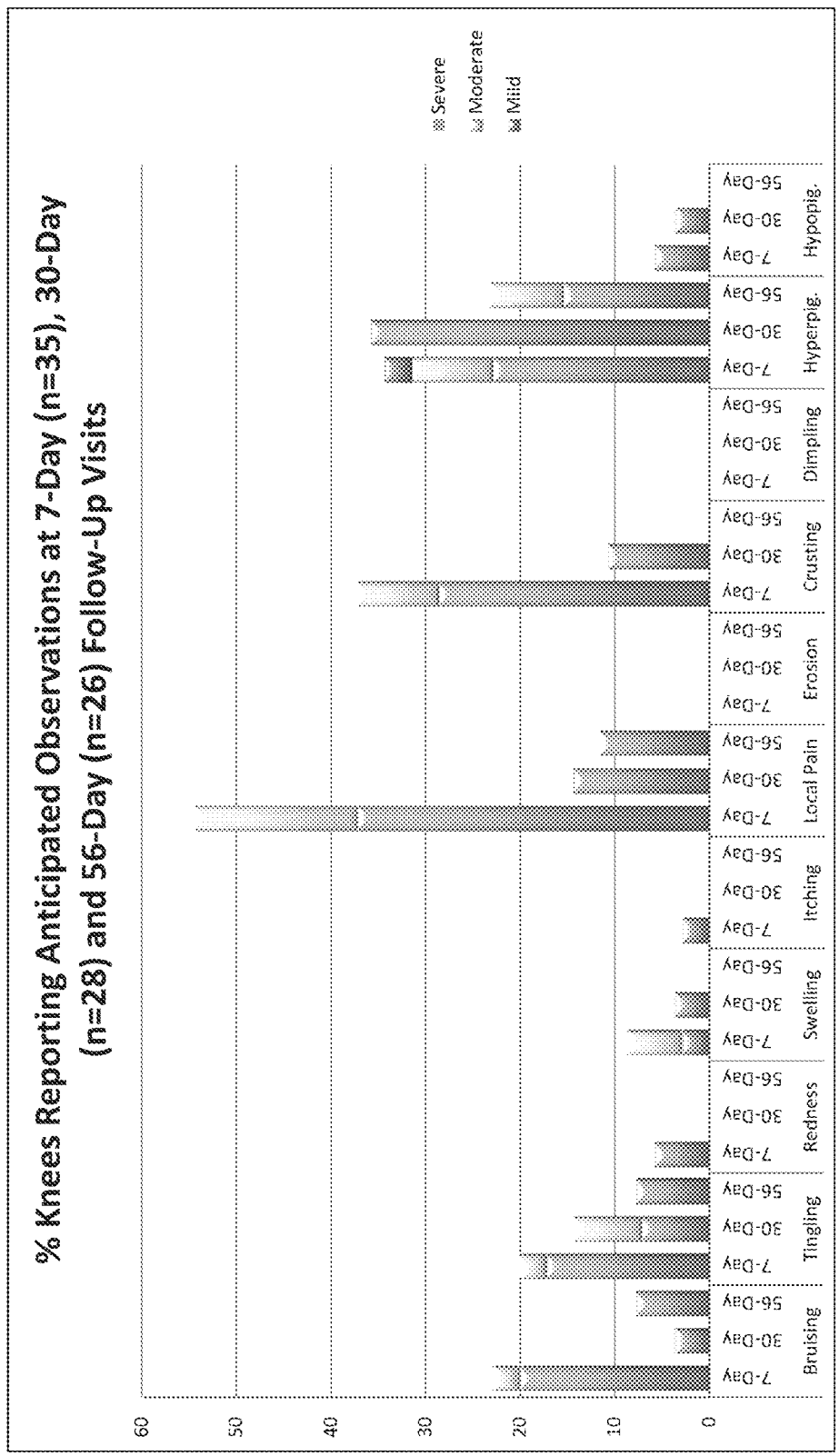
FIG. 26 is a chart summarizing the percent of knees reporting anticipated observations.

FIG. 26 summarizes the percent of knees reporting anticipated observations at 7 days, 30 days, and 56 days post-treatment. The second and third most frequently reported anticipated observations were hyperpigmentation and crusting. Both of these events may be due to vascular damage due to cold injury that leads to an occlusion of the vessels and subsequent ischemic injury of the epidermis. This epidermal injury leads to a lesion which causes crusting and in many cases, hyperpigmentation. The Cryoprobes used for treatments in this study were stainless steel and did not include the cladding elements that help prevent epidermal or dermal injury. Cryogenic cooling needles may include gold cladding (or the like) on the proximal end of the needles to provide greater skin warming and reduce vascular damage during treatment, thus protecting the dermis and epidermis. A device using a skin warmer, such as the device depicted in FIG. 2A or FIG. 3A-3B, may protect the collateral tissue during treatment of the nerve and thereby reduce the occurrence of erosion, crusting, dimpling, hyperpigmentation, and hypopigmentation. The cladding shown in FIG. 3B may also be used in some embodiments to reduce the occurrence of erosion, crusting, dimpling, hyperpigmentation, and hypopigmentation. Accordingly, the instance of hyperpigmentation and crusting may be greatly reduced with the use of such embodiments.

Thus temporary pain relief may be provided to patients suffering from osteoarthritis using embodiments of the present invention as indicated by the VAS measurements. Further, such treatments may provide an improved quality of life as indicated by the WOMAC measurements. Such treatments may also reduce the amount of drug therapy required, postpone invasive surgeries, and may provide an opportunity for physical rehabilitation (e.g., strength, flexibility, etc.). Furthermore the procedure may be used either pre- or post-operatively. Before total knee replacement surgery, the procedure may be used to limit pain, allow patients to strengthen the joint which may improve surgical outcomes. Post surgically, the procedure may be used to limit the use of opioids or other pain killers and or allow the patient to reduce residual post-surgical pain.

Based on the high treatment response rate, a 6 mm cryoprobe length for treatment of the ISN is satisfactory in most circumstances. This is consistent with the anecdotal 5 mm depth of the ISN within the treatment box as reported by the investigators. Under these assumptions, the ISN may also be successfully treated in future treatments using 5-7 mm cryoprobes or longer (e.g., 8-20 mm). With needles less than 7 mm in length, larger gauge needles (smaller diameter) may be preferred so as to limit mechanical injury to the skin and tissue to be treated. For example, in some embodiments, it may be beneficial to use 27 gauge needles.

Optionally, longer needles may be used in some embodiments (e.g., 8-15 mm, 20 mm, 90 mm etc.). Longer needles may require a smaller gauge (larger diameter) needle so they have sufficient rigidity to maintain consistent spacing when placed deep in the tissue, but not so large as to create significant mechanical injury to the skin and tissue when inserted (e.g., greater than 20 ga). Alternate configurations of the device may have two or more needles spaced generally 3-5 mm apart of lengths ranging from up to 20 mm or greater, typically of 25 gauge or 23 gauge. Single needle configurations may be even longer (e.g., 90 mm) for reaching target tissues that are even deeper (e.g., >15 mm or so below the dermis). Longer needle devices (e.g., >10 mm) may not need active heating of the skin warmer and/or cladding found in designs using shorter needle(s) as the cooling zone may be placed sufficiently deep below the dermis to prevent injury. In some embodiments, devices with single long needle configurations may benefit from active nerve location such as ultrasound or electrical nerve stimulation to guide placement of the needle. Further, larger targets may require treatment from both sides to make sure that the cold zone created by the needle fully covers the target. Adjacent treatments placing the needle to either side of a nerve during two successive treatment cycles may still provide an effective treatment of the entire nerve cross-section.

In some situations, a probe with multiple spaced apart needles may be preferable (e.g., 2, 3, 4 or more). A device employing multiple needles may decrease the total treatment duration by creating larger cooling zones. Further, a multi-needle device may be configured to provide continuous cooling zones between the spaced apart needles. In some embodiments, the needles may be spaced apart by 1-5 mm. The spacing may be dependent on the type of tissue being targeted. For example, when targeting a nerve, it may be preferable to position the nerve between the two or more needles so that cooling zones are generated on both sides of the nerve. Treating the nerve from both sides may increase the probability that the entire cross-section of the nerve will be treated. For superficial peripheral nerves, such as the infrapatellar saphenous nerve as it branches from the greater saphenous nerve and the anterior femoral cutaneous nerve, the nerves may be at depths ranging from 2-6 mm and may be smaller in diameter, typically <2 mm. Accordingly, devices for treating the ISN or other superficial peripheral nerves may comprises two or more 27 gauge needles spaced ≤2 mm apart and having typical lengths less than 7 mm (e.g., 6.9 mm); however longer needles may be required to treat the full patient population in order to access patients with altered nerve anatomy or patients with higher amounts of subcutaneous tissue such as those with high BMIs.

While the study used a treatment cycle comprising a 10 second pre-warm phase, followed by a 60 second cooling phase, followed thereafter by a 15 second post-warm phase with 40° C. skin warmer throughout, it should be understood that other treatment cycles may be implemented. In some embodiments, a pre-warming cycle can range from 0 to up to 30 seconds, preferably 5-15 seconds sufficient to pre-warm the cryoprobe and opposing skin. Treatment cooling may range from 5-120 seconds, preferably 15-60 seconds based on the flow rate, geometry of the cryoprobe, size of the therapy zone, size of the target nerve or tissue and the mechanism of action desired. Post warming can range from 0-60 seconds, preferably 10-15 seconds sufficient to return the cryoprobe to a steady state thermal condition and possibly to free the cryoprobe needle(s) from the frozen therapy zone (e.g., at least 0° C.) prior to removing the cryoprobe needles. For example, in some embodiments, devices with 6.9 mm long cladded needles may be warmed with a 30° C. heater. The treatment cycle may comprise a 10 second pre-warm phase, a 35 second cooling phase, and a 15 second post-warm phase. Advantageously, such a treatment cycle may make an equivalent cryozone as the treatment cycle used in the study in a shorter amount of time (e.g., a 35 second cooling phase compared to a 60 second cooling phase).

In some embodiments, treatment devices and treatment cycles may be configured to deliver a preferred cryozone volume. For example, in some embodiments, devices and treatment cycles may be configured to generate cryozones (defined by the 0 degree isotherm) having a cross-sectional area of approximately 14-55 mm$^2$ (e.g., 27 mm$^2$). Optionally, the devices and treatment cycles may be configured to generate cryozones having a volume of approximately 65-125 mm$^3$ (e.g., 85 mm$^3$).

Accordingly, in some embodiments, treatment cycles may be configured with cooling phases ranging between 15-75 seconds (e.g., 30 seconds, 35 seconds, 40 seconds, 45 seconds, etc.) depending on cooling fluid flow rates, warming phase durations, warming phase temperature, number of cooling needles, needle spacing, or the like in order to generate a desired cryozone. Similarly, treatment cycles may be configured with warming phases operating a temperatures ranging between 10-45° C. depending on the length of cooling phases, number of needles, needle spacing, etc. in order to generate a desired cryozone. Generally, with higher degree warming phases, the duration of the pre-warm phase and the cooling phase will be longer, however the post-warm phase duration may be reduced.

In some embodiments, devices may be configured to limit flow rate of a cooling fluid to approximately 0.34-0.80 SLPM (gas phase). Optionally, in some embodiments, it may be preferable to configure the device and the treatment cycle to maintain the tip a less than −55° C. during cooling phases. In some embodiments, it may be preferable to configure the device and the treatment cycle to have the tip return to at least 0° C. at the end of the post-warm phase so as to ensure the device may be safely removed from the tissue after the treatment cycle.

Further, the treatment box as defined by anatomical landmarks is a reliable method for treating the ISN. If the treatment box is treated in its entirety, additional methods for nerve location may not be necessary to yield an efficacious treatment result. However, additional guidance may serve as a useful tool for abbreviating the treatment area of the treatment box and may be particularly useful for patients with knee deformities. For these instances, it is recommended that PENS guidance be used to locate the nerve within the treatment box as the branches of the ISN may be very small at this point and may difficult to locate with TENS and often may not be visualizeable using ultrasound.

Subjects who did undergo nerve location with PENS prior to treatment with the cryogenic cooling needle did not demonstrate better results at any time point than subjects who did not. Subjects whose nerves were located using PENS prior to treatment demonstrated lower average VAS score improvements immediately post-treatment when compared to subjects treated without nerve location at the same study site, and all subjects treated without nerve location using PENS at the both sites. The average post-treatment VAS score reduction in subject treated with PENS was 50%. The average post-treatment VAS score reduction for those who received treatment with the cryogenic cooling device without PENS was 83% at site 15 and 82% at both sites. These differences were statistically significant (p<0.05). The average WOMAC improvement for subjects treated with the cryogenic cooling device after nerve location with PENS was 2.0. The average WOMAC improvement for subjects treated with the cryogenic cooling device without PENS nerve location at site 15 was 4.7 and 4.3 at both sites. These differences were also statistically significant (p<0.05).

It is likely that the use of PENS to locate the nerve prior to treatment did not yield an increase in treatment effect because the PENS unit was used to locate and treat a single branch of ISN. The ISN bifurcates multiple times before it reaches the patella with often 2 or 3 branches crossing the treatment box area before innervating the knee. If only one branch was treated, the remaining 2 or 3 branches of the ISN may be missed and continued to cause knee pain. It can be deduced that nerve location with PENS to find a single nerve within the treatment box is not the ideal accurate method for treatment of the ISN and that more than one branch of the ISN may need to be located and treated for optimal treatment results. Treatment may have been more efficacious if the entirety of the treatment box was searched using PENS to find and treat multiple branches within the box.

Although the above described procedures treated the infrapatellar branch of the saphenous nerve using cold to reduce pain and other symptoms associated with osteoarthritis, other methods and devices could be used to temporarily or permanently disable the ISN. Examples include thermal nerve ablation such as with RF energy, or neurolysis using injections of phenol or ethyl alcohol.

In some embodiments of the present invention, treatment guidance can rely on rigid or boney landmarks because they are less dependent upon natural variations in body size or type, e.g. BMI. Soft tissues, vasculature and peripheral nerves pass adjacent to the rigid landmarks because they require protection and support. By positioning the patient's skeletal structure in a predetermined position (e.g. knee bent 30 degrees or fully extended), one can reliably position the bones, ligaments, cartilage, muscle, soft tissues (including fascia), vasculature, and peripheral nerves. External palpation can then be used to locate the skeletal structure and thereby locate the pathway and relative depth of a peripheral nerve targeted for treatment.

A treatment of peripheral nerve tissue to at least −20° C. is sufficient to trigger 2nd degree Wallerian degeneration of the axon and mylinated sheath. Conduction along the nerve fibers is stopped immediately following treatment. This provides immediate feedback as to the location of the target peripheral nerve or associated branches when the associated motion or sensation is modified. This can be used to refine rigid landmark guidance of future treatments or to determine whether addition treatment is warranted.

Without reliable rigid landmarks, however, the treatment may rely on creating a block or treatment zone as depicted in FIG. 19 and FIG. 20. Alternatively, by using rigid landmarks, one may be able to direct the treatment pattern to specific anatomical sites where the peripheral nerve is located with the highest likelihood. Feedback from the patient immediately after each treatment may verify the location of the target peripheral nerve and its associated branches. Thus, it should be understood that in some embodiments, the use of an electronic nerve stimulation device to discover nerve location is not needed or used, since well-developed treatment zones can locate target nerves. This may be advantageous, due the cost and complexity of electronic nerve stimulation devices, which are also not always readily available.

In alternative embodiments of the invention, one could use an electronic nerve stimulation device (either transcutaneous or percutaneous) to stimulate the target peripheral nerve and its branches. With transcutaneous electric nerve stimulation (TENS) the pathway of the nerve branch can be mapped in an X-Y coordinates coincident with the skin surface. The Z coordinate corresponding to depth normal to the skin surface can be inferred by the sensitivity setting of the electrical stimulation unit. For example, a setting of 3.25 mA and pulse duration of 0.1 ms may reliably stimulate the frontal branch of the temporal nerve when it is within 7 mm of the skin surface. If a higher current setting or longer pulse duration is required to stimulate the nerve, then the depth may be >7 mm. A percutaneous electrical nerve stimulator (PENS) can also be used to locate a target peripheral nerve. Based on rigid anatomical landmarks, a PENS needle can be introduced through the dermis and advanced into the soft tissues. Periodic stimulating pulses at a rate of 1-3 Hz may be used to stimulate nerves within a known distance from the PENS needle. When the target nerve is stimulated, the sensitivity of the PENS can be reduced (e.g. lowering the current setting or pulse duration) narrowing the range of stimulation. When the nerve is stimulated again, now within a smaller distance, the PENS sensitivity can be reduced further until the nerve stimulation distance is within the therapy zone dimensions. At this point, the PENS needle can be replaced with the focused cold therapy needle(s) and a treatment can be delivered. The PENS and focused cold therapy needles can be introduced by themselves or through a second larger gage needle or cannula. This may provide a rigid and reproducible path when introducing a needle and when replacing one needle instrument with another. A rigid pathway may guide the needle to the same location by preventing needle tip deflection, which could lead to a misplaced therapy and lack of efficacy.

While many of the examples disclosed herein related to puncturing the skin in a transverse manner to arrive at a target sensory nerve, other techniques can be used to guide a device to a target sensory nerve. For example, insertion of devices can be made parallel to the surface of the skin, such that the (blunted) tip of the device glides along a particular fascia to arrive at a target sensory nerve. Such techniques and devices are disclosed in U.S. Pub. No. 2012/0089211, the entirety of which is incorporated by reference. Possible advantages may include a single insertion site, and guidance of a blunt tip along a layer common with the path or depth of the target infrapatellar saphenous nerve. This technique may be a position-treatment—thaw, reposition treatment, thaw, etc.

While the exemplary embodiments have been described in some detail for clarity of understanding and by way of example, a number of modifications, changes, and adaptations may be implemented by persons of ordinary skill in the art after reading the disclosure provided herein. Hence, the scope of the present invention is limited solely by the claims as follows.

What is claimed is:

1. A system for alleviating pain associated with osteoarthritis (OA) of a joint having a nerve, the system comprising:
   a needle having a proximal end, a distal end, a needle lumen therebetween, and a conductive coating disposed at a proximal end of the needle and extending distally along a portion of the needle, the needle configured for insertion proximate to the nerve;
   a cooling fluid supply lumen extending distally within the needle lumen to a distal portion of the needle lumen;
   a cooling fluid source couplable to the cooling fluid supply lumen to direct cooling fluid flow into the needle lumen so that liquid from the cooling flow vaporizes within the needle lumen to provide cooling to the nerve such that impact of the OA on function and/or stiffness of the joint is mitigated;
   a heating element coupled to the conductive coating of the needle, the heating element configured to deliver heating phases to the skin and tissue surrounding the nerve via the conductive coating; and
   a processor configured to control the cooling fluid flow and the heating element in response to operator input, the processor configured to provide a treatment cycle in response to a treatment instruction, the treatment cycle comprising at least one heating phase and one cooling phase.

2. The system of claim 1, wherein the cooling flow vaporizes within the needle lumen to provide a cryozone having a cross-sectional area between 14-40 mm$^2$, the cryozone being defined by a 0° C. isotherm.

3. The system of claim 1, wherein the cooling flow vaporizes within the needle lumen to provide a cryozone having a volume between 65-105 mm³, the cryozone being defined by a 0° C. isotherm.

4. The system of claim 1, wherein the processor is further configured to provide a degree of skin warmer throughout the treatment cycle.

5. The system of claim 4, wherein the degree of skin warmer comprises 28-42° C. skin warmer throughout the treatment cycle.

6. The system of claim 1, wherein the at least one heating phase comprises a pre-warm phase with the heating element before the at least one cooling phase.

7. The system of claim 6, wherein the pre-warm phase has a duration of 8-12 seconds.

8. The system of claim 6, wherein the at least one cooling phase has a duration of 20-65 seconds.

9. The system of claim 8, wherein the at least one cooling phase has a duration of less than 40 seconds, and wherein the at least one cooling phase creates a cryozone having a cross-sectional area between 14-40 mm², the cryozone being defined by a 0° C. isotherm.

10. The system of claim 8, wherein the at least one cooling phase has a duration of less than 40 seconds, and wherein the at least one cooling phase creates a cryozone having a volume between 65-105 mm³, the cryozone being defined by a 0° C. isotherm.

11. The system of claim 8, wherein the at least one heating phase further comprises a post-warm phase.

12. The system of claim 11, wherein the post-warm phase has a duration of 12-18 seconds, and wherein the distal portion of the needle has a temperature of at least 0° C. at the end of the post-warm phase.

13. The system of claim 1, wherein the needle comprises a length of 5-7 mm.

14. The system of claim 1, wherein the processor is configured to provide an audio or visual alert at completion of a treatment cycle.

15. The system of claim 1, wherein the conductive coating extends at a length of at least 2 mm along the needle.

16. The system of claim 1, wherein the conductive coating comprises a layer of gold cladding.

17. A method for alleviating pain associated with osteoarthritis (OA) of a joint having a nerve, the method comprising:
    positioning a distal end of a cryogenic cooling needle having a needle lumen proximal the nerve such that a first needle of the cryogenic cooling needle probe having a first lumen is proximal to one side of the nerve and a second needle of the cryogenic cooling needle probe spaced apart from the first needle and having a second lumen is proximal to an opposite side of the nerve so as to straddle the nerve with the first and second needles, the first and second needles being spaced apart in a range of 3 mm to 5 mm;
    delivering a treatment cycle to the target tissue with the cryogenic cooling needle, the treatment cycle comprising a cooling phase where cooling fluid flows into each of the first and second needle lumens so that liquid from the cooling flow vaporizes within each of the first and second needle lumens to provide cooling to the nerve such that impact of the OA on function and/or stiffness of the joint is mitigated.

18. The method of claim 17, wherein the treatment cycle is configured to generate a cryozone having a cross-sectional area between 14-40 mm², the cryozone being defined by a 0° C. isotherm.

19. The method of claim 17, wherein the treatment cycle is configured to generate a cryozone having a volume between 65-105 mm³, the cryozone being defined by a 0° C. isotherm.

20. The method of claim 17, further comprising providing a degree of skin warmer throughout the delivery of the treatment cycle.

21. The method of claim 20, wherein the degree of skin warmer comprises 20-42° C. skin warmer throughout the treatment cycle.

22. The method of claim 17, wherein the cryogenic cooling needle further comprises a heating element coupled with a proximal portion of each of the first and second needles; and wherein the treatment cycle further comprises at least one heating phase.

23. The method of claim 22, wherein the at least one heating phase comprises a pre-warm phase with the heating element before the at least one cooling phase.

24. The method of claim 23, wherein the pre-warm phase has a duration of 8-12 seconds.

25. The method of claim 23, wherein the at least one cooling phase has a duration of 20-65 seconds after the pre-warm phase.

26. The method of claim 25, wherein the at least one cooling phase has a duration of less than 40 seconds, and wherein the at least one cooling phase creates a cryozone having a cross-sectional area between 14-40 mm², the cryozone being defined by a 0° C. isotherm.

27. The method of claim 25, wherein the at least one cooling phase has a duration of less than 40 seconds, and wherein the at least one cooling phase creates a cryozone having a volume between 65-105 mm³, the cryozone being defined by a 0° C. isotherm.

28. The method of claim 25, wherein the at least one heating phase further comprises a post-warm phase.

29. The method of claim 28, wherein the post-warm phase has a duration of 12-18 seconds, and wherein the distal portion of the needle has a temperature of at least 0° C. at the end of the post-warm phase.

30. The method of claim 17, wherein each of the needles comprises a length of 5-7 mm.

31. The method of claim 17, further comprising placing a guide on a skin surface relative to body landmarks so as to identify a skin region overlying the target tissue.

32. The method of claim 31, wherein the guide identifies a skin region overlying an infrapatellar branch of a saphenous nerve of the patient.

33. The method of claim 32, wherein the guide identifies the skin region with a superior boundary defined by a midline of a patella of the leg; an inferior boundary defined by a tibial tubercle of the leg; a medial boundary defined by a distance lateral to a medial aspect of the patellar tendon of the leg ranging between 40-48 mm; a lateral boundary defined by a distance lateral to a lower pole of a patella of the leg ranging between 50-60 mm.

34. The method of claim 17, further comprising identifying the target tissue using a percutaneous electrical nerve stimulation device.

35. The method of claim 17, further comprising identifying the target tissue using ultrasound imaging.

36. A system for improving function and/or stiffness of joint of a patient, the joint affected with osteoarthritis and having a nerve, the system comprising:
    a plurality of 27 gauge needles, each having length between 5-7 mm and being spaced apart by not more than 3 mm, each needle further comprising a proximal end, a distal end, a needle lumen therebetween, and a conductive coating disposed at a proximal end of the needle and extending distally along a portion of the needle;

a heating element coupled with the conductive coating at the proximal portion of each of the plurality of needles, the heating element configured to deliver heating phases to the skin and tissue surrounding the nerve of the patient via the conductive coating when the plurality of needles are inserted proximal to the nerve;

a plurality of cooling fluid supply lumens extending distally within the each of the plurality of needle lumens to a distal portion of each of the plurality of needle lumens;

a cooling fluid source coupleable to the plurality of cooling fluid supply lumens to direct cooling fluid flow into the plurality of needle lumens so that liquid from the cooling flow vaporizes within the plurality of needle lumens to deliver adjacent cooling phases to the nerve such that impact of the OA on function and/or stiffness of the joint is mitigated;

a processor configured to control the cooling fluid flow and the heating element in response to operator input.

37. The system of claim 36, wherein the conductive coating extends at a length of at least 2 mm along each needle.

38. The system of claim 36, wherein the conductive coating comprises a layer of gold cladding.

\* \* \* \* \*